(12) United States Patent
Franck et al.

(10) Patent No.: US 6,546,277 B1
(45) Date of Patent: Apr. 8, 2003

(54) INSTRUMENT GUIDANCE SYSTEM FOR SPINAL AND OTHER SURGERY

(75) Inventors: Joel I. Franck, Durham, ME (US); Frederick C. Haer, Brunswick, ME (US); Ronald J. Franklin, Bowdoinham, ME (US)

(73) Assignee: Neutar L.L.C., Bowdoinham, ME (US)

( * ) Notice: Subject to any disclaimer, the term of this patent is extended or adjusted under 35 U.S.C. 154(b) by 0 days.

(21) Appl. No.: 09/317,676

(22) Filed: May 24, 1999

Related U.S. Application Data

(63) Continuation-in-part of application No. 09/063,658, filed on Apr. 21, 1998, now abandoned, and a continuation-in-part of application No. 09/063,930, filed on Apr. 21, 1998, now Pat. No. 6,273,896.

(60) Provisional application No. 60/096,384, filed on Aug. 12, 1998.

(51) Int. Cl.[7] .................................................. A61B 6/00

(52) U.S. Cl. ....................... 600/426; 600/427; 600/429; 606/130

(58) Field of Search .............................. 600/411, 414, 600/417, 426, 427, 429; 606/130

(56) References Cited

U.S. PATENT DOCUMENTS

| | | |
|---|---|---|
| 4,706,665 A | 11/1987 | Gouda |
| 4,809,694 A | 3/1989 | Ferrara |
| 4,945,914 A | 8/1990 | Allen |
| 4,991,579 A | 2/1991 | Allen |
| 5,016,639 A | 5/1991 | Allen |
| 5,050,608 A | 9/1991 | Watanabe et al. |
| 5,094,241 A | 3/1992 | Allen |
| 5,097,839 A | 3/1992 | Allen |
| 5,099,846 A | 3/1992 | Hardy |
| 5,107,839 A | 4/1992 | Houdek et al. |
| 5,119,817 A | 6/1992 | Allen |
| 5,142,930 A | 9/1992 | Allen et al. |
| 5,186,174 A | 2/1993 | Schlondorff et al. |
| 5,201,742 A | 4/1993 | Hasson |
| 5,211,164 A | 5/1993 | Allen |

(List continued on next page.)

OTHER PUBLICATIONS

Bucholz et al., "Intraoperative localization using a three dimensional optical digitizer," *Proceedings of Clinical Application of Modern Imaging Technology, SPIE*, 1894:312–322, 1993.

Foley et al., "Image–Guided Spine Surgery," *Clinical Frontiers of Interactive Image–Guided Neurosurgery*, 7(2):171–186, 1996.

*Stereotactic and Functional Neurosurgery*, textbook: chapters 1, 3, 4–5, 13, 18–19, 21–22, 24–26, 40, 43, 214–215; Gildenberg and Tasker, editors; McGraw–Hill, 1997.

Smith et al., "The Neurostation™—A Highly Accurate, Minimally Invasive Solution to Frameless Sterotactic Neurosurgery," *Computerized Medical Imaging and Graphics*, 18(4):247–256, 1994.

*Primary Examiner*—Ruth S. Smith
(74) *Attorney, Agent, or Firm*—Fish & Richardson P.C.

(57) ABSTRACT

A method and apparatus for positioning a surgical instrument during stereotactic surgery on a body, for example, during spinal surgery or general surgery. A mounting device is attached to a bone structure of the body, for example, by attaching a rail to the spine for spinal surgery. In spinal surgery, the rail is attached to the spine by clamping the rail to two spinous processes and adjusting the separation of the two spinous processes to match the separation of the two processes in three-dimensional scanned image, thereby matching a curvature of the spine with a corresponding curvature of the spine in the image. Multiple of fiducial points are located on the body in relation to the mounting device. An adjustable guidance fixture that includes an instrument guide for guiding the surgical instrument along a constrained trajectory relative to the instrument guide is attached to the mounting device.

10 Claims, 42 Drawing Sheets

U.S. PATENT DOCUMENTS

| | | | |
|---|---|---|---|
| 5,222,499 A | 6/1993 | Allen | |
| 5,230,338 A | 7/1993 | Allen et al. | |
| 5,251,127 A | 10/1993 | Raab | |
| 5,305,203 A | 4/1994 | Raab | |
| 5,371,778 A | 12/1994 | Yanof et al. | |
| 5,383,454 A | 1/1995 | Bucholz | |
| 5,394,457 A | 2/1995 | Leibinger et al. | |
| 5,394,875 A | 3/1995 | Lewis et al. | |
| 5,397,329 A | 3/1995 | Allen | |
| 5,494,034 A | 2/1996 | Schlondorff et al. | |
| 5,515,160 A | 5/1996 | Schulz et al. | |
| 5,517,990 A | 5/1996 | Kalfas et al. | |
| 5,531,227 A | 7/1996 | Schneider | |
| 5,531,520 A | 7/1996 | Grimson et al. | |
| 5,551,429 A | 9/1996 | Fitzpatrick et al. | |
| 5,575,794 A | 11/1996 | Walus et al. | |
| 5,588,430 A | 12/1996 | Bova et al. | |
| 5,590,215 A | 12/1996 | Allen | |
| 5,595,193 A | 1/1997 | Walus et al. | |
| 5,603,318 A | 2/1997 | Heilbrun et al. | |
| 5,622,170 A | 4/1997 | Schulz | |
| 5,638,819 A | 6/1997 | Manwaring et al. | |
| 5,645,549 A | 7/1997 | Boyd et al. | |
| 5,660,185 A | 8/1997 | Shmulewitz et al. | |
| 5,662,111 A | 9/1997 | Cosman | |
| 5,665,095 A | 9/1997 | Jacobson | |
| 5,682,886 A | 11/1997 | Delp et al. | |
| 5,695,501 A | 12/1997 | Carol et al. | |
| 5,702,406 A | 12/1997 | Vilsmeier et al. | |
| 5,728,106 A | 3/1998 | Misko et al. | |
| 5,730,130 A | 3/1998 | Fitzpatrick et al. | |
| 5,732,703 A | 3/1998 | Kalfas et al. | |
| 5,748,767 A | 5/1998 | Raab | |
| 5,752,962 A | 5/1998 | D'Urso | |
| 5,769,078 A | 6/1998 | Kliegis | |
| 5,769,789 A | 6/1998 | Wang et al. | |
| 5,769,861 A | 6/1998 | Vilsmeier | |
| 5,776,064 A | 7/1998 | Kalfas et al. | |
| 5,791,231 A | 8/1998 | Cohn et al. | |
| 5,795,294 A | 8/1998 | Luber et al. | |
| 5,799,099 A | 8/1998 | Wang et al. | |
| 5,800,352 A | 9/1998 | Ferre et al. | |
| 5,807,378 A | 9/1998 | Jensen et al. | |
| 5,814,038 A | 9/1998 | Jensen et al. | |
| 5,817,106 A | 10/1998 | Real | |
| 5,823,960 A | 10/1998 | Young et al. | |
| 5,829,444 A | 11/1998 | Ferre et al. | |
| 5,848,967 A | 12/1998 | Cosman | |
| 5,851,183 A | 12/1998 | Bucholz | |
| 5,871,018 A | 2/1999 | Delp et al. | |
| 5,871,445 A | 2/1999 | Bucholz | |
| 5,871,487 A | 2/1999 | Warner et al. | |
| 5,873,822 A | 2/1999 | Ferre et al. | |
| 5,891,034 A | 4/1999 | Bucholz | |
| 5,891,157 A | 4/1999 | Day et al. | |
| 5,891,158 A | 4/1999 | Manwaring et al. | |
| 5,916,164 A | 6/1999 | Fitzpatrick et al. | |
| 5,920,395 A | 7/1999 | Schulz | |
| 5,954,647 A | 9/1999 | Bova et al. | |
| 5,957,934 A | 9/1999 | Rapoport | |
| 5,961,456 A | 10/1999 | Gildenberg | |
| 5,967,982 A * | 10/1999 | Barnett | 600/429 |
| 5,976,156 A | 11/1999 | Taylor et al. | |
| 5,984,930 A | 11/1999 | Maciunas et al. | |
| 6,314,310 B1 * | 11/2001 | Ben-Haim et al. | 600/427 |

\* cited by examiner

BRAIN SURGERY

INSTRUMENT GUIDANCE SYSTEM FOR SPINAL AND OTHER SURGERY

RELATED APPLICATIONS

This is a continuation-in-part application of U.S. application "INSTRUMENT GUIDANCE FOR STEREOTACTIC SURGERY," Ser. No. 09/063,658 filed Apr. 21, 1998, now abandoned, and a continuation-in-part of U.S. application "REMOVABLE FRAMES FOR STEREOTACTIC LOCALIZATION," Ser. No. 09/063,930 filed Apr. 21, 1998, which is issued as U.S. Pat. No. 6,273,896 on Aug. 14, 2001, and also claims the benefit of U.S. Provisional application Ser. No. 60/096,384, filed Aug. 12, 1998.

BACKGROUND

This invention relates to instrument guidance for stereotactic surgery.

Stereotactic localization is a method for locating a target within a three-dimensional object. This method is used in the medical arts and sciences to locate a target in the human body, in particular in the brain or spine, for medical and surgical treatment. Stereotactic surgery has a history dating back to the turn of the century, when the Horsely-Clark Apparatus was described as a mechanical frame system in which an animal was immobilized. This frame system permitted reproducible targeting within the animal's brain for physiological experiments. This and similar technology found application in 1948 in the work of Wycis and Speigel. In their work, a frame was attached to a human skull. The frame permitted targeting of sites within the human brain for neurosurgical treatment. A detailed survey of the field of stereotactic surgery can be found in *Textbook of Stereotactic and Functional Neurosurgery*, P. L. Gildenberg and R. R. Tasker (eds.), McGraw-Hill, June 1997 (ISBN: 0070236046).

One approach to stereotactic surgery involves the following steps. Fiducial scanning markers are attached to the body in one of a variety of manners, including using an attachable frame or attaching the markers to the skin with an adhesive. A scan is then taken of a body, for example of the head, to produce a three-dimensional image of the body. Scanning can be done using a variety of techniques including CT, MRI, PET, and SPECT. Images of the fiducial scanning markers that are located around the body are then located in the three-dimensional image at fiducial image points. Points of interest, such as the location of a tumor, are located in the three-dimensional image with reference to these fiducial image points. The body and the image are registered by matching the locations of the scanning markers and the coordinates of the fiducial image points. In an approach to stereotactic brain surgery, a three-dimensional frame is screwed to the patient's skull prior to scanning the head. This frame serves as a mechanical reference mechanism that supports scanning fiducial markers at fiducial points around the body. The frame remains attached to the patient's skull from before scanning until after surgery is complete. Prior to surgery, a mechanical guide assembly is attached to the frame. The relative location in the image of the point of interest with respect to the fiducial image points is determined, and this relationship is used to adjust the mechanical guide assembly with respect to the fiducial points on the frame. Using the adjusted mechanical guide assembly, a surgical instrument is then guided to a location in the body that corresponds to the point of interest in the image.

In another form of stereotactic surgery, known generally as "image-guided" stereotactic surgery, rather than relying on mechanical adjustment of a guide assembly, visual feedback is provided to a surgeon by displaying a composite image formed from the scanned three-dimensional image and a synthesized image of a hand-held surgical instrument. The surgeon guides the hand-held instrument into the body using the visual feedback. In this form of surgery, a frame is attached to the patient and a scan is taken as described above. After scanning, the head and frame are secured in a fixed position, for example, fixed to an operating table. In order to display the image of the surgical instrument in a proper relationship to the scanned image, the position and orientation of the instrument is sensed using a localization apparatus that remains in a fixed position relative to the body. The localization apparatus can be coupled to the surgical instrument using an articulated mechanical arm on which the surgical instrument is attached. Sensors in the joints of the arm provide signals that are used to determine the location and orientation of the instrument relative to a fixed base of the mechanical arm. Some more recent systems do not use mechanical coupling between the surgical instrument and the localization apparatus and instead rely on remote sensing of small localized energy emitters (e.g., sources or transducers of energy) fixed to the instrument. For example, a camera array is used to locate light-emitting diodes (LEDs) that are attached to the instrument. The locations of the LED images in the camera images are used to determine the three-dimensional physical locations of the LEDs relative to the camera array. The locations of multiple LEDs attached to the instrument are then used to determine the location and orientation of the instrument. Another example of remote sensing uses sound generators and a microphone array and relies on the relative time of arrival of acoustical signals to determine the three-dimensional locations of the sound generators.

Before a synthesized image of the instrument can be combined with the scanned image in a proper relationship, some form of registration is required. For example, the tip of the surgical instrument can be placed at each of several fiducial markers for which corresponding images have been located in the three-dimensional scanned image. Registration of the synthesized image of the instrument and the scanned image can thereby be established.

In a variant of image-guided stereotactic surgery, generally known as "dynamic referencing," the head and frame are secured in a fixed position, as in the image-guided approach. However, unlike other image-guided techniques, the sensors (e.g., cameras) of the localization apparatus are not at a fixed location. In order to compensate for the motion of the sensors, energy emitters are fixed to the frame as well as to the instrument. At any point in time, the location and orientation of the frame relative to the sensors as well as the location and orientation of the instrument relative to the sensors are both determined, and the differences in their locations and orientations are used to compute the location and orientation of the instrument relative to the frame. This computed location of the instrument is then used to display the synthesized image of the surgical instrument in an appropriate relationship to the scanned image.

Still another approach to stereotactic surgery, generally known as "frameless image-guided" stereotactic surgery, does not rely on attaching a frame to the body before scanning. Instead, adhesive fiducial scanning markers are applied to the scalp, or small screws are inserted into the skull, and the patient is scanned as in the techniques described above. During surgery, the patient is immobilized and locked in place using a head clamp or a frame. The image-guided stereotactic approach described above is then followed, including the registration procedure described above to establish the locations of the fiducial scanning markers relative to the instrument.

In image-guided techniques, a surgeon can rely on a variety of views of a three dimensional scanned image. These views can include a three-dimensional surface view with an adjustable point of view (e.g., a perspective view with surface shading). In addition, planar (i.e., two-dimensional) views of the image can be displayed. In particular, three two-dimension "slices" through orthogonal planes of the image are typically displayed, with the orientations of the planes being sagittal (dividing a head into a left and a right part), coronal (dividing a head into a front and a back part), and axial (dividing a head into an upper and lower part). As the orientations of the planes are predetermined, the particular planes that are displayed can be determined by the point of intersection of the three planes. A point, such as the tip of a probe, can be displayed in a three-dimensional surface view as a point in a appropriate geometric relationship. The point can be displayed in a planer view by orthogonally projecting the point onto the associated plane. A line can be displayed in a planar view as an orthogonal projection onto the associated plane, or as the point of intersection of the line and the associated plane. Note that if a first point, such as a surgical entry point is used to determine which planes are displayed, a second point, such as a surgical target point, does not in general fall in any of the displayed planes.

Planar views of a three-dimensional scan can also use alternative orientations than the standard sagittal, coronal, and axial orientations described above, allowing two points to lie in two orthogonal planes, and one of the two points to additionally lie in a third orthogonal plane. In particular, a "navigational" view can be determined according to two points in an image, such as an entry point at the surface of a body and a target point within the body. The line joining the entry point and the target point is chosen as the intersection of two orthogonal planes, navigation planes 1 and 2. The orientation of navigational planes 1 and 2 is arbitrary (that is, the two planes can be rotated together around their intersecting line). A third plane, orthogonal to navigation planes 1 and 2, provides a "bird's eye" view looking from the entry point to the target point. This bird's eye plane is typically chosen to pass through the target point. (Such a navigational view is shown in FIG. 14*a*). Using a navigational view, the orientation of a surgical instrument is typically shown as a line projected orthogonally onto the two navigational planes, and as the point of intersection of the line and the bird's eye plane. Manipulating an instrument using such a navigational view for feedback requires considerable practice and is not intuitive for many people.

Image-guided frameless stereotaxy has also been applied to spine surgery. A reference frame is attached to an exposed spinous process during open spine surgery, and a probe is used to register the patient's spine with scanned image of the spine. Anatomical landmarks are used as fiducial points which are located in the scanned image. Visual feedback is provided to manually guide placement of instruments, such as insertion of pedicle screws into the spinal structures.

SUMMARY

In one aspect, in general, the invention is a method for positioning a surgical instrument during stereotactic surgery on a body, for example, during spinal surgery or general surgery. In this method, the body has been previously scanned to produce a three-dimensional image of the body which includes a target. A mounting device is attached to a bone structure of the body, for example, by attaching a rail to the spine, or a mounting plate to the pelvis and attaching a rod to the mounting plate. Multiple of fiducial points are located on the body in relation to the mounting device. For example, the fiducial points are anatomical points which are located using a remote sensing device that is used to track the mounting device and a probe that is placed at the fiducial points. The method also includes providing an adjustable guidance fixture that includes an instrument guide for guiding the surgical instrument along a constrained trajectory relative to the instrument guide. A location and orientation of the instrument guide is tracked and a position of the constrained trajectory in the three-dimensional image is computed. The guidance fixture is adjusted relative to the mounting device using a first constrained motion followed by a second constrained motion, so that the constrained trajectory of the instrument guide passes through the target. The method further includes driving the surgical instrument along the constrained trajectory toward the target, and subsequently removing the mounting device from the bone structure.

The method can include one or more of the following features.

The rail is attached to the spine by clamping the rail to two spinous processes and adjusting the separation of the two spinous processes to match the separation of the two processes in three-dimensional scanned image, thereby matching a curvature of the spine with a corresponding curvature of the spine in the image.

Locating the fiducial points in relation to the rail includes tracking a location and orientation of the rail using a remote sensing device and also tracking a location of a point on a probe using the remote sensing device. The point on the probe is positioned at the fiducial points. When the fiducial points are anatomical points of one vertebral segment, this facilitates poly-segmental tracking via unisegmental mapping registration The tracked location and orientation of the rail is compared to the tracked location of the point on the probe to determine the location of the fiducial points in relation to the rail.

In another aspect, in general, the invention is a method for positioning a surgical instrument during stereotactic spinal surgery, the spine having been previously scanned to produce a three-dimensional image of the spine which includes a target on the spine. A longitudinal rail is attached to the spine. Attaching the rail to the spine can include clamping the longitudinal rail to two spinous processes and adjusting the separation of the two spinous processes to match a separation of the two processes in the three-dimensional image, thereby maintaining a fixed geometric relationship between the longitudal rail and a portion of the spine between the two spinous processes and matching a curvature of that portion spine with a corresponding curvature of that portion of the spine in the three-dimensional image. Multiple anatomical fiducial points are located on the spine in relation to the longitudinal rail. Locating these points includes tracking a location of the longitudinal rail with using a remote sensing device, tracking a location of a probe positioned at each of the fiducial points using the remote sensing device, and comparing the location of the probe and the location of the longitudinal rail at each of the fiducial points. An adjustable guidance fixture that includes an instrument guide for guiding the surgical instrument along a constrained trajectory relative to the instrument guide is attached to the rail. A location and orientation of the instrument guide is tracked and a position of the constrained trajectory in the three-dimensional image is computed. A planar section of the three-dimensional image of the body in conjunction with a representation of the constrained trajectory, the planar section containing the target on the spine. The guidance fixture is adjusted using a first constrained motion until the constrained trajectory of the instrument guide lies in a plane corresponding to the displayed planar section and using a second constrained motion, such that the orientation continues to lie in the plane corresponding to the displayed planar section, until the constrained trajectory passes through the target point. The surgical instrument is driven along the constrained trajectory toward the target, including tracking a location of the surgical instrument and displaying the location of the surgical instrument in conjunction with the scanned image.

In another aspect, in general, the invention is an apparatus for stereotactic surgery on a spine. The apparatus includes a guidance fixture that includes an instrument guide for moving a surgical instrument along a constrained trajectory. The apparatus also includes a mounting device that includes a longitudinal rail and multiple clamps for securing the longitudinal rail to the spine, and an adjustment mechanism for adjusting the location and orientation of the constrained trajectory relative to the mounting device. The apparatus also includes a signaling device for providing signals related to a location and orientation of the constrained trajectory.

In another aspect, in general, the invention is an apparatus for stereotactic surgery on a body. The apparatus includes a guidance fixture that includes (a) an instrument guide for moving a surgical instrument along a constrained trajectory relative to the instrument guide, (b) an adjustable portion supporting the instrument guide, including a base having a central axis and an adjustment mechanism coupled between the base and the instrument guide, wherein a configuration of the adjustment mechanism determines an orientation of the instrument guide relative to the central axis of the base, and (c) a signaling device for providing a signal representation of the configuration of the adjustment mechanism. The apparatus also includes a mounting device coupled to the guidance fixture for attaching the guidance fixture to the body, the mounting device including an attachment portion for rigid attachment to a bone structure of the body.

The invention can include one or more of the following features.

The attachment portion of the mounting device includes a first clamp for attaching the mounting device to a first point on a spine, and the mounting device further includes a longitudinal rail.

The attachment portion includes a second clamp for attaching the mounting device to a second point on the spine.

The mounting device further includes a transverse rail coupled between the longitudinal rail and the guidance fixture and an adjustable coupler coupling the longitudinal rail and the transverse rail.

The mounting device further includes a tracking device which when the mounting device attached to the body is rigidly coupled to the body, the tracking device provides a signal representation of a position of the body.

The tracking device includes multiple tracking markers, for example energy reflectors or emitters, and the signal representation of the position of the body includes multiple signals, such as electromagnetic, optical, or acoustic signals, propagating from corresponding tracking markers.

The mounting device further includes an adjustable portion coupling the attachment portion to the guidance fixture.

The attachment portion includes a mounting plate for attaching the mounting device directly to a bone structure of the body.

The mounting device further includes a rod removably attached to the mounting base.

An advantage of the invention is that it permits accurate stereotactic surgery on various parts of the body, and in particular, allows accurate stereotactic surgery on the spine. Attaching the guidance fixture to a mounting device that is attached to a bone structure, such as a rail attached to a spine, provides a way of holding the guidance fixture in a fixed relationship to a target in the body.

An advantage of using a spinal rail is that by using two clamps, the spine can be maintained in a fixed curvature and the curvature can be adjusted to match the curvature at the time that a scan was taken. In this way, a single spinal segment can be registered with scanned image and thereby achieve registration for a series of spinal segments. This reduces the amount of time taken in surgery that would be needed to repeatedly re-register each spinal segment.

Other features and advantages are apparent from the following description and from the claims.

DESCRIPTION

Brain Surgery

Figure 1:
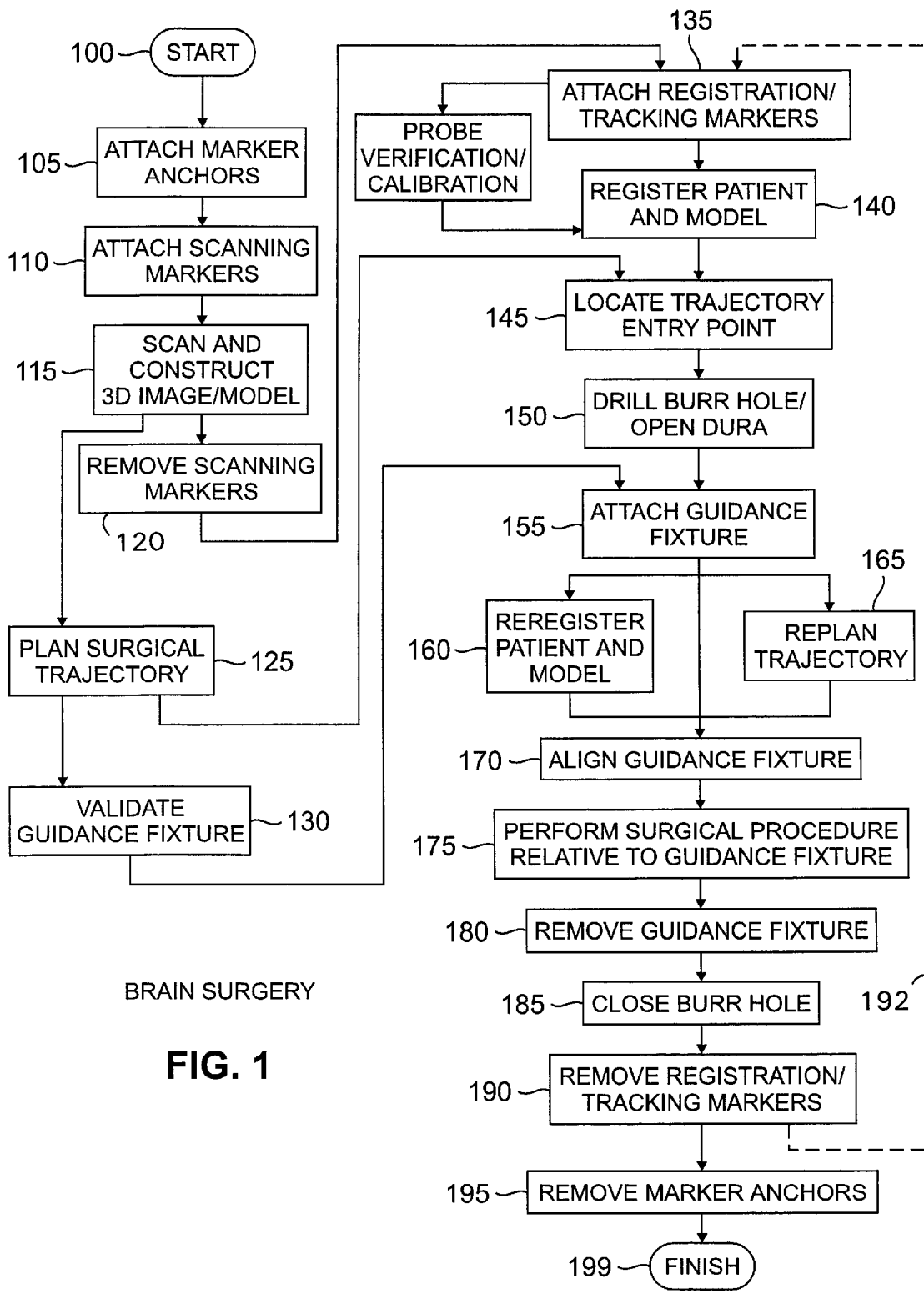
FIG. 1 is a flowchart of a stereotactic brain surgery procedure.

Referring to FIG. 1, an aspect of the invention relates to stereotactic brain surgery. This approach to brain surgery involves a series of steps, shown in FIG. 1, from start 100 prior to scanning through finish 199 after the surgical phase of a procedure is completed. There are generally two phases to the approach. The first phase involves creating a three-dimensional image of the head (steps 105, 110, 115, 120), planning a surgical trajectory based on the image (step 125), and validating the guidance fixture (step 130) that will be used during the surgical procedure. The second phase involves the remaining steps (steps 135 through 195) that are used to carry out the actual surgical procedure. The steps of the first phase can be carried out quite some time before those of the second phase. For example, creating the three-dimensional image of the head can be done on one day, and the steps used to carry out the actual surgery can be done on a subsequent day. Also, the steps of the second phase may be repeated, for example on several different days, illustrated by transition 192 between steps 195 and 135.

Pre-Operative Phase

Figure 2:
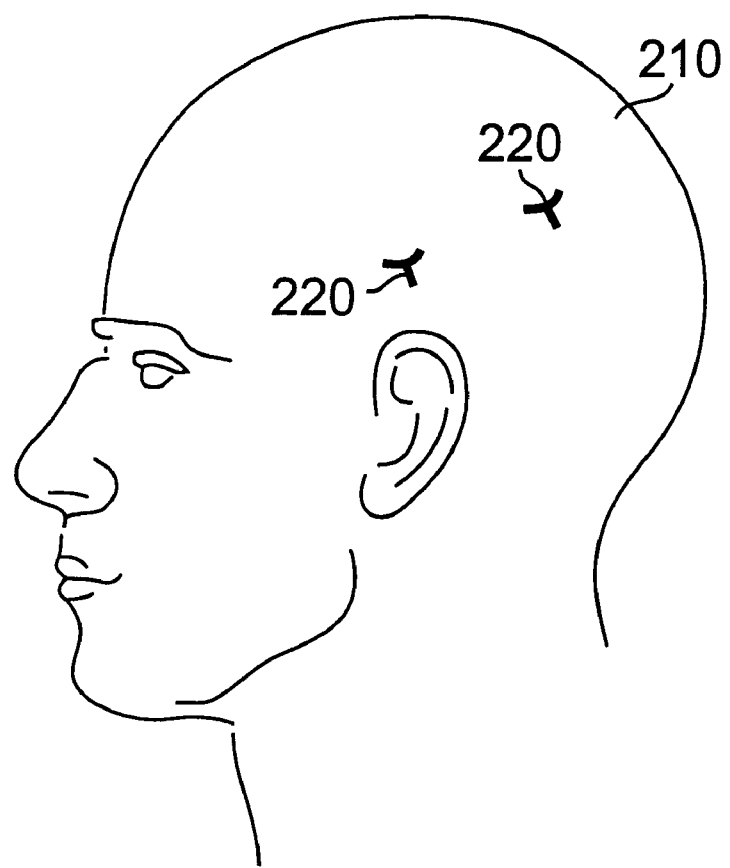
FIG. 2 is a head with threaded inserts implanted including a cross-sectional view of the skull and a threaded insert.
Figure 2:
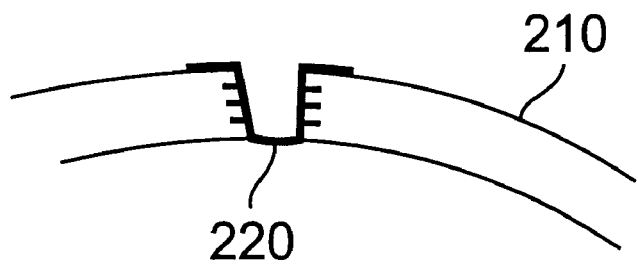

One to three days prior to surgery, the patient is seen in a post anesthesia care unit (PACU) or other suitable location. Referring to FIG. 1, the first step of the procedure is to attach anchors to which scanning, registration, and tracking markers will be subsequently attached (step 105). Referring to FIG. 2, the anchors include two threaded inserts 220 that are surgically implanted into the patient's skull 210 using a template (described below). The template precisely determines the separation and parallel orientation of inserts 220.

Figure 3:
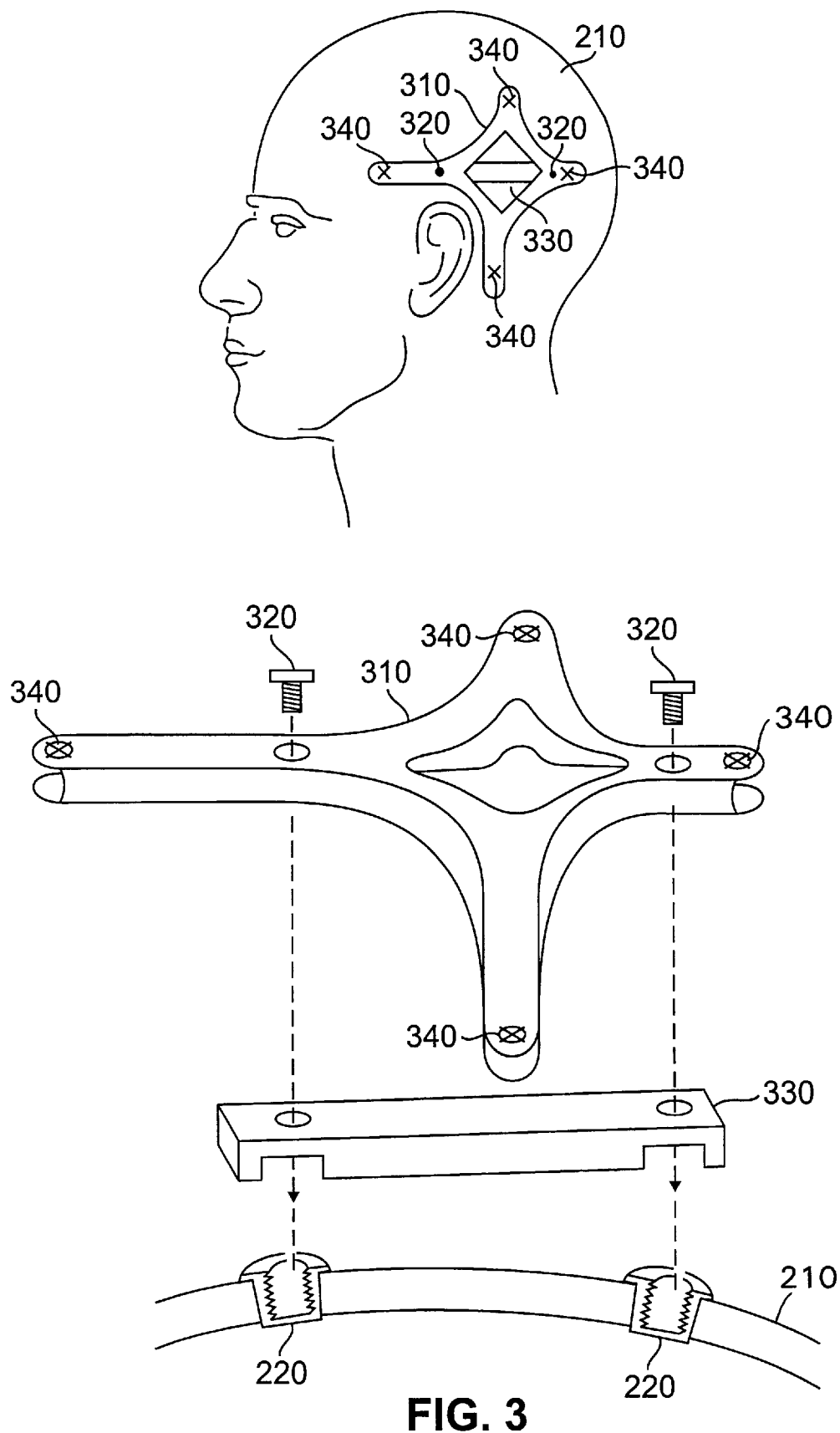
FIG. 3 is a head with a scanning MIRRF attached including a detailed exploded view of the attachment of the MIRRF to the implanted threaded inserts.

Referring to FIG. 3, a rigid cross-shaped device, a scanning "miniature removable reference frame" (scanning MIRRF) 310, is next attached to threaded inserts 220 using screws 320 (FIG. 1, step 110). A retention plate 330 is used to aid precise reattachment of scanning MIRRF 310 to the skull. Retention plate 330 is also used as the template during insertion of threaded inserts 220. Scanning MIRRF 310 includes four fiducial scanning markers 340 that will be visible in the scanned image. Scanning MIRRF 310 is made from a material that is chosen to interfere as little as possible with the type of scan that will be performed. For example, for MRI and CT scans, the chosen material can be polycarbonate, which results in scanning MIRRF 310 being almost invisible in the scanned image. Fiducial scanning markers 340 are mounted in spherical cavities in scanning MIRRF 310. The design of the cavities is such that the "press-in" marker inserts can be removed for cleaning. The star-shaped design of scanning MIRRF 310 is such that, when attached, the elongated part of the star extends behind or in front of the ear so that mounting screws 320 are located toward the top of the skull where soft tissue thickness is minimal and skull thickness is maximal. This minimal tissue thickness allows threaded inserts 220 to be implanted easily under local anesthetic by making a small incision. As an alternative to attaching a single MIRRF as shown in FIG. 3, multiple MIRRFs can be attached in a similar manner to increase the number or separation of the scanning markers.

Figure 4:
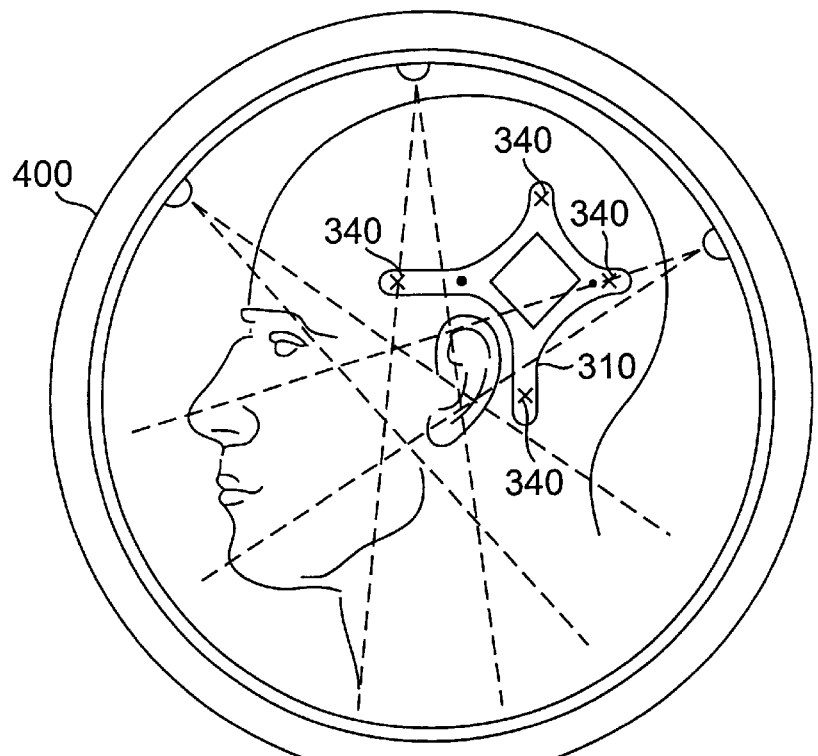
FIG. 4 illustrates scanning of a head on which a scanning MIRRF is attached.
Figure 4:
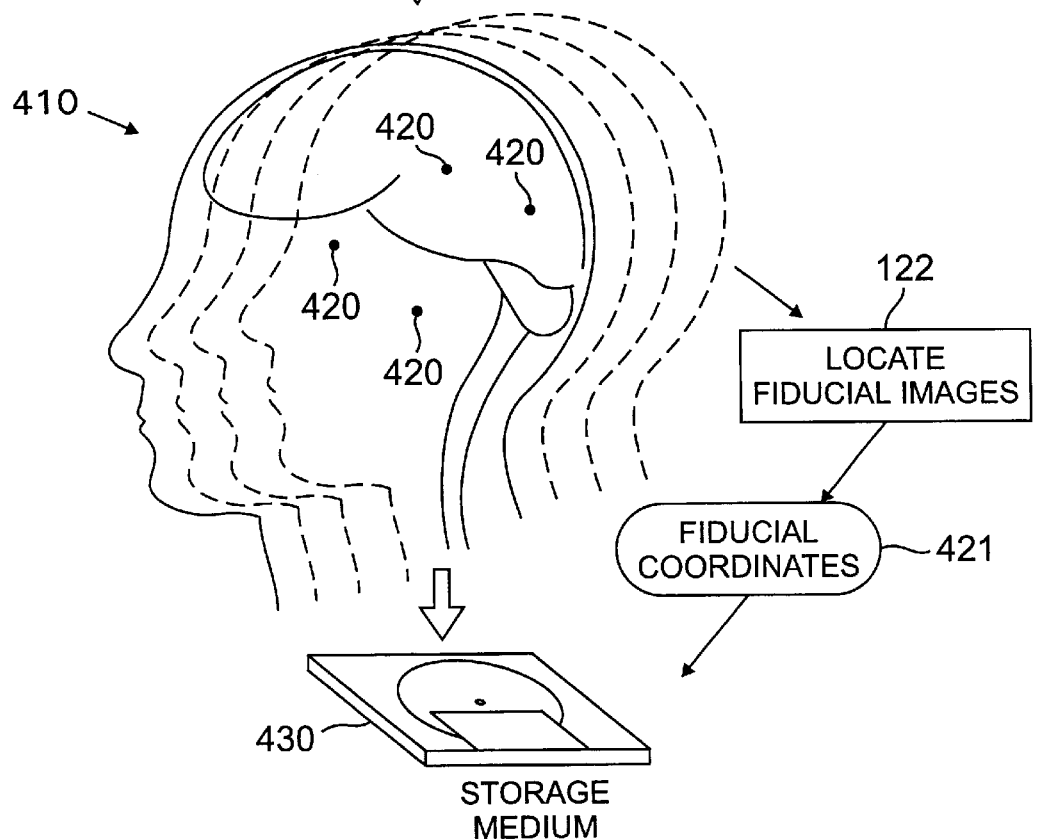

Referring to FIG. 4, MRI or CT scanner 400 is used to obtain a three-dimensional digitized image 410 of the head, for example, as a series of two-dimensional "slices" (step 115 in FIG. 1). In addition, a model or map of the surface of the skull can be made allowing, for instance, subsequent three-dimensional surface display of the skull. The fiducial scanning markers 340 produce fiducial images 420 at in image 410. Fiducial coordinates 421 of fiducial images 420 in the coordinate system of image 410 are determined, for example, by manually positioning a cursor at fiducial images 420 on a computer display. Image 410, along with the fiducial coordinates 421, are stored on a computer readable storage medium 430 for use during the subsequent surgical phase of the approach. Typically the image is stored as a series of two-dimensional images, each corresponding to a horizontal "slice" of the head.

After scanning, scanning MIRRF 310 is removed (FIG. 1, step 120), and threaded inserts 220 are left in place. Antibiotic ointment can be applied and the patient is either discharged or sent to the operating room.

Also after scanning, a surgeon determines the location of a target point within the brain and an entry point through the skull (FIG. 1, step 125). A planned surgical trajectory is then determined as the line joining the entry point and the target point. The surgeon plans the trajectory using a computer display of image 410 which provides, for example, a three-dimensional surface view, and sagittal, coronal, and axial planar views. This allows the surgeon, for example, to plan a trajectory that avoids critical structures in the brain. The target and entry points, and the trajectory are stored along with the image on storage medium 430.

Other than an optional fixture validation (FIG. 1, step 130), all the preoperative steps are complete at this point.

Surgical Phase

Figure 5:
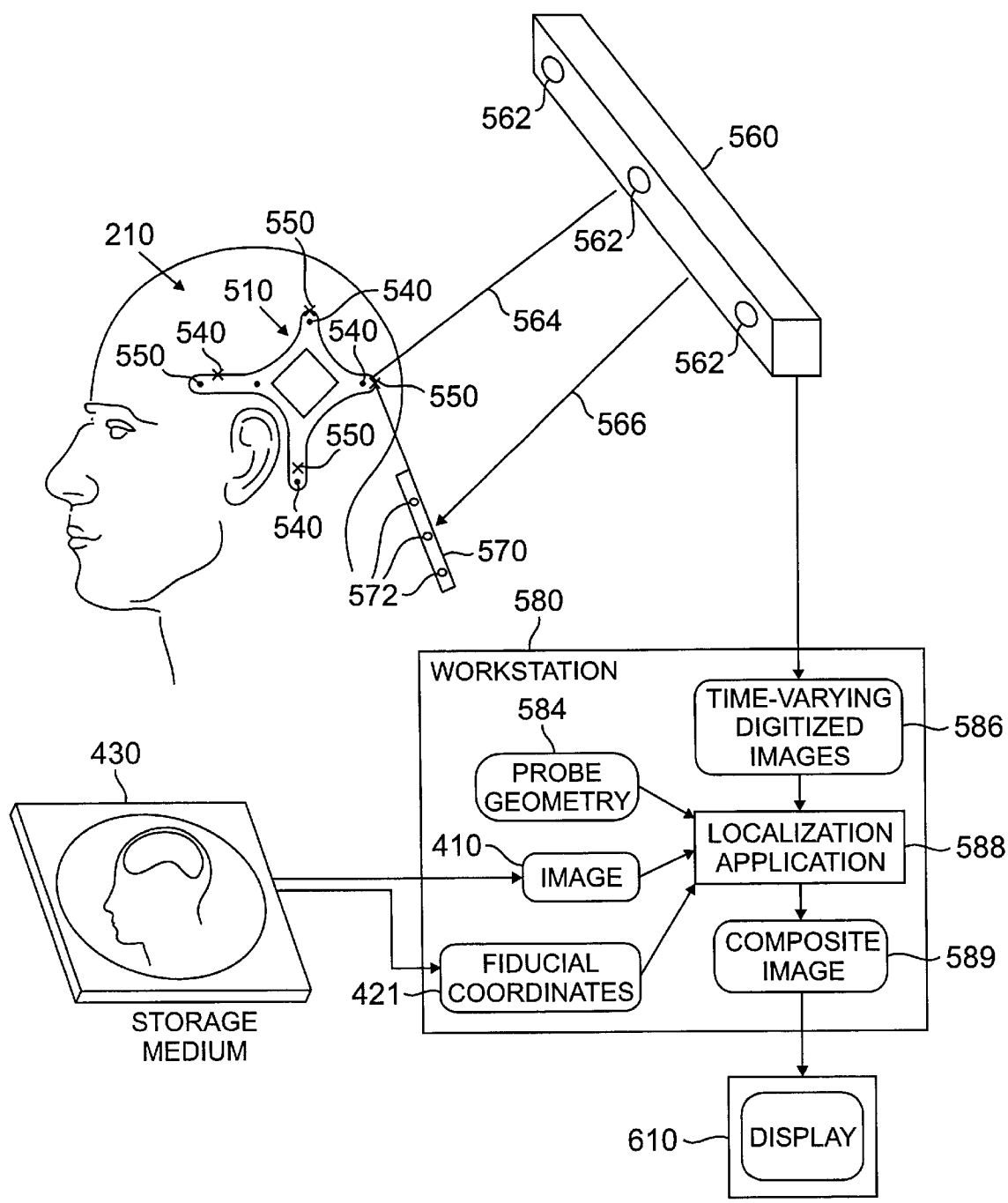
FIG. 5 is a head with a tracking MIRRF attached and a cranial probe being tracked using a camera array.

Referring to FIG. 5, the surgical phase of the procedure begins by attaching a tracking MIRRF 510 to threaded inserts 220 (not shown) that remained implanted in the patient's skull after scanning MIRRF 310 was previously removed. Tracking MIRRF 510 has a very similar structure to scanning MIRRF 310. Tracking MIRRF 510 includes fiducial divots 540 at the centers of locations corresponding to fiducial markers 340 (shown in FIGS. 3 and 4). Four tracking LEDs 550 are also attached to tracking MIRRF 510. Since tracking MIRRF 510 is rigid, the geometric relationship between tracking LEDs 550 and fiducial divots 540 is fixed and can be determined beforehand and verified in a subsequent verification step, or can be unknown and determined in a subsequent registration step. Preferably, tracking MIRRF 510 is made of a material that is lightweight and can be autoclaved, such as Radel.

After attaching tracking MIRRF 510 to the patient's skull, the patient can be comfortably placed in an awake, possibly lightly sedated, state in an operating room chair, which is similar to a dental chair. The patient is allowed to recline in an essentially unrestrained manner in the operating room chair in a semi-sitting position. Alternatively, at the surgeon's prerogative and if appropriate, general anesthesia can be administered to the patient.

Referring still to FIG. 5, a camera array 560 provides time-varying digitized images 586 to a localization application 588 executing on a computer workstation 580. The patient can be free to move relative to camera array 560 and relative to the operating room chair, and camera array 560 can be free to move relative to the patient and relative to the operating room chair. Camera array 560 includes three CCD cameras 562 positioned in a fixed configuration relative to one another. Alternatively, two cameras, which are sufficient for three dimensional localization, or more than three cameras, which may provide greater accuracy, can be used. Each camera 562 in camera array 560 produces one time-varying image. Each tracking LED 550 on tracking MIRRF 510 is powered and emits infra-red illumination which is seen as a bright point in each of time-varying digitized images 586. Based on the relative coordinates of the bright points in images 586 from each camera 562 of camera array 560 localization application 588 computes the position (i.e., the coordinates) of tracking LEDs 550 in the coordinate system of camera array 560. Using the positions of multiple tracking LEDs 550, the location and orientation of tracking MIRRF 510 can be computed by localization application 588. Tracking of MIRRF coordinates 510 is illustrated schematically by line 564.

A cranial probe 570, including three probe LEDs 572 attached along its length, is also tracked using camera array 560 and localization application 588. Based on the coordinates of the images of probe LEDs 572 in images 586 and probe geometry 584, localization application 588 computes the position and orientation of probe 570 in the coordinate system of camera array 560.

Registration

Using cranial probe 570, the surgeon then carries out a registration step (FIG. 1, step 140). In this registration step, the surgeon first locates the fiducial points in the image. Then he touches the tip of probe 570 to each of fiducial divots 540 in tracking MIRRF 510 in turn, indicating to localization application 588 when he is touching each of the divots. Localization application 588 then computes a three-dimensional conformal registration (map) between image 410 and the coordinate system of tracking MIRRF 510.

Note that if the geometric relationship of tracking LEDs 550 and fiducial divots 540 is known to localization application 588, for example using a previously calibrated MIRRF, the coordinates of the fiducial divots can be computed from the coordinates of the tracking LEDs, which in turn can be computed from the locations of the fiducial images in the camera images. The step of touching the divots can be omitted in this case, or used to verify the computed coordinates of fiducial divots.

Having computed the conformal mapping, localization application 588 continuously combines image 410 and a synthesized image of probe 570 to form a composite image 599 that combines the scanned image with the synthesized image of the probe. Composite image 599 is shown on a computer display 610 which includes a three-dimensional surface display.

Figure 6:
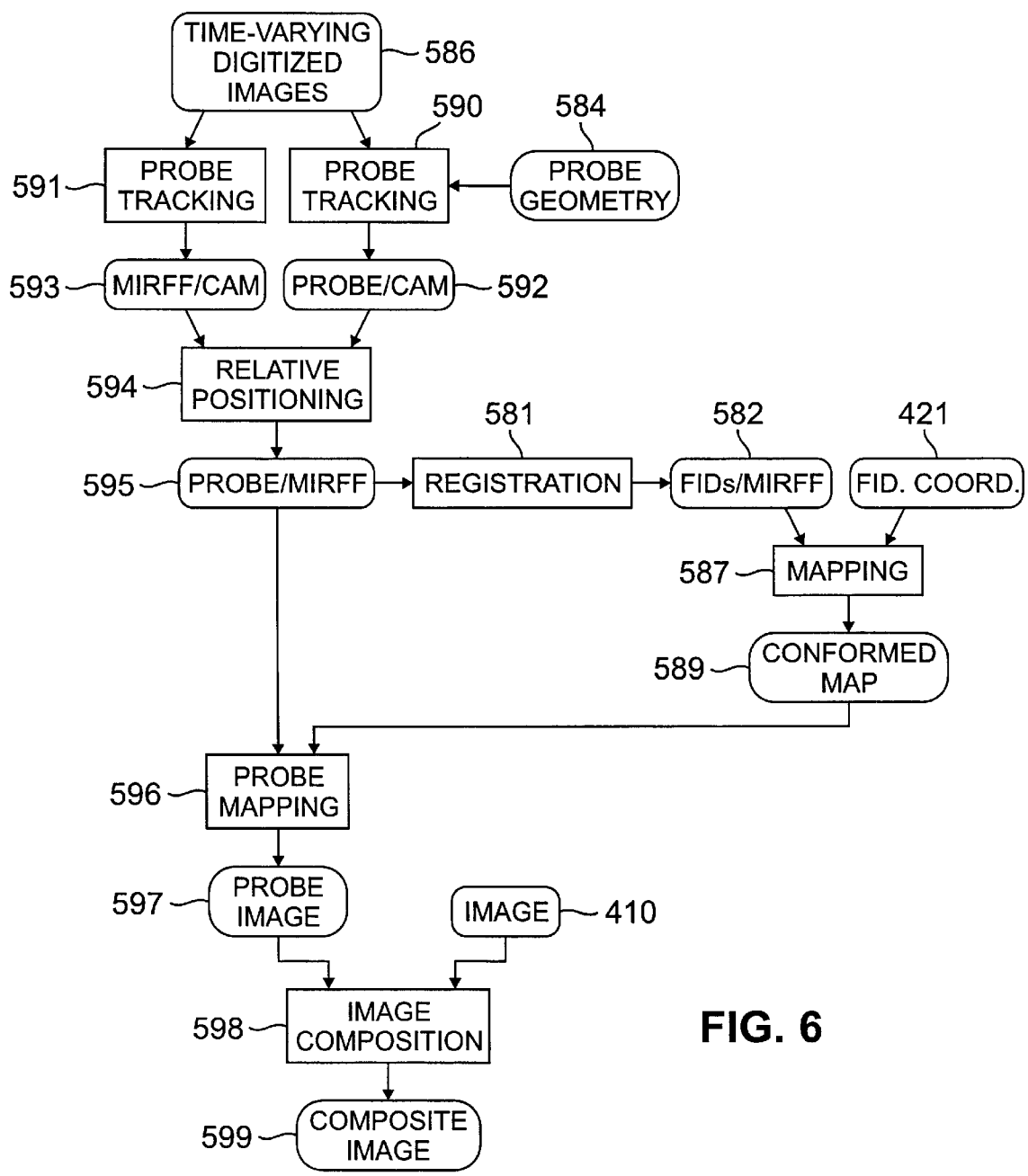
FIG. 6 is a dataflow diagram for computation of a composite image including a synthesized image of a probe.

Referring to FIG. 6, the registration and image composition functions performed by localization application 588 involves a series of data processing stages. As shown in FIG. 5, time-varying digitized images 586 are provided to localization application 588 from camera array 560. Referring to FIG. 6, time-varying digitized images 586 are input to MIRRF tracking 591, a processing stage of localization application 588, which tracks tracking LEDs 550 on tracking MIRRF 510 and produces "MIRRF/cam" 593, an orientation and location of tracking MIRRF 510 in the coordinate system of camera array 560. At the same time, probe tracking 590 tracks probe 570 and produces "probe/cam" 592, an orientation and location of probe 570 in the coordinate system of camera array 560. Probe tracking 590 makes use of probe geometry 584 which specifies the geometric relationship between the tip of the probe 570 and probe LEDs 572. The next stage of localization application 588, relative positioning 594 inputs MIRRF/cam 593 and probe/cam 592 and produces "probe/MIRRF" 595, the position and orientation of probe 570 in the coordinate system of tracking MIRRF 510. When the surgeon touches fiducial divots 540, registration 581 takes the location information from probe/MIRRF 595 and records it in "fids/MIRRF" 582, the coordinates of fiducial divots 540 in the coordinate system of tracking MIRRF 510. Fiducial coordinates 421, the coordinates of fiducial images 420 in the coordinate system of image 410, are provided to localization application 588, along with image 410, from storage medium 430. Mapping 587 includes matching of corresponding coordinates in fids/MIRRF 582 and fiducial coordinates 421 and forming a conformal map 589 between the coordinate system of image 410 and the coordinate system of tracking MIRRF 510. Conformal map 589 includes the quantities required to transform any three-dimensional coordinate in the coordinate system of tracking MIRRF 510 into a three-dimensional coordinate in the coordinate system of image 410. These quantities correspond, in general, to a rotation, scaling, and translation of points in the coordinate system of tracking MIRRF 510 to determine the corresponding points in the coordinate system of image 410.

Referring still to FIG. 6, the next stage of localization application 588, probe mapping 596, takes the continually updated probe coordinates, probe/MIRRF 595, and conformal map 589, and computes probe/image 597, the coordinates of probe 570 in the coordinate system of image 410. Then, image composition 598 combines image 410 and a synthesized image of probe 570 to form composite image 599.

Composite image 599 typically includes a three-dimensional surface view and three orthogonal planar views. The orthogonal planar views can correspond to the three standard orientations, sagittal, coronal, and axial planes, for instance passing through the planned target point. More typically, three planar views of a navigational view that is determined by the planned entry and target points are included in composite image 599. The tip of the probe is displayed as an orthogonal projection onto the planes of the planar views, and as a point in an appropriate geometric relationship in the three-dimensional surface view. The orientation of the probe can be displayed using a line passing through the tip of the probe and displayed as a orthogonal projection onto navigational planes 1 and 2 of the navigational view, and as a point of intersection on the bird's eye view of the navigational view.

If the geometric relationships of the fiducial points, fids/ MIRRF 582, the coordinates of fiducial divots 540 does not match the geometric relationships of fiducial coordinates 421, then an error in placing probe 570 during the registration procedure may have occurred. If such an error is detected, conformal mapping 589 is not computed, a warning is provided to the surgeon, and the surgeon must perform the registration procedure again. Furthermore, if the geometric relationships between fiducial divots 540 is known through prior measurement or calibration, registration errors and errors locating fiducial points 420 in image 410 can also be detected.

Figure 7:
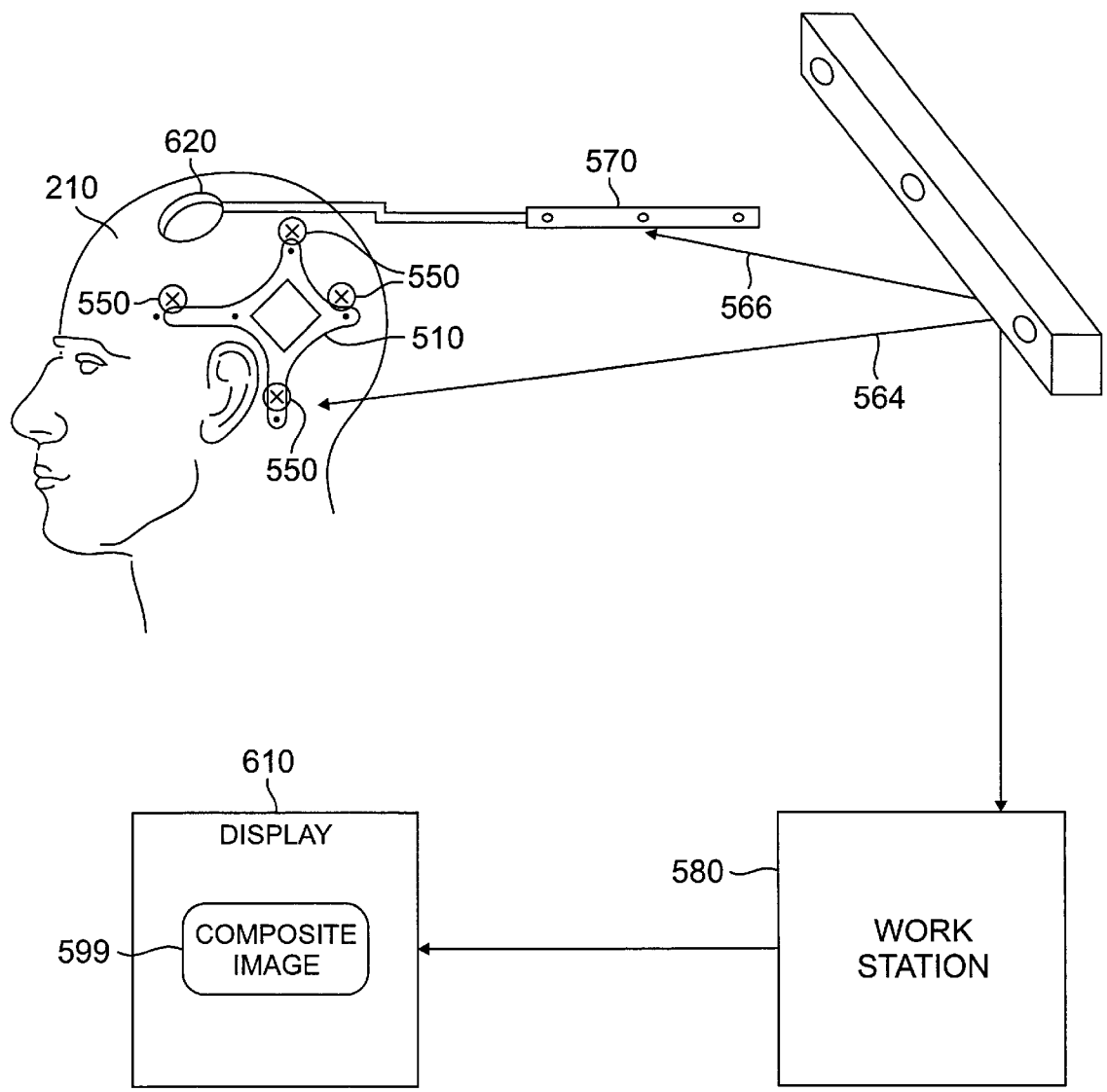
FIG. 7 illustrates locating a planned entry point using the tracked cranial probe and a computer display.

Referring to FIG. 7, a cranial probe 570 is used to determine an actual entry point. A computer display 610 shows composite image 599, which includes a three-dimensional surface view and three planar views of a navigational view determined by the planned entry and target points.

Figure 8:
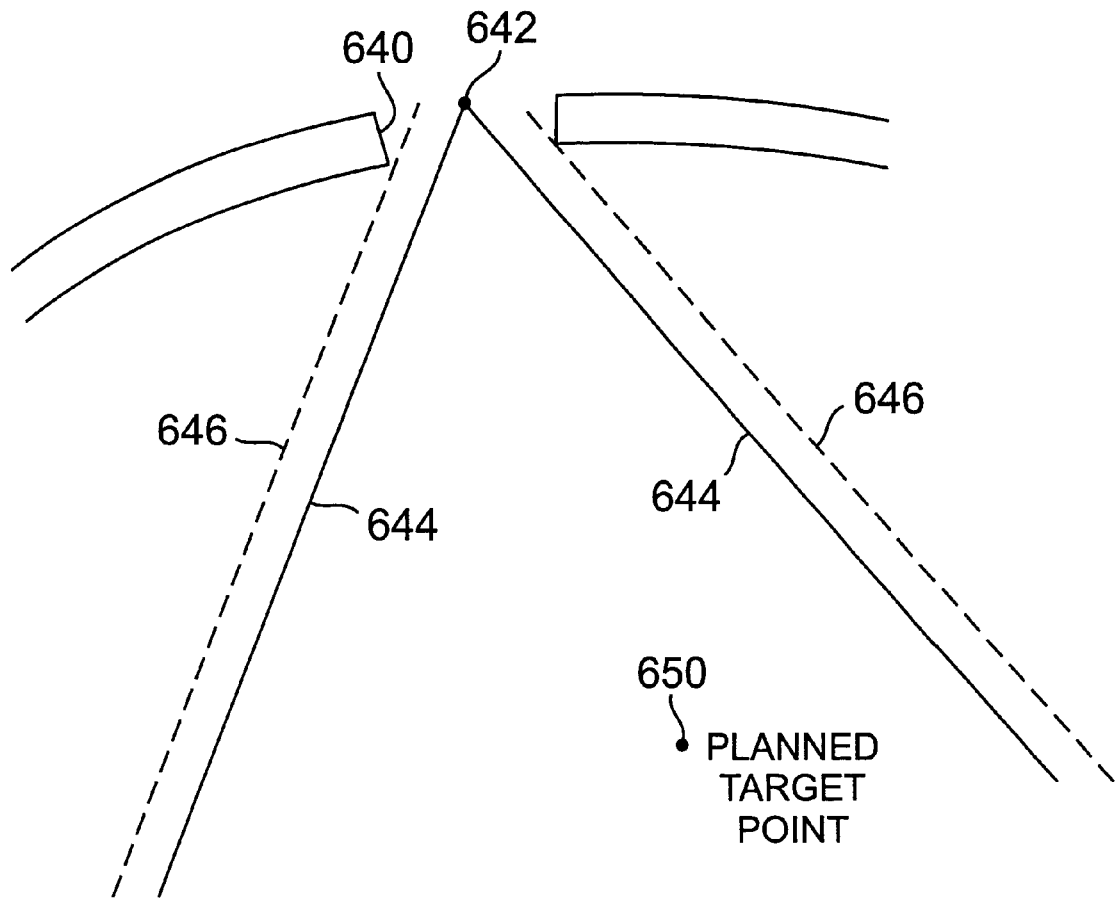
FIG. 8 is a display of a virtual burr hole and accessible cone of orientations.

Referring to FIG. 8, a virtual burr hole 640 is displayed in the planar views of navigational view at the probe location 642 of cranial probe 570. In addition, the range of adjustable orientations of a guidance fixture that would be attached at probe location 642 is displayed as a cone 644, and the extent of effects of x-y adjustment of the guidance fixture is displayed as a second cone 646. Display of cones 644 and 646 allows the surgeon to verify that planned target point 650 is accessible in the range of adjustments of a guidance fixture attached at probe location 642.

When the surgeon has located an entry point 620 on the skull, he marks the entry point as the desired center point of attachment of a guidance fixture that will be used during the surgical phase of the procedure.

The patient then has a small area of the head shaved and draped off. A 2 to 4 cm linear incision is made over entry point 620 after local anesthesia is administered. The location of entry point 620 is then reconfirmed using cranial probe 570 after the incision is made. An approximately 1 cm burr hole (not shown in FIG. 7) is then drilled through the skull at entry point 620 (FIG. 1, step 150). The surgeon opens the dura under the burr hole and visually inspects the area to determine that no critical structures, such as a blood vessel, are located directly under the burr hole. If the location of the burr hole is found to be unacceptable, a new entry point can be planned and return to the step of locating the entry point (FIG. 1, step 145).

Attaching the Guidance Fixture

Figure 9:
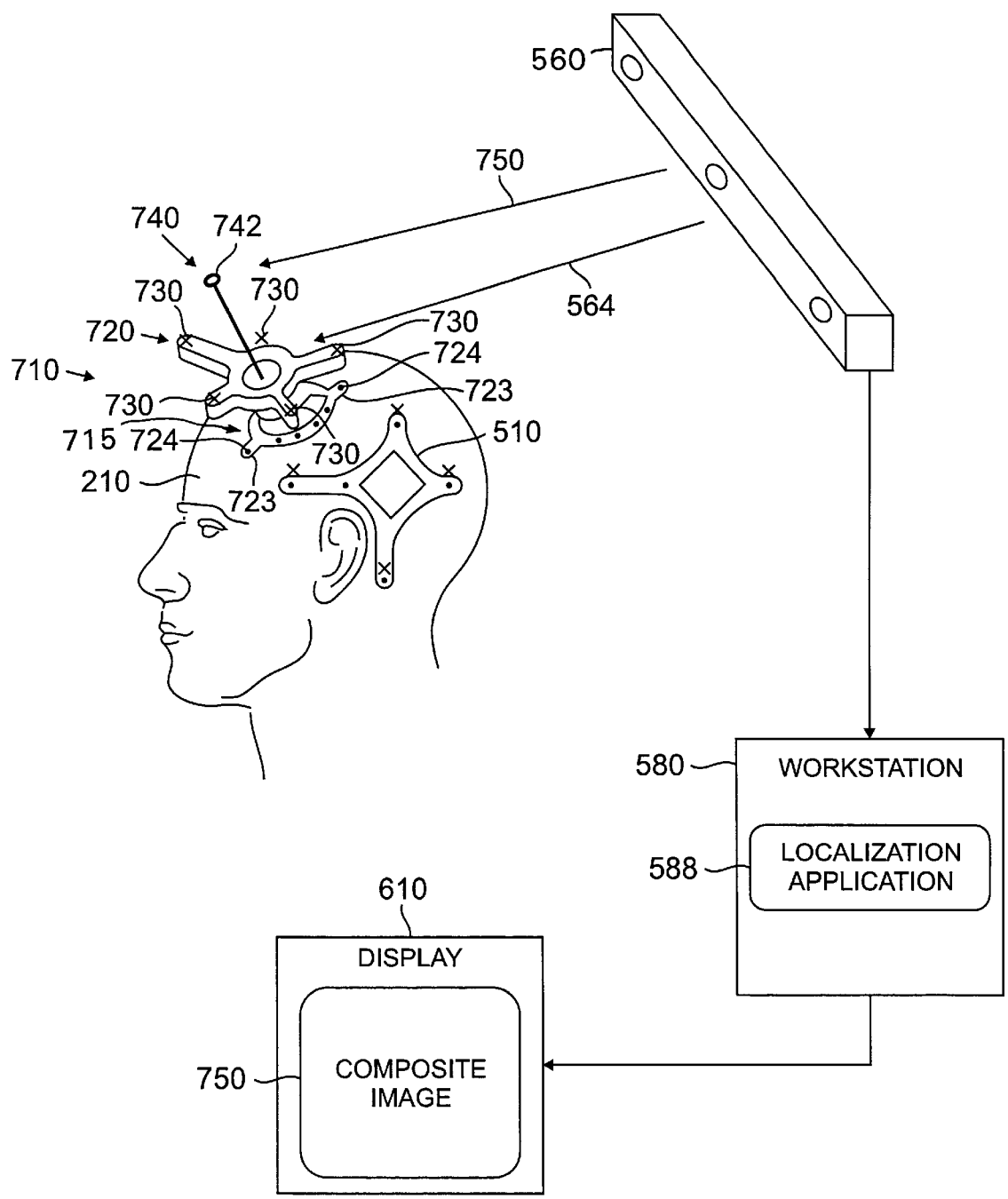
FIG. 9 is a head with a tracking MIRRF and a guidance fixture attached being tracked using a camera array.

Referring to FIG. 9, having drilled the burr hole, the surgeon next attaches a guidance fixture 710 to the skull (FIG. 1, step 155). (Note that an optional instrument drive can also included in the guidance fixture but is not shown in FIG. 9.) As is described more fully below, guidance fixture 710 includes a base platter 720 on which platter LEDs 730 are attached. Base platter 720 is attached to an adjustable base 715, which is in turn attached to the skull. The orientation of a line normal to base platter 720 is adjustable within a cone forming a solid angle of approximately 45 degrees. After attaching guidance fixture 710 the surgeon adjusts the orientation of base platter 720 (FIG. 1, step 170; note that optional steps 160 and 165 are described below). A surgical instrument 740, including an instrument LED 742 fixed relative to the instrument, passes through guidance fixture 710. Surgical instrument 740 is constrained to follow a fixed trajectory perpendicular to and through a central opening through adjusted base platter 720. Workstation 580 tracks the location and orientation of base platter 720, and the displacement of surgical instrument 740, indicated schematically by lines 564 and 750 respectively, and computes the position of surgical instrument 740 in the coordinate system of image 410. Workstation 580 continually displays on display 610 a composite image 750 including a navigational view of image 410 showing the position and orientation of surgical instrument 740. The surgeon uses the visual feedback on display 610 to position surgical instrument 740 along the constrained trajectory. Note that during this time, the patient is not necessarily immobilized. Both the patient and camera array 560 can move and, as long as platter LEDs 730 and instrument LED 742 are visible to camera array 560 at an appropriate distance and orientation, workstation 580 can maintain a continuously updated display.

Figure 10:
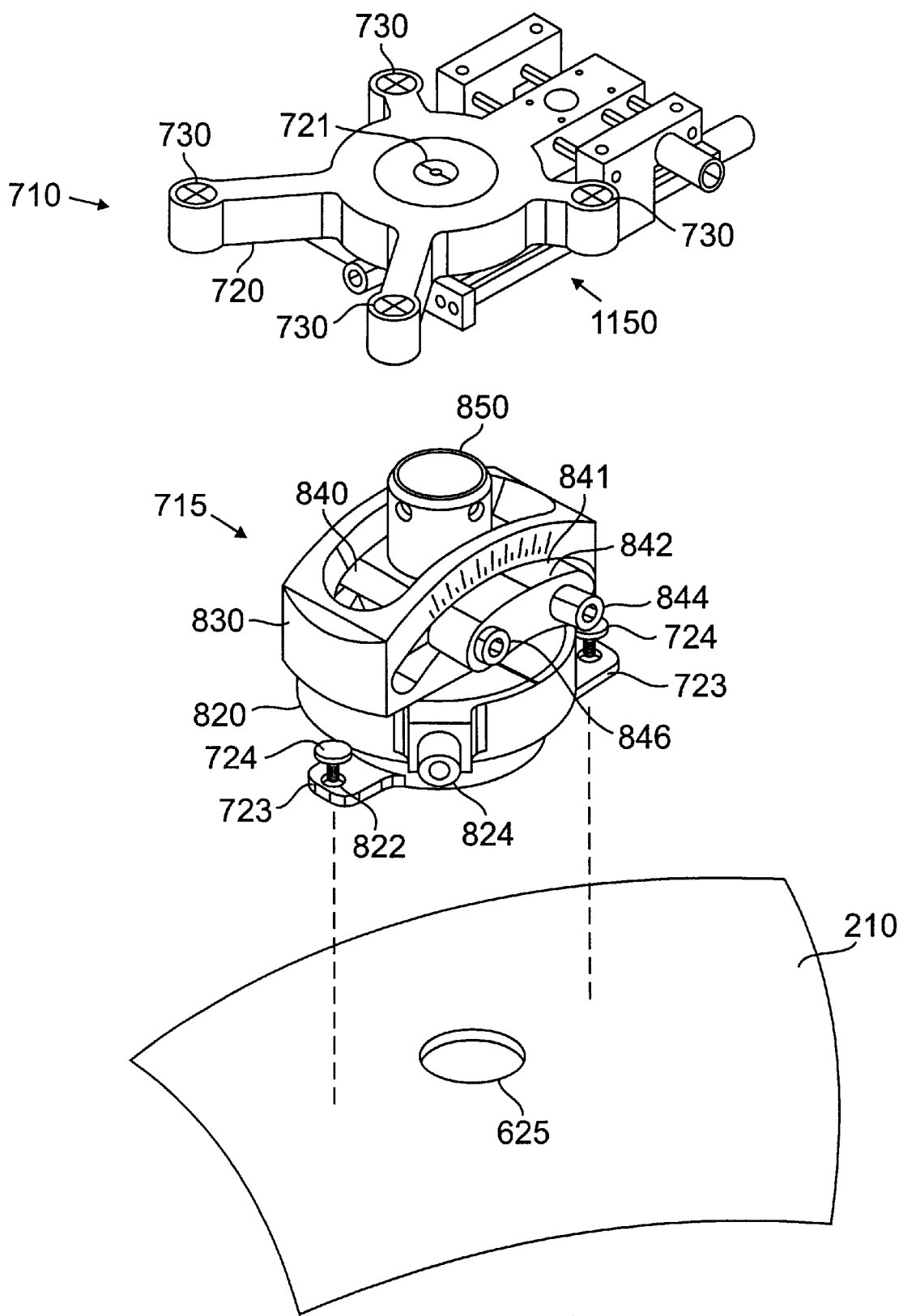
FIG. 10 is a view of a base platter and an adjustable base of a guidance fixture.

Referring to FIG. 10, guidance fixture 710 includes base platter 720 and adjustable base 715. In use, base platter 720 is attached to an entry column 850 (through an x-y positioning table 1150, described fully below) which is held in adjustable base 715. The orientation of entry column 850 can be adjusted relative to skull 210 using separate rotation and pivoting motions, as described below. Referring also to the exploded view of adjustable base 715 shown in FIG. 11, guidance base 715 includes a mounting base 820, which is rigidly attached to the skull during an operation using screws through mounting holes 822. Mounting holes 822 pass through mounting tabs 723 as well as through the inside of the mounting base 820. Mounting tabs 823 are pliable to allow them to conform to the skull. As mounting base 820 may be distorted in being mounted to the skull, it can be designed to be disposable. Mounting base 820 has a cylindrical opening which accepts a rotating collar 830. A rotation locking screw 824 in mounting base 820, when tightened, locks rotating collar 830 in place and prevents its movement within the mounting base. Entry column 850 is held within rotating collar 830 by a pivoting collar 840. Pivoting collar 840 slides in an arc-shaped pivoting guide 841 within rotating collar 830. When rotated, a pivoting locking knob 846 prevents pivoting collar 840 from sliding by drawing a collar clamp 842 against pivoting collar 840 using a threaded rod 920. When rotated, a pivoting adjustment knob 844 slides pivoting collar 840 along pivoting guide 841.

Referring again to FIG. 11, mounting base 820 includes mounting holes 822 drilled through mounting tabs 723 (one tab is not visible on the side opposite the visible one), as well as through the inside of mounting base 820. Mounting base 820 includes a threaded hole 922 within which rotation locking screw 824 turns. Rotation locking screw 824 mates with a recessed channel 923 in rotating collar 830, thereby preventing rotation of rotating collar 830 and also preventing rotating collar 830 from lifting off mounting base 820.

Entry column 850 includes a cylindrical portion 913 and a spherical portion 914 at one end. Spherical portion 914 mates with a spherical socket 916 in the bottom of rotating collar 830. When mated, entry column 850 can pivot within rotating collar 830. Entry column 850 also has opposing groves 910 which mate with protrusions 912 on the inside of the circular opening in pivoting collar 840. Entry column 850 passes through the circular opening, and protrusions 912 mate with groves 910. When assembled, the mated groves and protrusions hold the spherical portion 914 of entry column 850 against spherical socket 916 in the bottom of rotating collar 830.

The position of pivoting collar 840 within pivoting guide 841 is adjusted by turning pivoting adjustment knob 844 and tightened in place by rotating pivoting tightening knob 846. Pivoting adjustment knob 844 attaches to a pivoting adjustment rod 930 which passes through collar clamp 842 and the main portion of pivoting collar 840 to a rack and pinion mechanism. A pinion 931 is attached to the end pivoting adjustment rod 930. Pinion 931 mates with an arc-shaped rack 932 which attaches to rotating collar 830 using three screws 934. Rotation of pivoting adjustment knob 844 rotates pivoting adjustment rod 930 and pinion 931, which then slides pivoting collar 840 in pivoting guide 841. Rotating pivoting locking knob 846 locks pivoting collar 840 rigidly to rotating collar 830. Tightening both rotation locking screw 824 and pivoting locking knob 846 fixes the orientation of entry column 850 relative to mounting base 820.

Referring to FIG. 10, the procedure for attaching and adjusting guidance fixture 710 (FIG. 1, steps 155 through 170) is carried out as follows. Mounting base 820 is attached in a temporary fashion over burr hole 625. While attaching the base, mounting tabs 723 are conformed to the shape of the skull 210 and secured to the skull an orientation generally directed towards the target using three or more titanium bone screws 724 passing through mounting holes 822 through mounting tabs 723 and through the interior of the mounting base.

After mounting base 820 is attached to skull 210, the remainder of guidance base 715 is attached to mounting base 820. In particular, rotating collar 830, with entry column 850 already attached, and adjusted to be centered (oriented along the central axis of guidance base 715) is inserted in mounting base 820 and rotation locking screw 824 is tightened to mate with recessed channel 923.

After guidance base 715 is attached to skull 210, the remainder of guidance fixture 710 is attached to guidance base 715. In FIG. 10, the drive assembly, which is already attached to base platter 720 at the time base platter 720 is attached to guidance base 715 is not shown. Base platter 720 is attached to entry column 850 via an x-y positioning table 1150 (described below). During the alignment phase in which the orientation of guidance base 715 is adjusted, x-y positioning table 1150 remains centered.

During a surgical procedure, surgical instrument 740 is passed through a central opening 721 of base platter 720 and through entry column 850 into the brain. During the alignment phase in which x-y table 1150 is centered, a line along the trajectory surgical instrument 740 would follow passes along the central axis of entry column 850. Adjusting the orientation of guidance base 715 adjusts this trajectory. In all orientations, the trajectory passes through a single point on the central axis of guidance base 715 near the surface of the skull. If the guidance base is exactly mounted over the planned entry point, this single point is the planned entry point. More typically, the point is slightly displaced from the planned entry point due to mounting inaccuracies.

Referring again to FIG. 9, platter LEDs 730 on base platter 720 are sensed by camera array 560, and the location and orientation of base platter 720 in the coordinate system of image 410 is computed by localization application 588 executing on computer workstation 580. Localization application 588 computes the location and orientation of base platter 720 using the known geometry of the base platter relative to platter LEDs 730.

Figure 12:
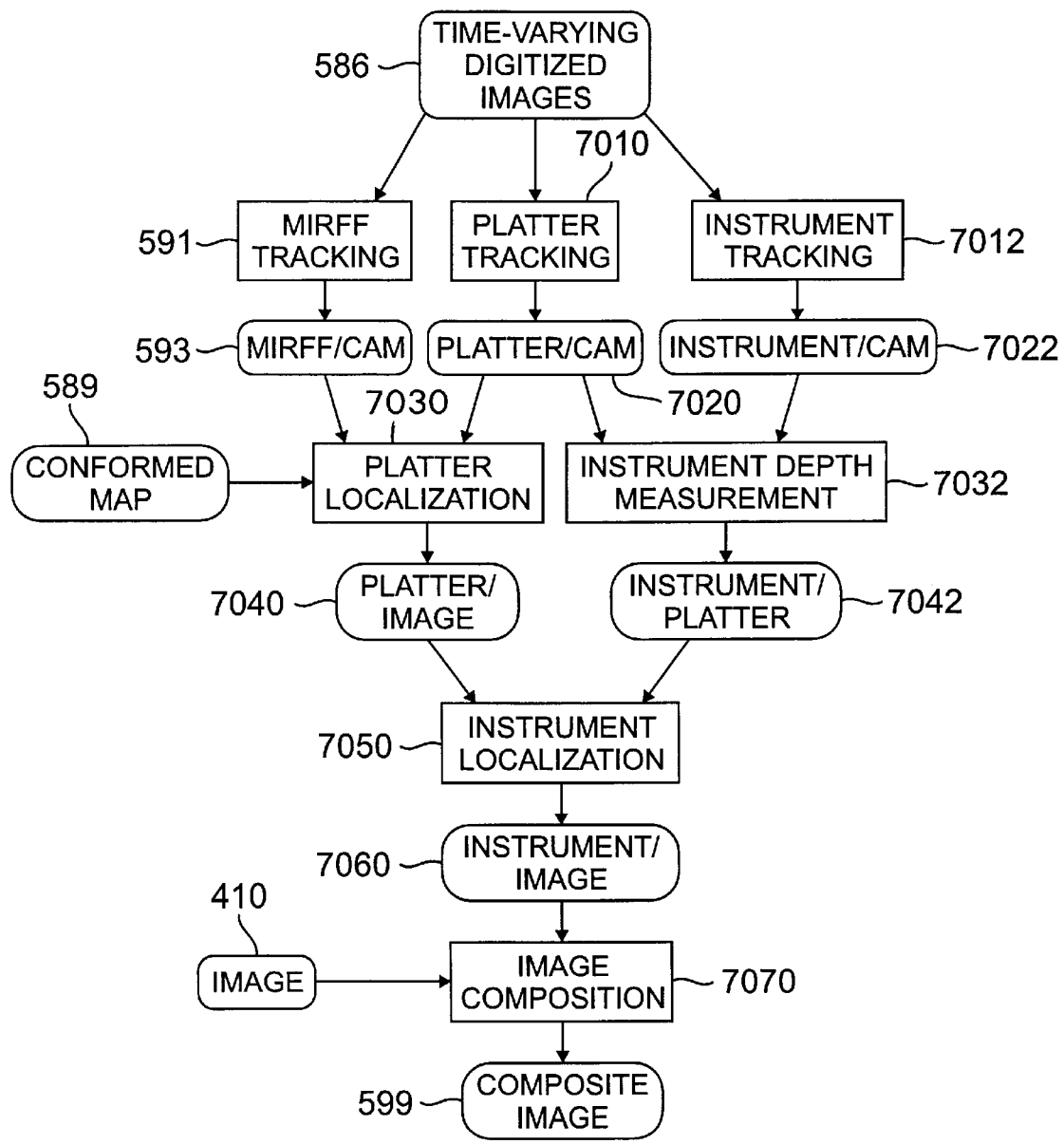
FIG. 12 is a dataflow diagram for computation of a composite image including a synthesized image of a surgical instrument.

Referring to FIG. 12, localization application 588 computes composite image 750 (FIG. 9) in a series of data transformations. Time-varying digitized images 586 are passed to MIRRF tracking 591 as well as platter tracking 7010 and instrument tracking 7012. MIRRF tracking 591 produces "MIRRF/cam" 592, the position and orientation of tracking MIRRF 510 in the coordinate system of camera array 560. Platter tracking 7010 produces "platter/cam" 7020, the position and orientation of base platter 720. The instrument trajectory is at a known location and orientation relative to platter LEDs 730 on base platter 720, therefore the location and orientation of the instrument trajectory in the coordinate system of camera array 560 is also known. Instrument tracking 7012 produces instrument/cam 7022, the location of instrument LED 742 in the coordinate system of camera array 560. Platter localization 7030 uses conformal map 589, MIRRF/cam 593, and platter/cam 7020 to compute platter/image 7040, the location and orientation of base platter 720 in the coordinate system of image 410. Note that once guidance fixture 710 is attached and aligned, then base platter 720 no longer moves relative to the skull (other than due to adjustment of x-y table 1150) and therefore, platter/image 7040 can be fixed rather than continuously recomputed. Instrument depth measurement 7032 combines platter/cam 7020 and instrument/cam 7022 to compute instrument/platter 7042, the depth of penetration of the surgical instrument relative to the plane of base platter 720. Instrument depth measurement 7032 makes use of the known displacement of the tip of the instrument from instrument LED 742. Instrument localization 7050 takes platter/image 7040 and instrument/platter 7042 and computes instrument/image 7060, the location and orientation of the surgical instrument in the coordinate system of image 410. Finally, image composition 7070 combines image 410 with a synthesized image of the surgical instrument to generate a composite image 750.

Figure 13:
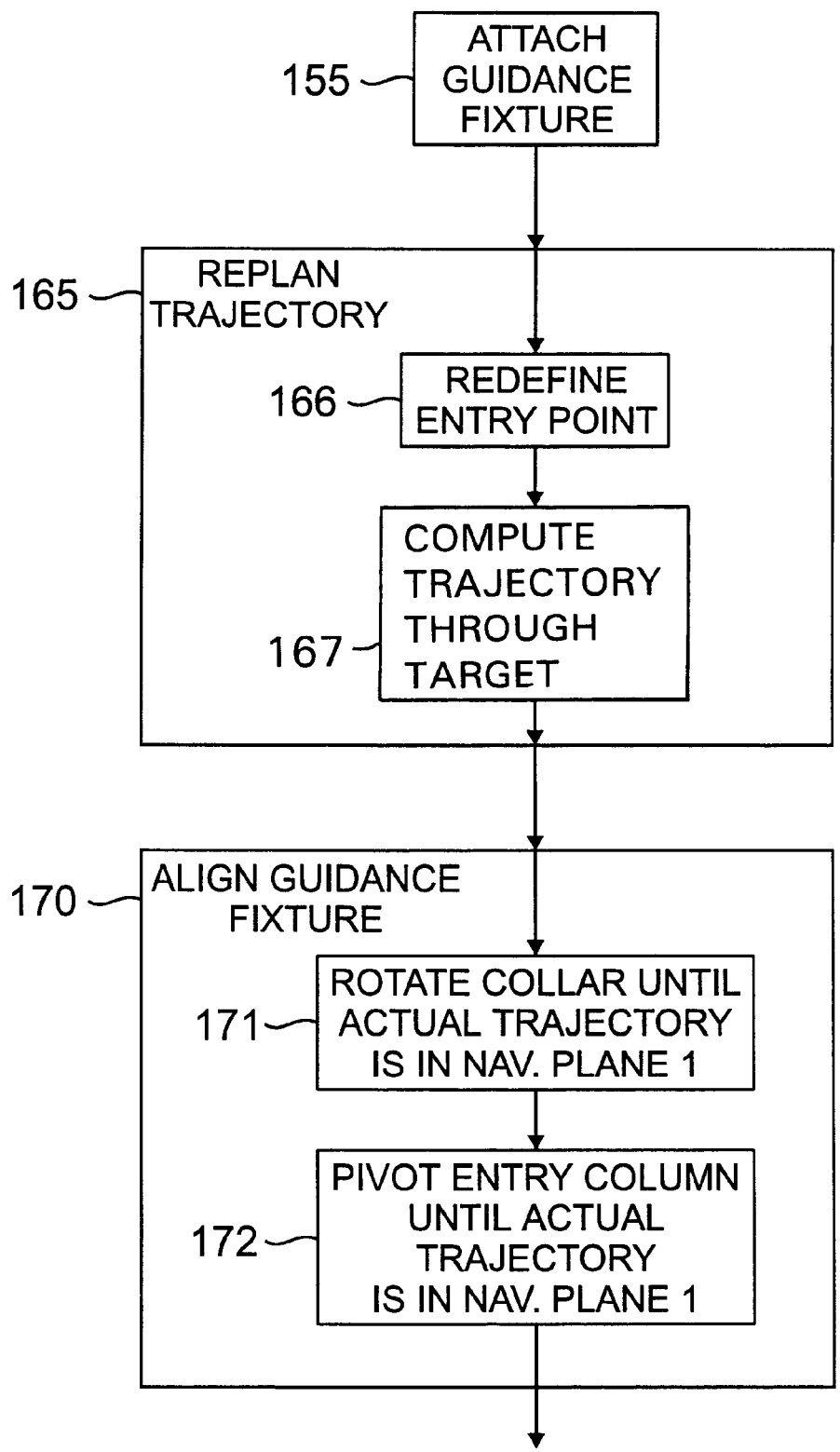
FIG. 13 is a detailed flowchart of trajectory replanning and fixture alignment.

Referring to FIG. 13, before aligning guidance fixture 710, the surgical trajectory is optionally replanned to go through the center of the actual mounted position of the guidance fixture, rather than the planned entry point (FIG. 1, step 165).

Figure 14A:
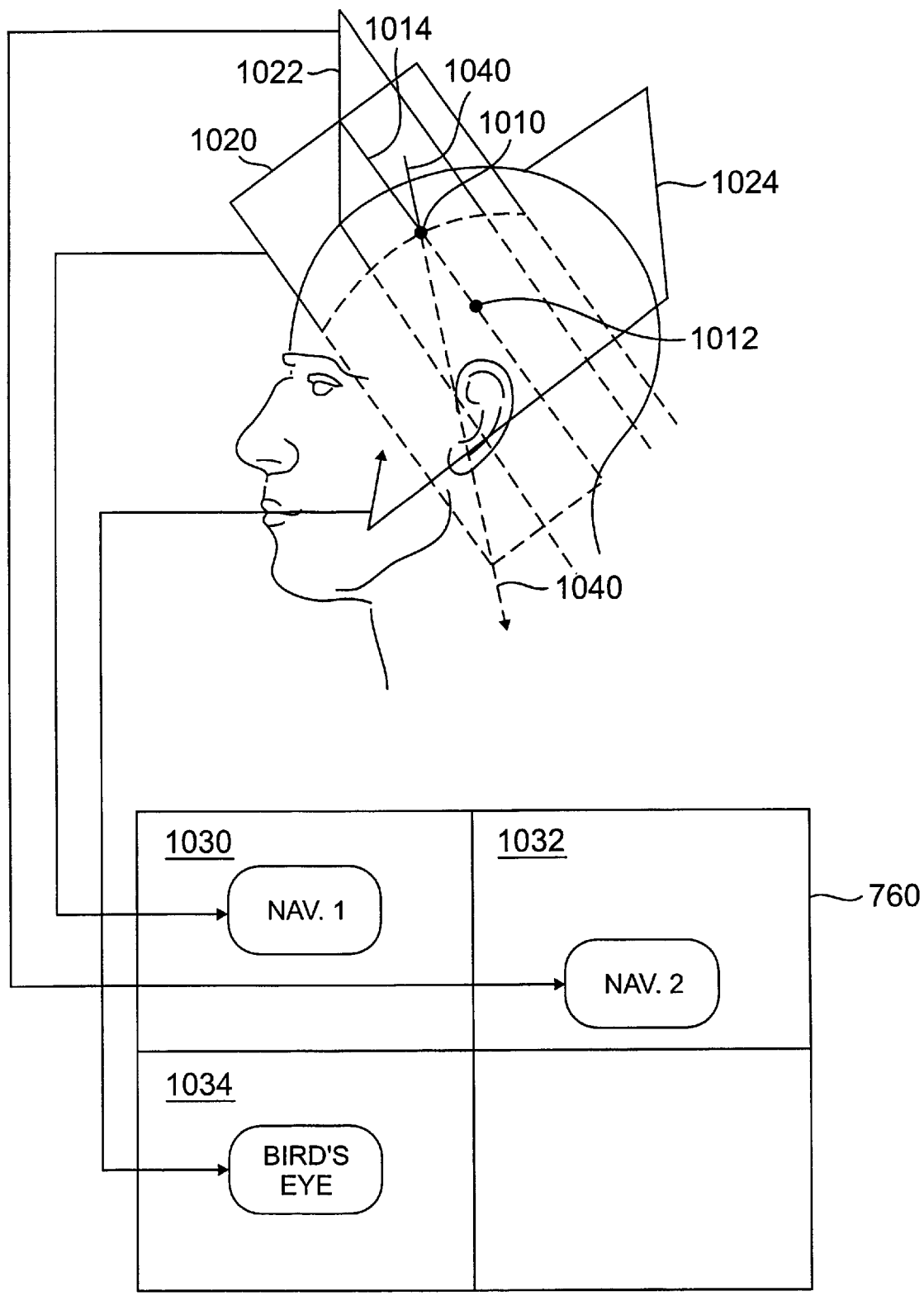
FIGS. 14a–c illustrate a navigational view display and corresponding planar segments through a body.
Figure 14B:
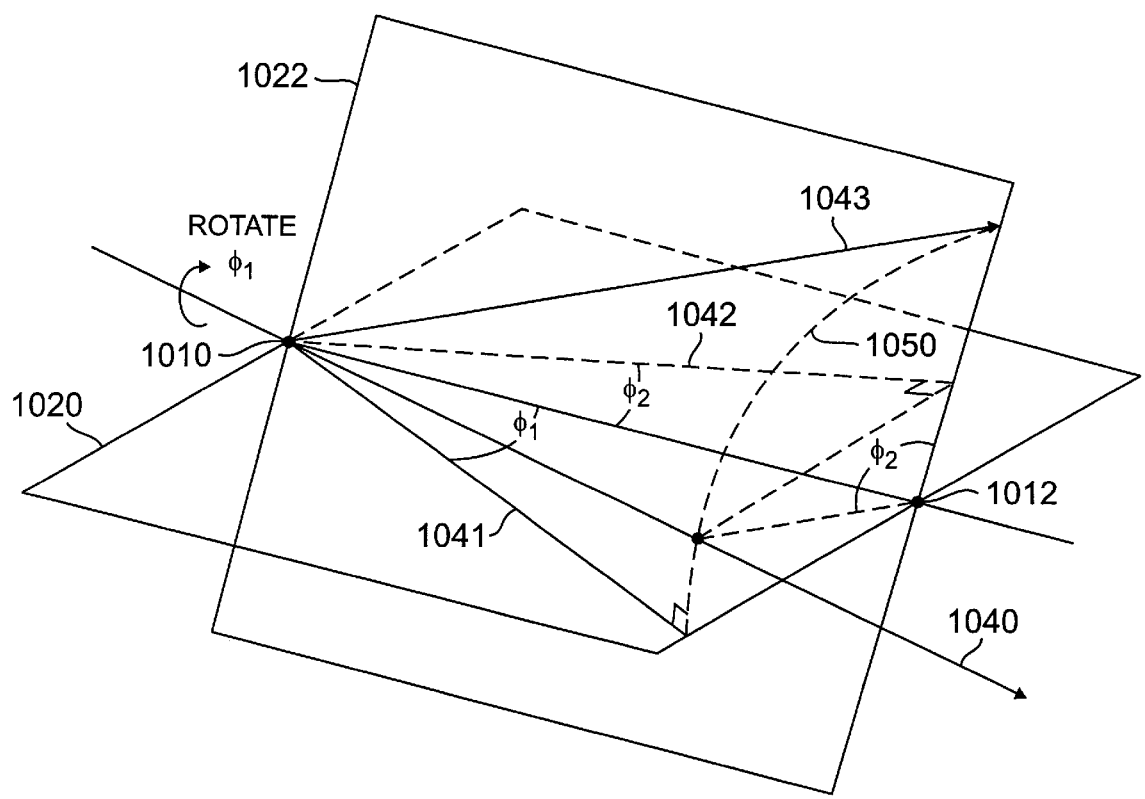
Figure 14C:
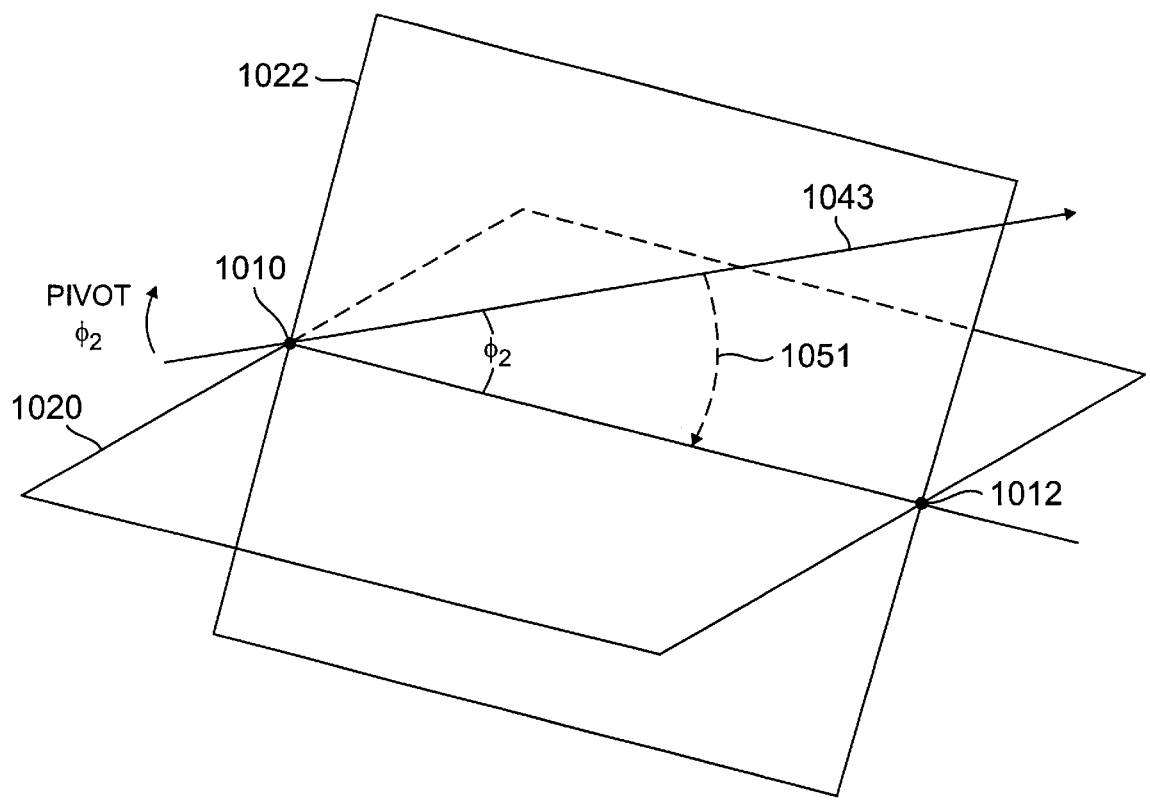

Aligning the Guidance Fixture The surgeon aligns guidance fixture 710 using visual feedback. Referring to FIGS. 14a–c, a navigational view indicating the trajectory of the surgical instrument is used. Referring to FIG. 14a, navigational planes 1020 and 1022 correspond to navigational planar views 1030 and 1032 respectively. Navigational planes 1020 and 1022 are orthogonal and their intersection forms a line passing through an entry point 1010 and a target point 1012. Bird's eye plane 1024, the third plane of the navigational view, is orthogonal to planes 1020 and 1024 and passes through target point 1012.

Referring to FIGS. 14b–c, navigational planes 1020 and 1024 are shown schematically, along with a line 1040 corresponding to the orientation of guidance fixture 710. The goal of the alignment procedure is to make line 1040 coincident with the intersection of planes 1020 and 1022. The alignment procedure is carried out in a series of two motions each of which is constrained to one degree of freedom. Initially, line 1040 is not generally coincident with either navigational plane. Prior to beginning the alignment procedure, the orientation of line 1040 is displayed as orthogonal projections, lines 1041 and 1042, on planes 1020 and 1022, respectively.

Figure 11:
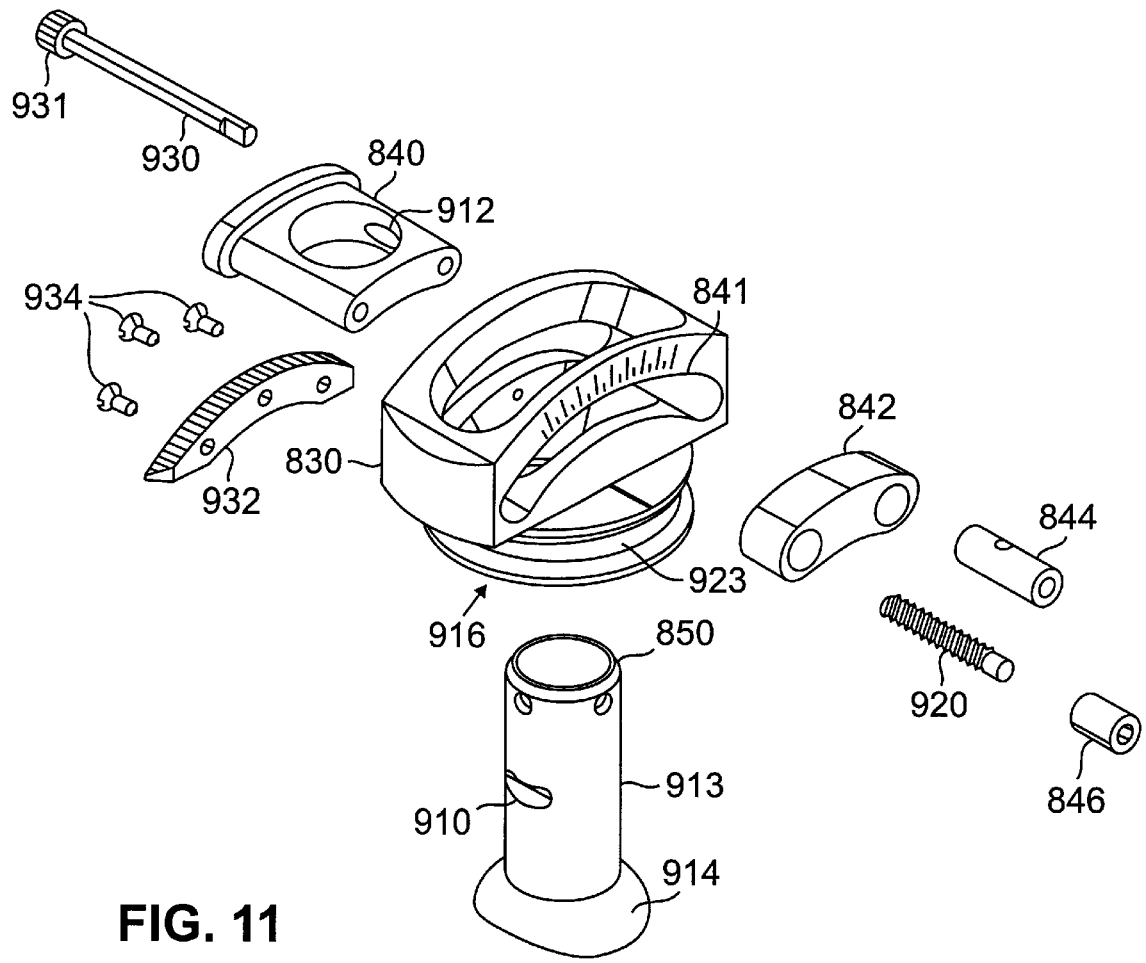
FIG. 11 is an exploded view of the adjustable base of a guidance fixture.
Figure 11:
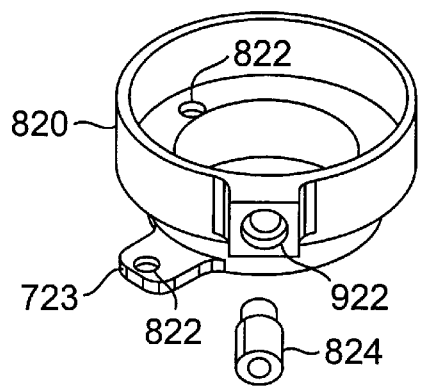

In the first alignment motion, rotating collar 830 is rotated within mounting base 820 (FIGS. 10 and 11). Referring to FIG. 14b, this rotation causes line 1040 to sweep out a portion of a cone, indicated diagrammatically by dashed arrow 1050. After rotation through an angle $\phi_1$, orientation line 1040 is in the direction of line 1043, which is coincident with plane 1022. During the rotation, the orthogonal projection line 1041 of line 1040 in plane 1020 forms a smaller and smaller angle $\theta_1$, with the desired orientation in plane 1020, while the angle $\theta_2$ between the orthogonal projection line 1042 in plane 1022 and the desired orientation in plane 1022 increases, ultimately to $\phi_2$ when line 1040 is coincident with plane 1022.

Referring to FIG. 14c, the second alignment motion reduces the angle $\phi_2$ while maintaining the coincidence of the orientation line and plane 1022. This motion corresponds to sliding pivoting collar 840 within rotating collar 830 (FIGS. 8 and 9). Alignment is achieved when angle $\phi_2$ is zero, that is, the orientation line 1040 is coincident with the intersection of planes 1020 and 1022.

At this point, after tightening the locking knobs on guidance fixture 710, base platter 720 is firmly fixed to the skull, in an orientation and location that constrains a surgical instrument passing through it to pass along the replanned trajectory to the planned target point in the head.

Figure 15A:
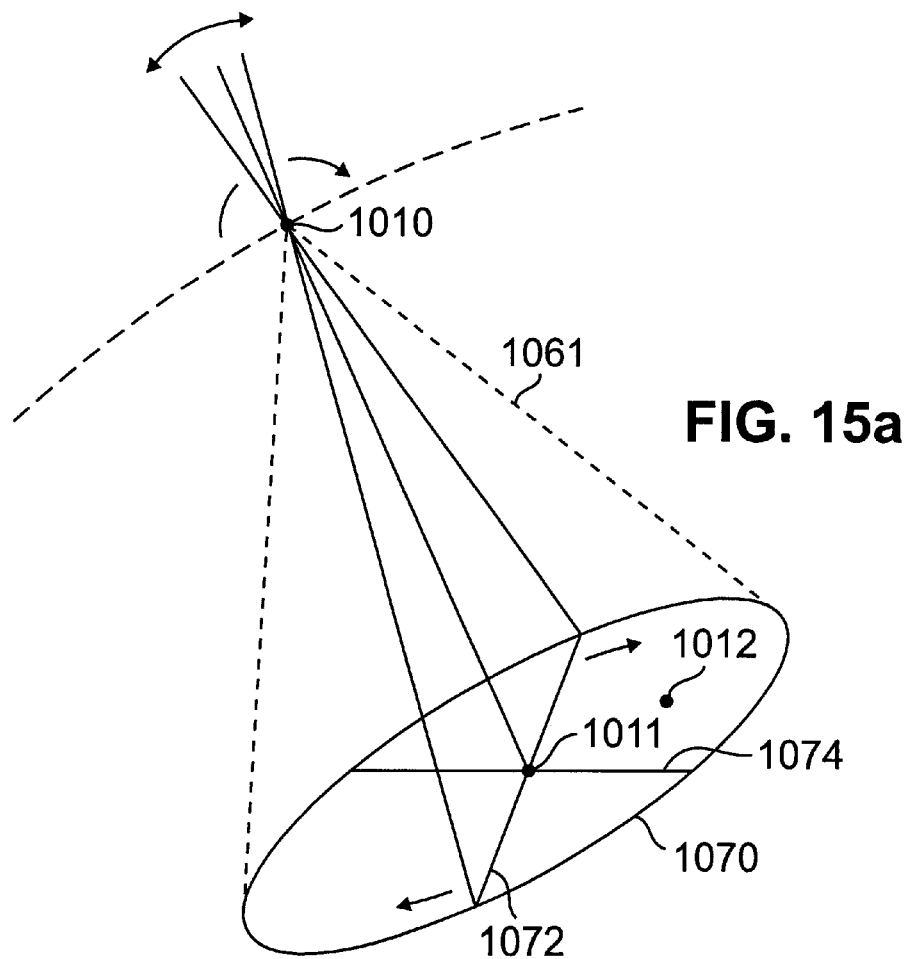
FIGS. 15a–f illustrate a "field of view" display and corresponding conical section through a body.
Figure 15B:
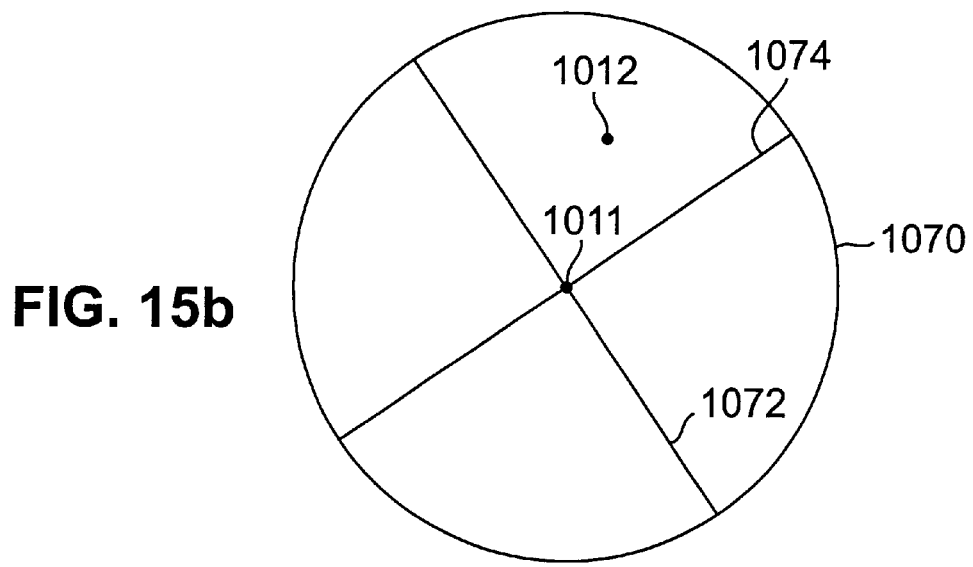
Figure 15C:
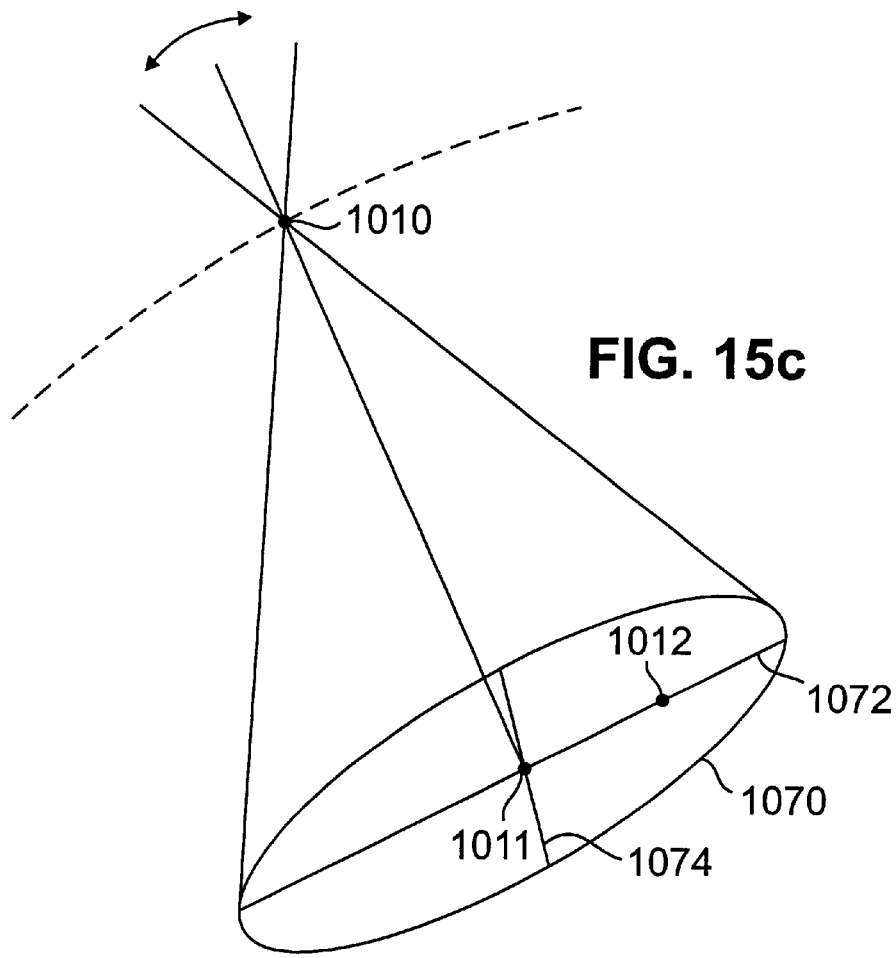
Figure 15D:
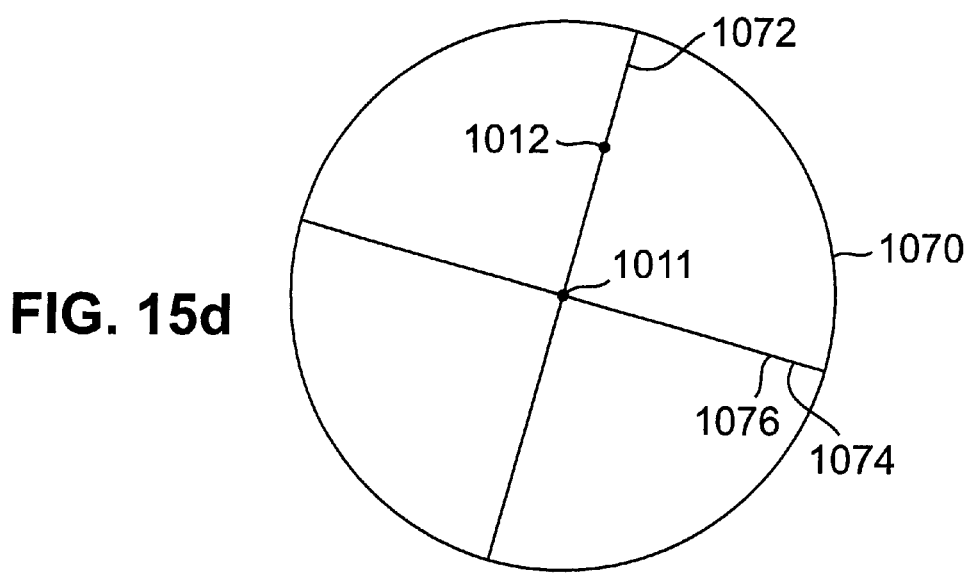
Figure 15E:
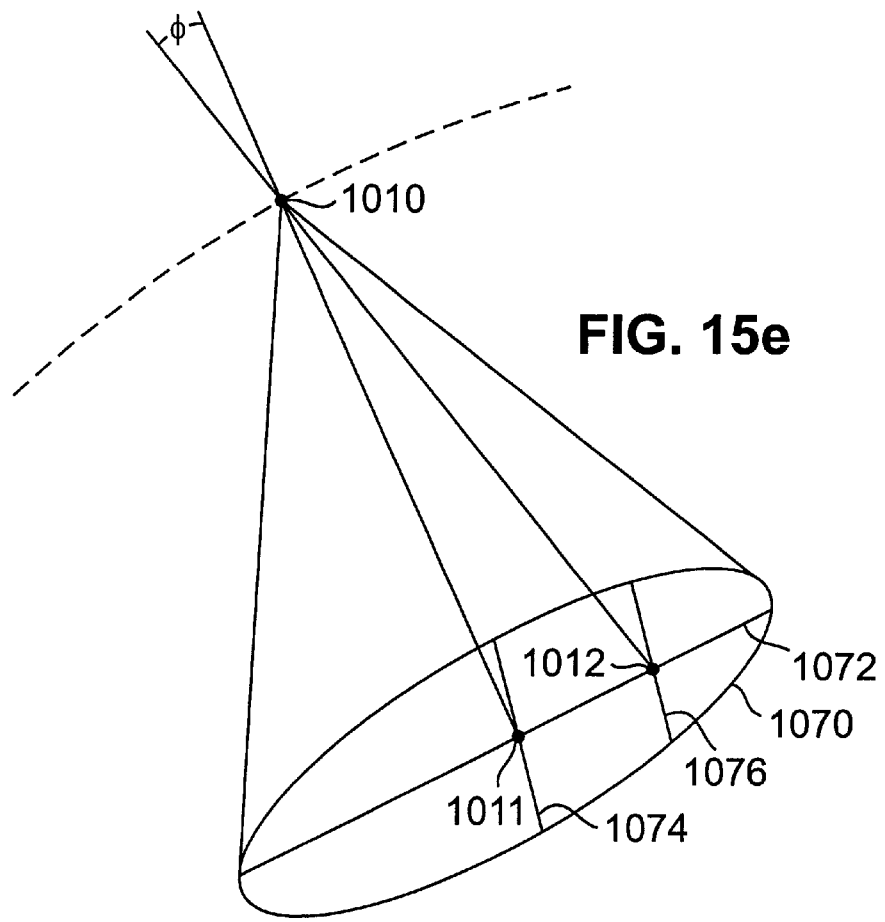
Figure 15F:
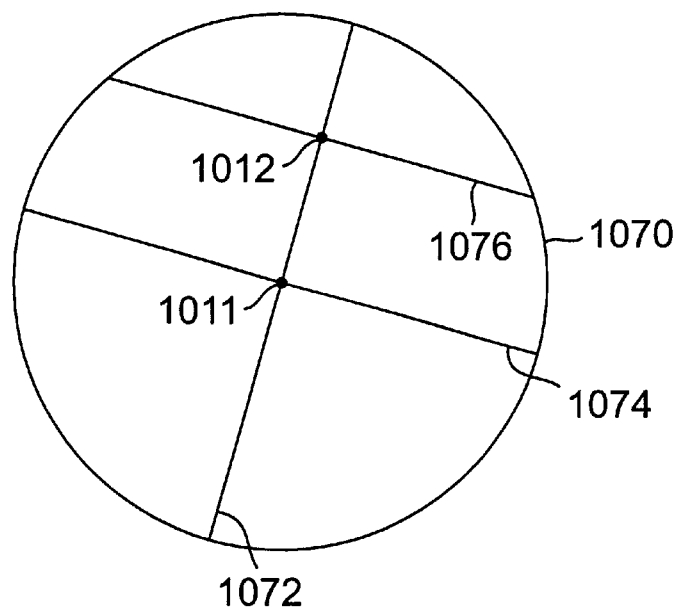

In addition to, or as an alternative to, using a navigational view to provide visual feedback during the alignment procedure, a "field of view" display can be provided. Referring to FIGS. 15*a*–*f*, the field of view display uses a representation of a cross-section of a cone extending below the entry point. Referring to FIG. 15*a*, the central axis of a cone 1061 is coincident with the central axis of the mounting base of a guidance fixture mounted at an entry point 1010. That is, the central axis of the cone is generally perpendicular to the surface of the skull at the entry point. The angle of the cone corresponds to the range of possible alignments of a guidance fixture mounted at the entry point. In this embodiment, this is a 45 degree angle. The cross-section is normal to the central axis of the cone, and passes through a target point 1012. Referring to FIG. 15*b*, the corresponding display shows a circular section 1070 of the scanned image. The center 1011 and the target point 1012 are indicated. Also indicated are two orthogonal axes. An axis 1072 corresponds to the achievable orientations of the guidance fixture as its pivoting collar is moved in the rotating collar. Another axis 1074 is orthogonal to axis 1072. Motion of the rotating collar rotates the orientation of axes 1072 and 1074. These axes can be thought of as intersections of the navigational planes with the bird's eye plane of a navigational view, although here, the intersecting lines rotate with the rotation of the guidance fixture while in the navigational view, the navigation planes remain fixed as the guidance fixture is rotated. Referring to FIG. 15*c*, after an appropriate rotation, axis 1072 passes through target point 1012. FIG. 15*d* shows the display after this rotation. Motion of the pivoting collar is indicated by a line 1076, parallel to axis 1074. If the pivoting collar is centered, then line 1076 is aligned with axis 1074, as is shown in FIG. 15*d*. When the guidance fixture is aligned with the target point, line 1076 passes through target point 1064, as does axis 1072. FIG. 15*f*, corresponding to FIG. 15*e*, shows the display after alignment is achieved. This circular field of view display provides intuitive visual feedback to the surgeon who is aligning the guidance fixture. Furthermore, displacement of the x-y table can also be shown in such a field of view display, by indicating the intersection of the resulting instrument trajectory on the circular display.

Inserting the Surgical Instrument

Figure 16:
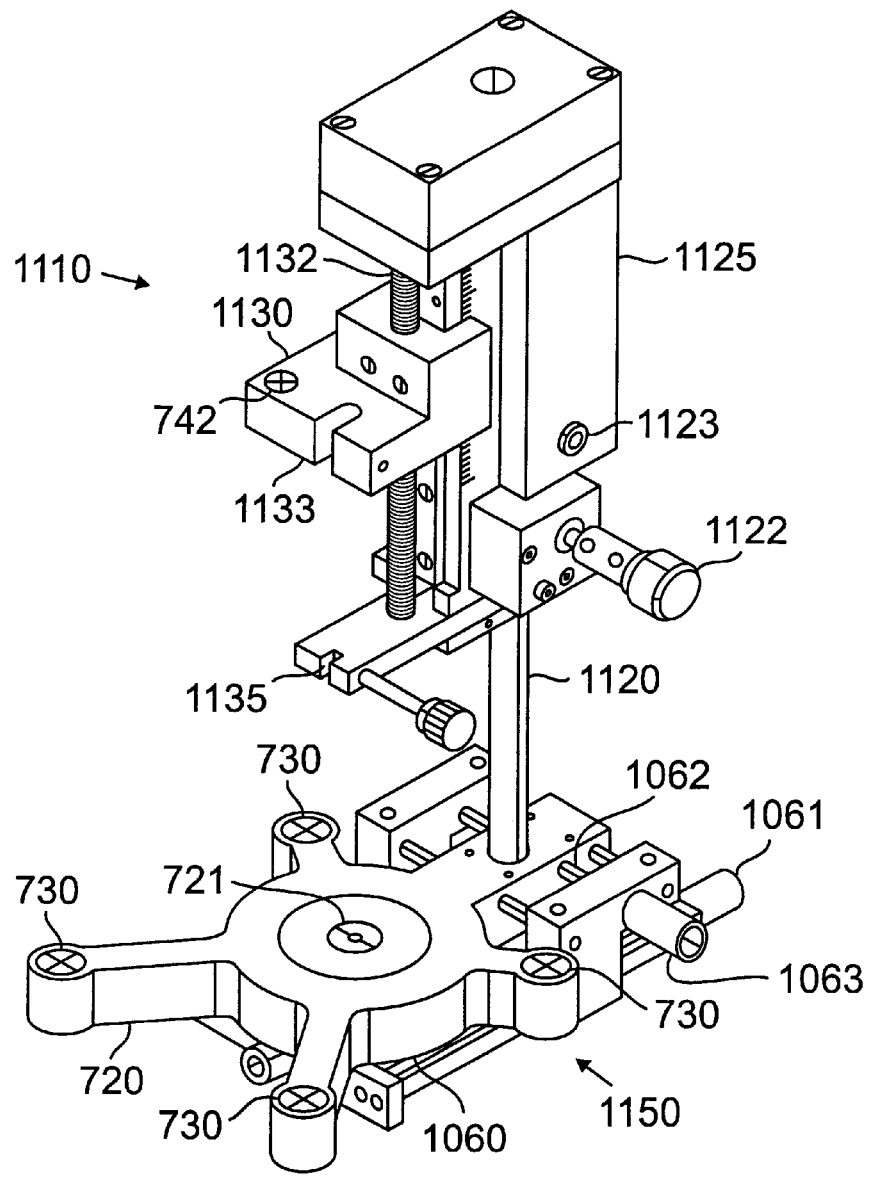
FIG. 16 is a guidance fixture including an adjustable base and an instrument drive attached to a base platter.
Figure 16:
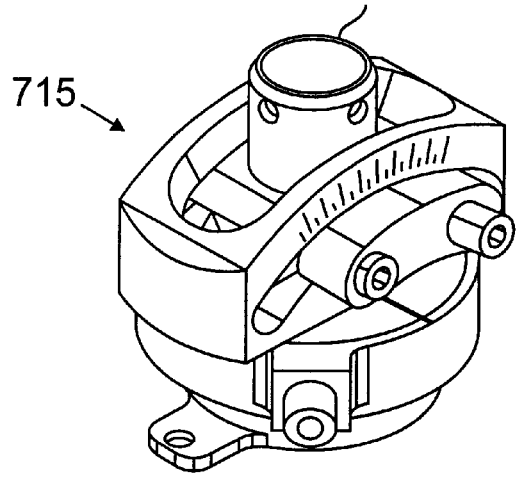

Referring to FIG. 16, an instrument drive 1110 is attached to base platter 720 prior to attaching the combination of instrument drive 1110, base platter 720, and x-y table 1150 to guidance base 715. In FIG. 16, instrument drive 1110 is shown partially mounted onto a drive post 1120. Prior to attachment to guidance base 715, drive post 1120 is fully inserted into instrument drive 1110 so that instrument drive 1110 is in contact with base platter 720. Base platter 720 can be displaced relative to guidance base 715 in a plane orthogonal to entry column 850 using two perpendicular adjustment screws 1060, and 1062 turned by x-y table adjustment knobs 1061, and 1063. Note that prior to alignment (FIG. 1, step 170) the x-y table is adjusted so that central opening 721 in base platter 720 is centered over entry column 850.

Instrument drive 1110 includes a drive platform 1130 that moves within a drive mechanism 1125 along a threaded rod 1132. Threaded rod 1132 is oriented parallel to drive post 1120 and perpendicular to base platter 720. In this embodiment, rotation of threaded rod 1132, which causes displacement of drive platform 1130, is manual using a mechanism that is not shown. Alternative embodiments can use an electronic stepper motor or a manual hydraulic drive to rotate threaded rod 1132 and thereby displace drive platform 1130.

In operation, a surgical instrument, such as a microelectrode, is passed into the brain through a guidance tube. After alignment of guidance fixture 710, the guidance tube is manually inserted into the brain through central opening 721 in base platter 720. The guidance tube is then secured in clamp 1135 that is fixed relative to drive mechanism 1125. The instrument is passed into the guidance tube and is secured in a clamp 1133, which is fixed relative to drive platform 1130.

Instrument LED 742 is attached to drive platform 1130. The displacement of the end of the surgical instrument from instrument LED 742 is known to localization application 588 which executes on workstation 580. By tracking the position of instrument LED 742, as well as platter LEDs 730, the position of the end of a surgical instrument on workstation 580 and displayed on display 610 (FIG. 9) to the surgeon. The surgeon then uses this visual feedback in adjusting the depth of the instrument.

Surgical Instruments

Various types of surgical probes or instruments can be attached to drive mechanism 1110 shown in FIG. 16. One type of instrument is an electrode, such as a recording micro-electrode or a stimulating electrode or lesioning electrode. The electrode is introduced into a rigid insertion (guidance) tube that is attached to drive mechanism 1110. Another type of instrument is a hypothermia cold probe.

In cases of movement disorder or pain surgery, a chronically implanted stimulating electrode can be placed utilizing an insertion tube. The lead, being of a smaller diameter than the insertion tube, can be slipped through the insertion tube upon removal of the drive and guide assembly, to allow fixation of the chronically implanted electrode into the brain. The electrode is secured to the skull using a compression-fitting. A chronically implanted recording electrode can similarly be placed during epilepsy surgery to monitor abnormal activity within the deep brain utilizing similar techniques.

When an instrument is to be implanted chronically, it is important that the instrument is not disturbed during the process of securing it to the skull. For instance, after a chronically implanted recording electrode has been accurately positioned using the guidance fixture, the guidance fixture must be removed before the lead of the electrode can be secured. However, the electrode can be dislodged during this process prior to securing the lead.

Figure 17A:
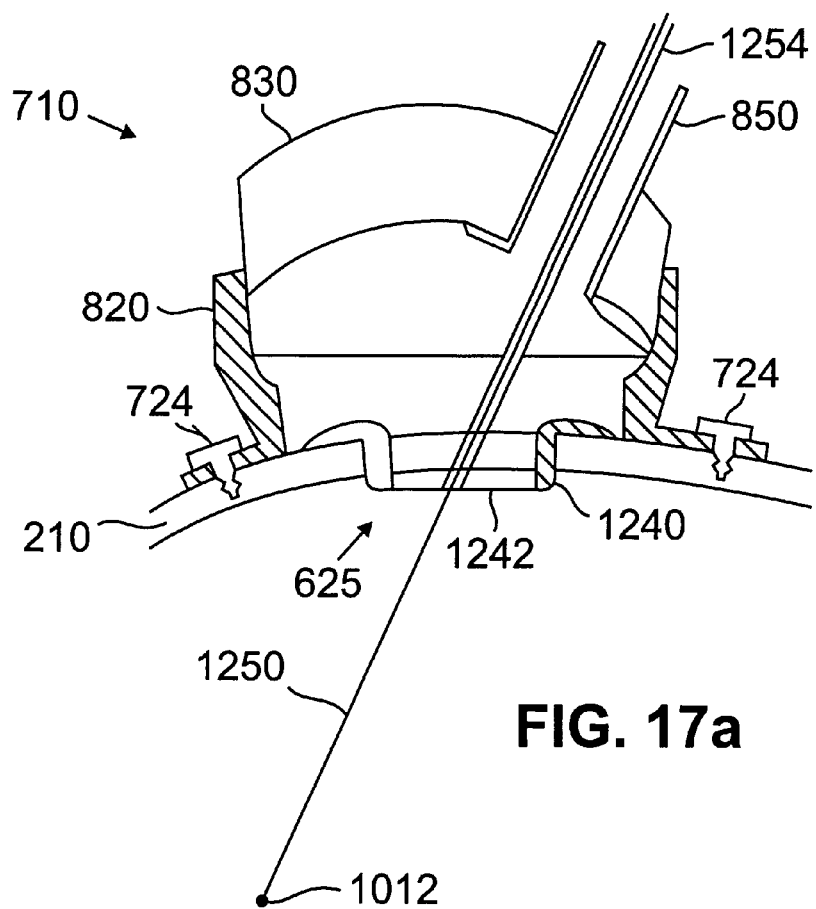
FIGS. 17a–b show a burr hole ring used to secure an instrument using a flexible membrane.

In order to prevent dislodging of the electrode while removing the guidance fixture, a flexible membrane is used to constrain the motion of the electrode in the burr hole. Referring to FIG. 17*a*, a circular burr hole ring 1240 is inserted into burr hole 625 after the surgeon drills the burr hole prior to attaching mounting base 820 over the burr hole. Burr hole ring 1240 has a thin elastic membrane 1242 across the bottom of the ring. Therefore, an instrument that passes through the burr hole must pass through membrane 1242 to enter the brain. Elastic membrane 1242 is made of a material such as Silastic (silicone rubber) that is biocompatible and non-permeable. The membrane is self-sealing in that if it is punctured by an instrument that is then withdrawn, the membrane remains non-permeable.

After attaching guidance fixture 710 to its mounting base 820, the fixture is aligned to direct an electrode 1250 toward the target point 1012. Electrode 1250 passes through an insertion tube 1254. Insertion tube 1254 is driven through membrane 1242 puncturing the membrane, then the electrode is driven to target point 1012. Alternatively, a separate pointed punch can be driven through the membrane to make a hole through which the insertion tube is subsequently inserted.

After electrode 1250 is properly positioned at the target point, guidance fixture 710 is removed, and insertion tube 1254 is removed.

Figure 17B:
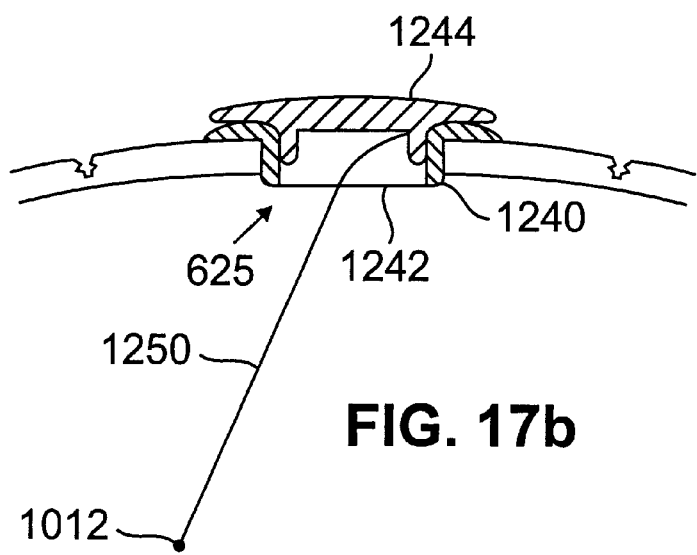

Referring to FIG. 17*b*, electrode 1250 remains secured by elastic membrane 1242, preventing the electrode from being dislodged while the guidance fixture is being removed and the while the burr hole, which still has burr hole ring 1240 inserted, is exposed. A burr hole cap 1244 is then secured in burr hole ring 1240. The lead of electrode 1250 is clamped in a channel between the burr hole ring and cap, thereby preventing tension on the lead from dislodging the electrode.

A similar approach is used to secure other chronically implanted instruments, such as a shunt tube. Membrane 1242 is first punctured, for instance using a punch, using an insertion tube, or using the instrument itself. The instrument is inserted using the guidance fixture. After the guidance fixture is removed, an appropriate cap are secured to the burr hole ring 1240.

Note that a burr hole ring 1240 with membrane 1242 is applicable for securing instruments inserted into the brain using other methods than guided using a guidance fixture. For instance, the same burr hole ring and cap can be used when inserting an instrument freehand or using a conventional stereotactic frame.

In cases of hydrocephalus or other situations where chronic drainage of intracranial cavities is necessary, a shunt tube, such as a ventricular shunt, can be applied through the insertion tube into the target such as the ventricles of the brain. The shunt tube will have a stylet and be slipped into the insertion tube.

The insertion tube structure and its retention ring will have varying diameters, depending on the diameters of the various objects that can be placed in the insertion tube, such as the shunt tube, in this application, or micro-electrodes, in the prior application. The insertion tube, therefore, will be connected to the drive mechanism using varying sized retention rings. Referring to FIG. 16, the retention rings would be fit at points 1133 or 1135 on drive mechanism 1110. The shunt will be directed towards the target established by the software mechanism alluded to above. The shunt tube will then be secured to the skull via mechanisms described in prior art, or using an elastic membrane described above.

Alternatively, a biopsy probe can be inserted into the insertion tube by first placing a biopsy tube with a trocar/obturator through the insertion tube. The mechanism would then be directed down towards the appropriate target using the drive mechanism. The obturator would be removed, and a cutting blade will then be inserted into the biopsy tube.

In applications in which a radioactive seed for brachytherapy, a targeting nodule with a radio sensitizing, chemotherapeutic agent for external beam radiation, or a sustained release polymer drug or microdialysis capsule for local drug administration, are required for placement in a deep brain target, a different insertion tube can be connected to the drive mechanism 1110. A delivery catheter can be placed through the insertion tube. The whole mechanism can be directed towards the deep target using the software system as alluded to above. An insertion plunger can be used to insert the object of delivery and the system is then be removed after insertion of the object. A micro-endoscope can also be inserted through the insertion tube mechanism described above and deep brain structures can be visualized prior to excision or lesioning.

X-Y Table

In certain surgical procedures, it is desirable to drive a surgical instrument along several parallel tracks. This is facilitated using x-y table 1150 (FIG. 16). Before an instrument is driven toward the target, an offset is adjusted using adjustment knobs 1061, and 1063. These knobs include markings that allow precise adjustment.

An example of a procedure using penetration of an instrument along parallel tracks involves mapping the electrical activity of a region of the brain. The surgical instrument in this case is a thin electrode that is repeatedly inserted to points on a two- or three-dimensional grid. At each point, electrical activity is monitored.

Surgical Retractor

Figure 17C:
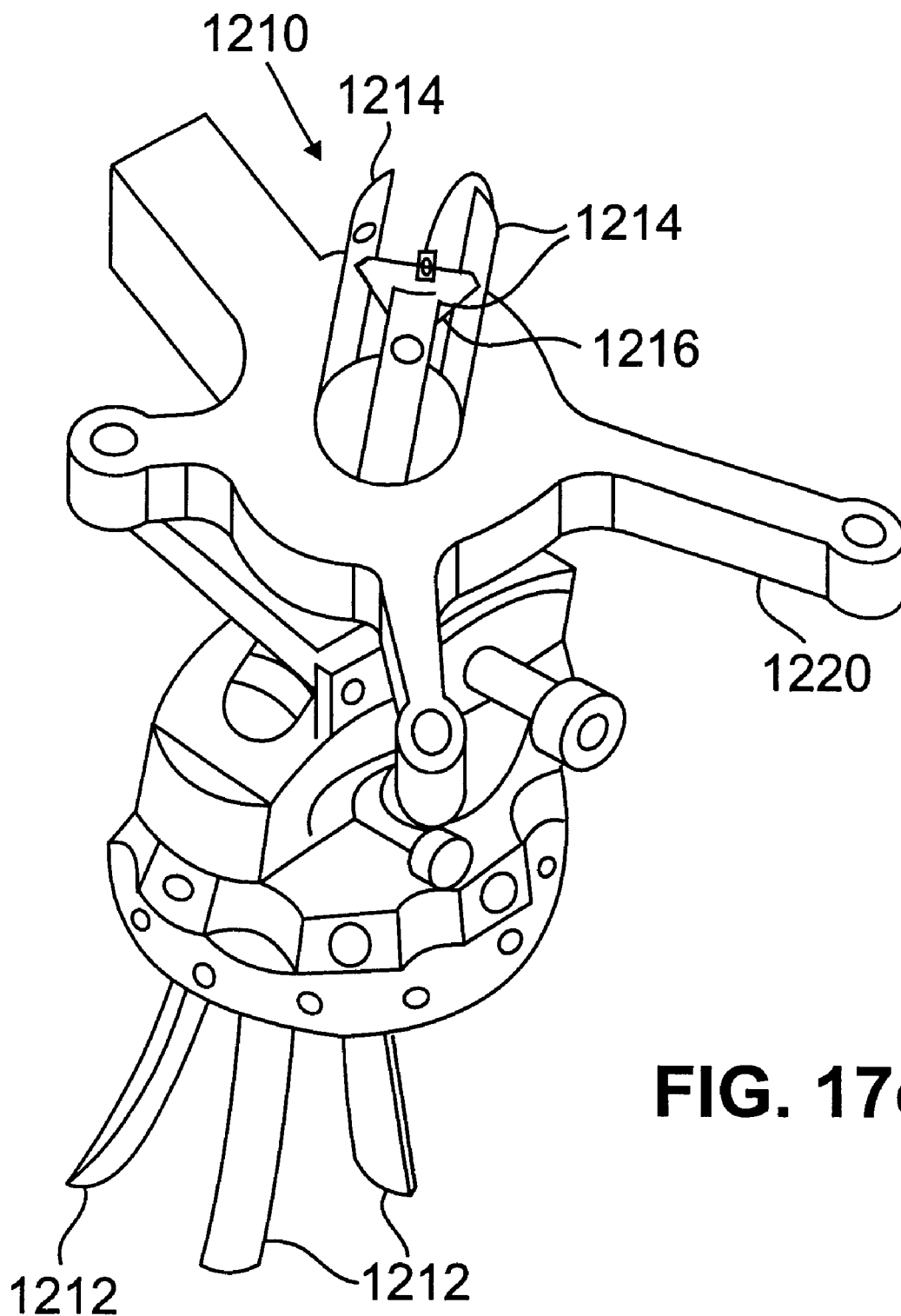
FIG. 17c is a retractor in a guidance fixture.

Referring to FIG. 17*c*, when larger masses within the brain, such as brain tumors, have to be removed with precision, the drive mechanism has a localizing surgical retractor 1210 mounted in place of the insertion tube, and base platter 1220 has a large central opening through which the retractor passes. Retractor 1210 includes three or more spatulas 1212 inserted through base platter 1220 and the entry column. Each spatula 1212 includes a tracking LED 1214 attached to it. The relationship of the spatulas is controlled by a screw assembly 1216 that allows the relative distance between the spatulas to be modified. Relatively small movement at the screw assembly results in a larger movement at the other ends of the spatulas due to the pivoting of the spatulas within the retractor. Tracking LEDs 1214 are tracked by the camera array and the localization application computes the depth of spatulas 1212 and their displacement from the central axis. Using the tracking approach described above, surgical localizing retractor 1210 is directed towards the brain target. Upon acquiring the target, screw assembly 1216 is adjusted to expand localizing retractor 1210 to allow visualization of the underlying brain. A variety of surgical instruments can be attached to retractor 1210 in addition to using the retractor with more conventional manual techniques. These instruments can include an endoscope, an ultrasonic aspirator, an electronic coagulation/evaporator/ablator, or a laser.

Fixture Validation

Figure 18:
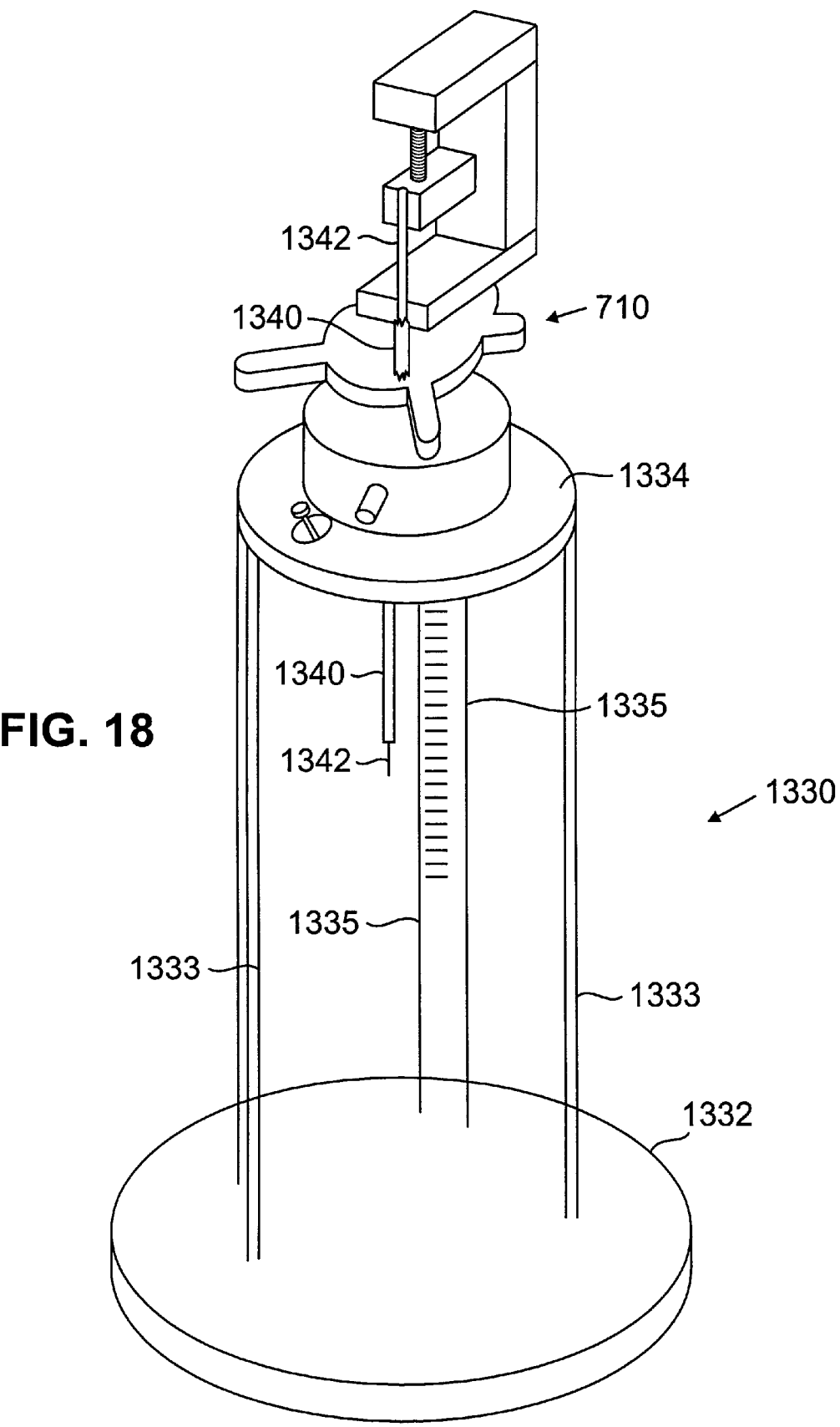
FIG. 18 is a calibration jig.

An optional fixture validation step (FIG. 1, step 130) can be used to confirm that the position of the tip of the surgical instrument is accurately tracked. Two types of validation can be performed. Referring to FIG. 18, guidance fixture 710 is attached to an upper mounting plate 1334 of a calibration jig 1330. Prior to attaching guidance fixture 710 to calibration jig 1330, pivoting locking knob 846 (FIG. 10) is loosened allowing pivoting collar 840 to pivot. After guidance fixture 710 is attached, pivoting collar 840 is centered and pivoting locking knob 846 is tightened. A guidance tube 1340 is clamped into the guidance fixture, and a surgical instrument 1342 is passed through the guidance tube. Guidance tube 1340 protrudes below upper mounting plate 1334. A ruler 1335 can then be used to measure the depth of penetration of the guidance tube. Similarly, ruler 1335 can be used to measure the penetration of surgical instrument 1342.

Figure 19:
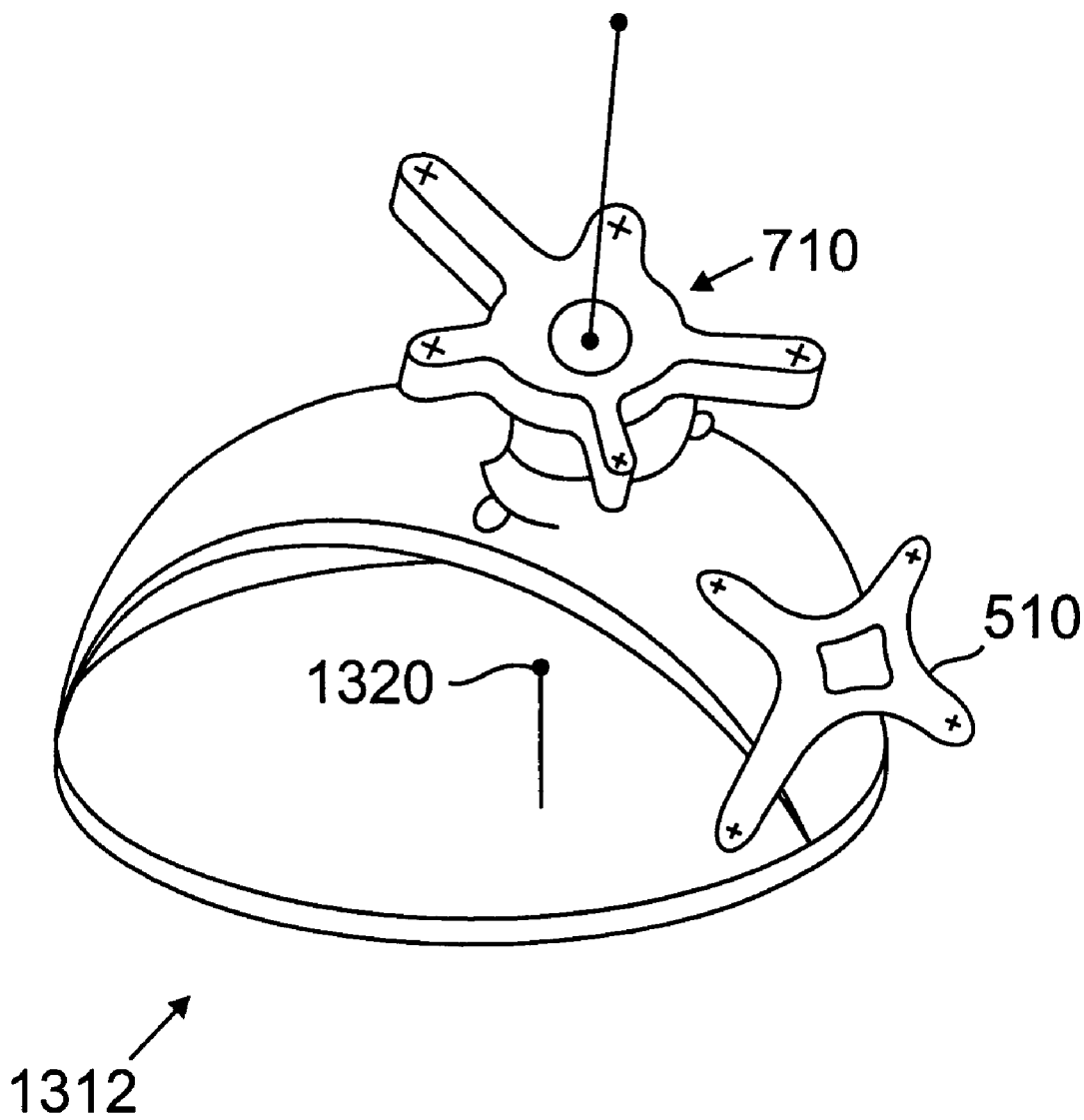
FIG. 19 is a phantom jig and a guidance fixture and a tracking MIRRF attached to the jig.

Referring to FIG. 19, a validation (or "phantom") jig 1312 can also be used. Tracking MIRRF 510 is attached to validation jig 1312. Guidance fixture 710 is be mounted on validation jig 1312. A phantom target point 1320 at a known position relative to validation jig 1312, and therefore at a known position relative to the fiducial points on tracking MIRRF 510, is chosen. The localization application 588 is programmed with the phantom target position. Using the procedure that will be used during the surgical phase, the surgeon performs the registration and alignment steps and then drives the instrument through guidance fixture 710. If the tip of the instrument is coincident with the phantom target point, then guidance fixture 710 is validated. If for some reason the instrument is not coincident with the phantom target point, for example, due to improper attachment of the instrument to the drive assembly resulting in an incorrect depth calibration, the surgeon readjusts the instrument and attempts the validation step again.

Alternative Scanning, Registration, and Tracking

Other embodiments of the invention use alternative scanning, registration, and tracking markers, and methods of scanning and registration.

Figure 20:
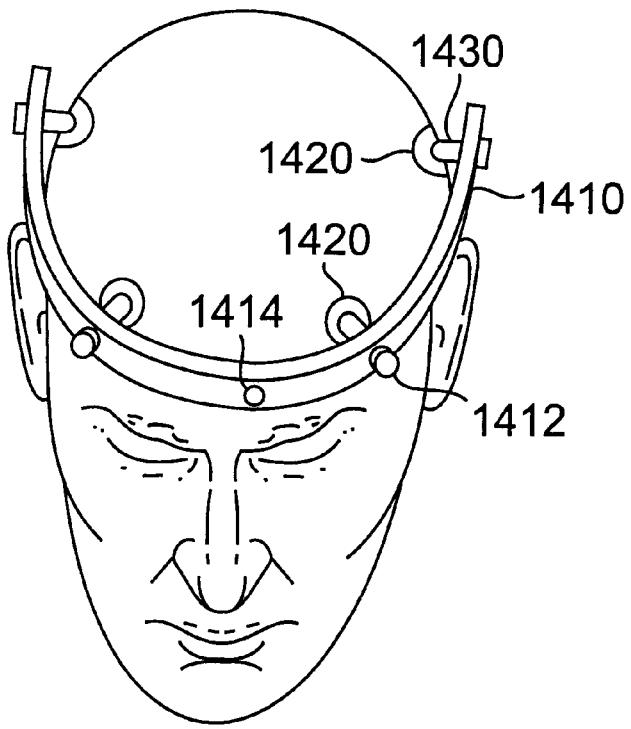
FIG. 20 is an arc shaped MIRRF attached to a head including a view of a threaded insert and mounting bolt.
Figure 20:
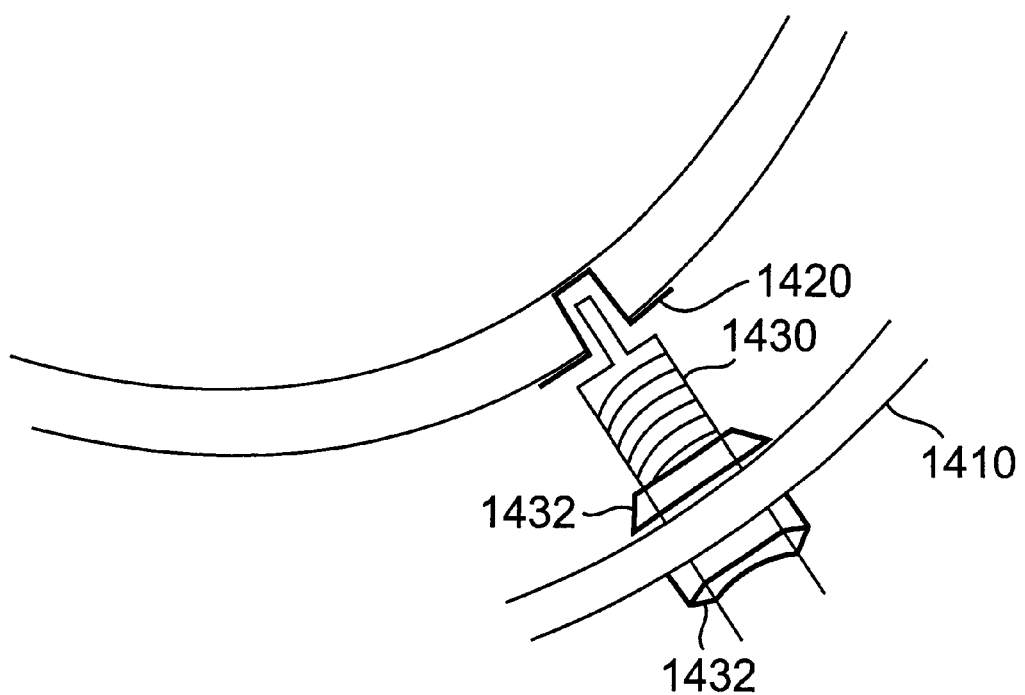

In the first embodiment, scanning MIRRF 310 and tracking MIRRF 510 are star-shaped. Other alternative shapes of MIRRFs can be used. Referring to FIG. 20, an arc-shaped MIRRF 1410 is attached to threaded inserts 1420 using bolts 1430, and marking and locking nuts 1432. Arc-shaped MIRRF 1410 includes scanning fiducial markers 1412. The fiducial markers are more widely spaced than in star-shaped MIRRFs 310, and 510, resulting in a more accurate tracing of the MIRRF. During insertion of threaded inserts 1420, arc-shaped MIRRF 1410 acts as a template for accurate positioning of the threaded inserts.

In embodiments described above, threaded inserts are inserted into the skull to provide the fixed points of attachment for MIRRFs. Alternative embodiments use other types of anchors or forms of mechanical attachment, for example, including protruding posts that are attached to the skull. A MIRRF is then attached to the posts.

Figure 20A:
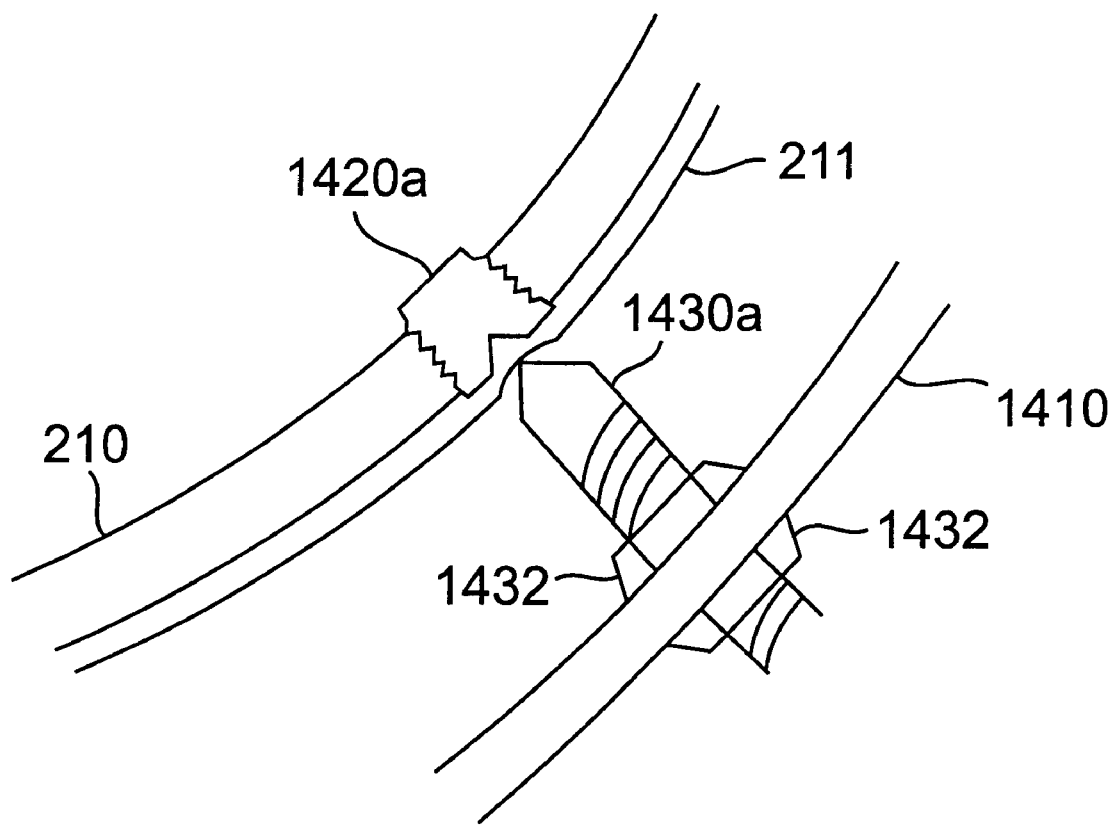
FIG. 20a is a MIRRF attached to a subcutaneous insert.

Another alternative method of attachment uses subcutaneous anchors. Referring to FIG. 20*a*, an insert 1420*a* in fixed in the skull. Insert 1420*a* has a divot in its head, which provides an accurate position reference. After insert 1420 is attached to the skull, skin 211 is secured over the insert. At later times, these divots are used to mate clamping posts 1430*a* on a MIRRF, which hold the MIRRF in place. Since implanted divots are covered by the skin, they can remain in place for an extended period of time.

Such a subcutaneous insert allows repeated reattachment of a fixture, such as a scanning or tracking MIRRFs, or repeated reattachment of a guidance fixture itself. An application of such periodic reattachment is periodic microrecording from a particular location in the brain, or repeated lesioning of particular brain structures.

Subcutaneous inserts also allow other devices, including stereotactic radiation devices, to be repeatedly reattached at precisely the same location. These devices include the Gamma Knike, Lineal Accelerator (LINAC), or a multi-collimated machine, such as the PEACOCK device. This approach to reattachment provides greater precision than is possible using bite plates or facial molds to reposition the devices.

Figure 21:
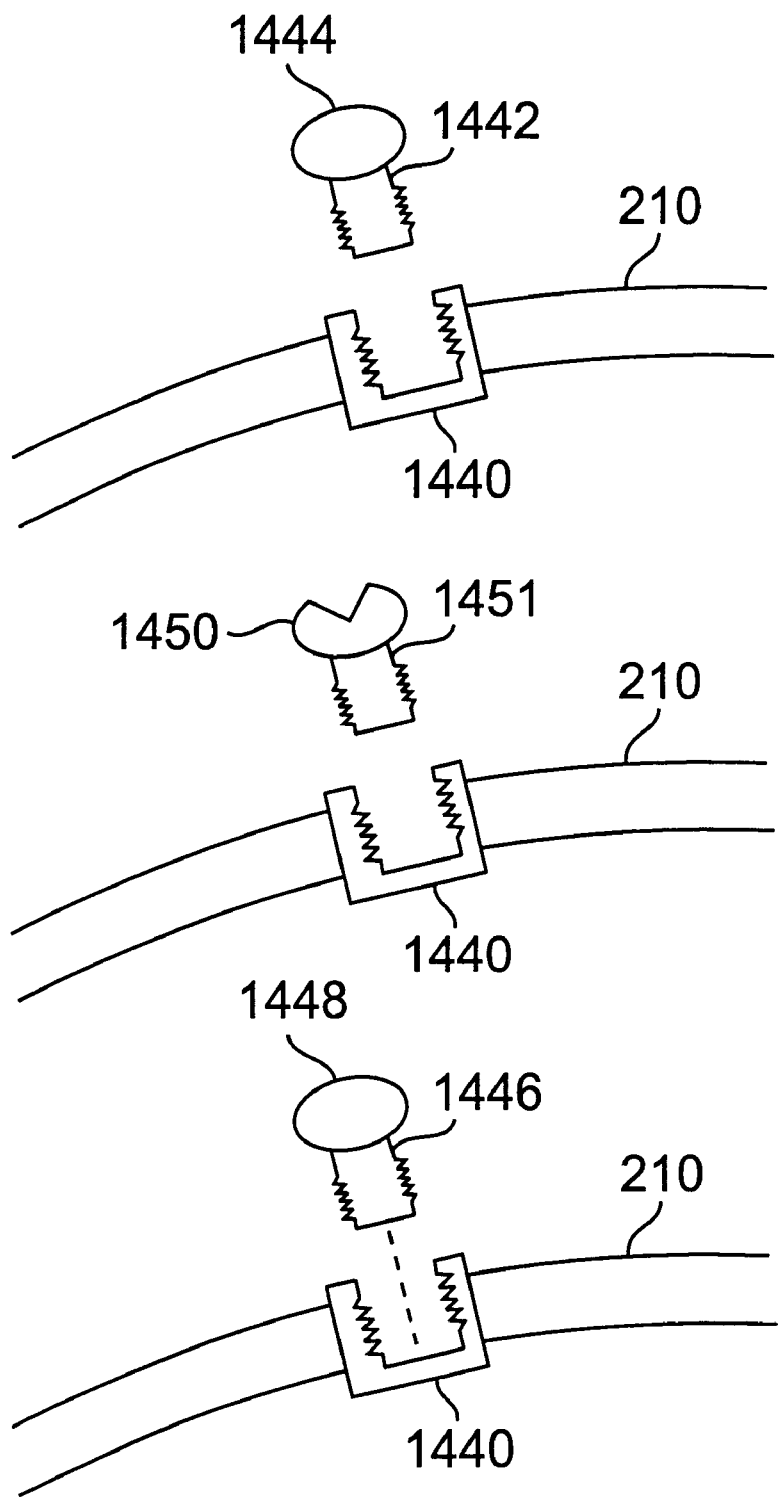
FIG. 21 is a scanning marker and a tracking marker attached to a threaded insert.

An alternative to use of a MIRRF is to attach markers directly to anchors in the skull. Referring to FIG. 21, each such anchor, shown as threaded insert 1440, can support a single scanning marker 1444 on a post 1442, subsequently support a single registration divot 1450 on a second post 1451, and then support a single tracking marker, LED 1448, on a third post 1446. The geometric relationship of the anchor to the scanning marker is the same as the geometric relationship of the anchor to the tracking marker thereby allowing a localization application to directly track the fiducial points by tracking the location of the tracking marker.

Using any of the MIRRF structures described, multiple MIRRFs can be used to provide increased accuracy in registration and tracking. For example, two star-shaped MIRRFs can be used, one on each side of the head.

In other embodiments, alternative attachment methods can be used to secure a guidance fixture to the skull. For instance, the mounting base can be relatively small and have extended "legs" extending radically and secured to the skin or skull with sharp points. These legs provide stabilization that may not be achievable using mounting screws through the smaller mounting base. The mounting base can alternatively include an insert that fits into the burr hole. This insert can also be threaded to allow direct attachment of the mounting base to the burr hole.

In other embodiments, threaded inserts are used to attach, and subsequently accurately reattach, conventional stereotactic frames. This allows the conventional stereotactic frame to be removed and then accurately reattached to the skull. Procedures, such as fractionated multi-day stereotactic radiation treatments could then be performed with the stereotactic frame being reattached for each treatment.

Figure 22:
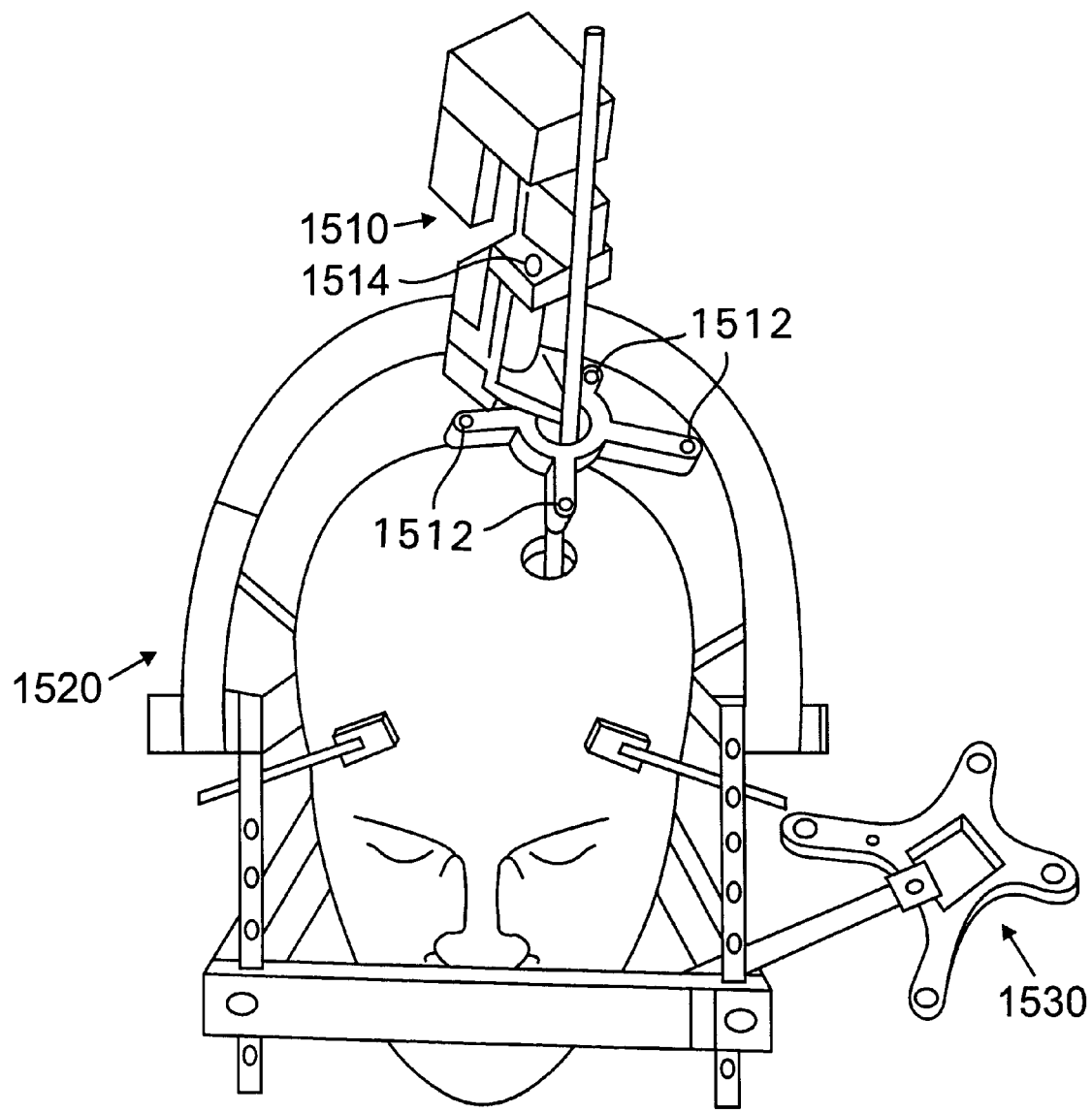
FIG. 22 is a guidance fixture and a tracking MIRRF attached to a conventional stereotactic frame.

Referring to FIG. 22, a modified guidance fixture 1510 is used in combination with a conventional stereotactic frame 1520. Guidance fixture 1510 includes an x-y positioning table with LEDs 1512 and an instrument drive with an LED 1514 for tracking the depth of the surgical instrument. The guidance assembly is positioned on frame 1520 to align with the planned surgical trajectory. A tracking MIRRF 1530 is attached to frame 1520 to allow dynamic tracking.

Rather than using a scanning MIRRF with scanning fiducial markers, or scanning fiducial markers attached directly to anchors embedded in the skull, alternative embodiments can use other features for registration. In one alternative embodiment, paste-on scanning markers are attached to the skin. During the registration phase, the cranial probe is positioned at each of the paste-on markers in turn, rather than at the fiducial points on a MIRRF. Tracking LEDs are attached in a fixed position relative to the skull in some other way than using a MIRRF, for example, using an elastic headband. Rather than using pasted on fiducial markers, another alternative embodiment uses accessible anatomical features. These features are located in the scanned image, and the probe is positioned at these features during the registration phase. Still another alternative does not use discrete fiducial points, but rather makes use of the surface shape of the skull in a "surface merge" approach. The surface of the skull is located in the three-dimensional image. During registration, the cranial probe touches a large number of points on the skull. The locations of these points is matched to the shape of the skull to determine the conformal mapping from the physical coordinate system to the image coordinate system.

Figure 23:
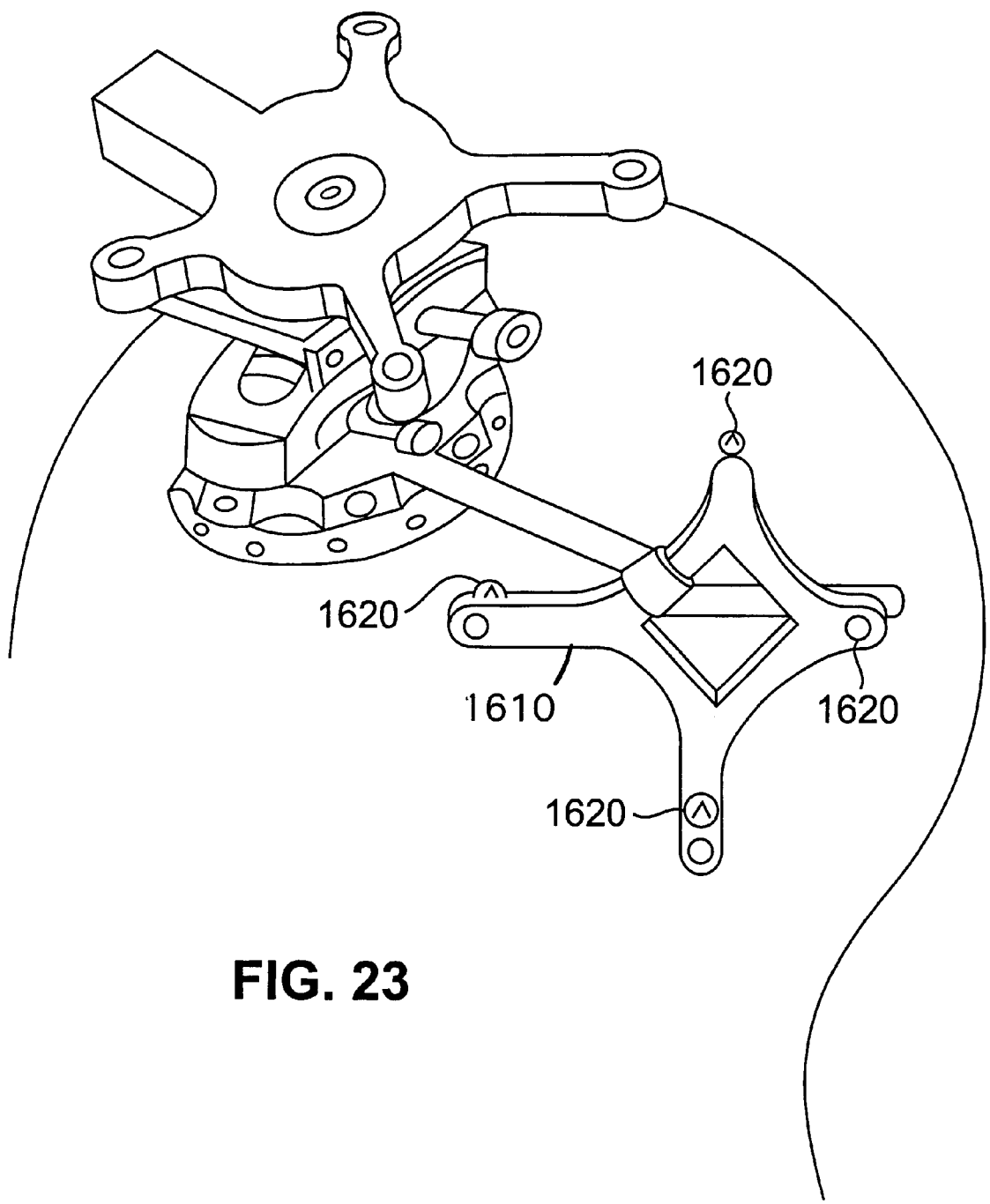
FIG. 23 is a tracking MIRRF attached directly to a guidance fixture.

In yet another embodiment, referring to FIG. 23, a tracking MIRRF 1610 can be attached directly to the base of a guidance fixture 710. Tracking MIRRF 1610 is only useful for tracking after guidance fixture 710 has been attached to the skull. In this approach, registration is based on fiducial points elsewhere on the skull than tracking MIRRF 1610.

Locating the entry point, over which guidance fixture 710 is attached can be accomplished using one of a variety of alternative techniques. For example, the entry point may be known for some standardized procedures. Alternatively, the entry point may be determined by registration of the skull and the three-dimensional image based on fiducial markers attached to the head, for example using adhesive pads, anatomical markers, or a "surface merge" technique as described above.

Once the guidance fixture and tracking MIRRF 1610 are attached to the skull, LEDs 1620 on tracking MIRRF 1610 are used to track the location of the skull, and thereby track the location of the surgical instrument. A reregistration step (FIG. 1, step 160) can be performed to determine the relative position of the fiducial points to LEDs 1620.

Various mechanical adjustments of guidance fixture 710, if performed when an guidance tube is inserted in the brain, would potentially damage the brain tissue. The guidance fixture optionally includes a feature that the various locking knobs and x-y adjustment knobs are rotated using a removable knob (or key). When not in use, this knob is stowed on the drive assembly. Whenever the removable knob is removed from its stowed position, the signal from an electrical sensor on the drive assembly that is connected to the workstation causes a warning, for example on the computer display, to be provided to the surgeon.

Instrumented and Actuated Guidance Fixtures

In general, the embodiments of the guidance fixture described above rely on a surgeon manually adjusting the guidance fixture and driving a surgical instrument into the body based on visual feedback. The manual steps carried out by the surgeon include adjusting the orientation of rotating collar 830 (FIG. 10) with respect to mounting base 820, and adjusting pivoting collar 840 by turning adjustment knob 844. The surgeon also adjusts x-y table 1150 (FIG. 10) by turning x-y table adjustment knobs 1061 and 1063 (FIG. 16). The visual feedback which is presented to the surgeon on a computer display is computed using remote sensing of the location and adjusted orientation of the fixture. As described previously, the remote sensing of the guidance fixture is based on determining the locations of tracking markers attached to the fixture as well as of tracking markers attached to the head.

As an alternative to using a remote sensing approach for determining the position and orientation of the guidance fixture relative to the body to which the fixture is attached, an instrumented guidance fixture can be used. In an instrumented guidance fixture, the position and orientation or the guidance fixture as well as the position of the surgical instrument relative to the guidance fixture are determined using sensors which directly encode the configuration of the fixture. The outputs of these sensors are used to compute the image which is provided as feedback to the surgeon. For instance, electrical rotary and linear encoders are used to generate electrical signals that are passed from the guidance fixture to the workstation that computes the visual feedback that is presented to the surgeon.

Figure 24A:
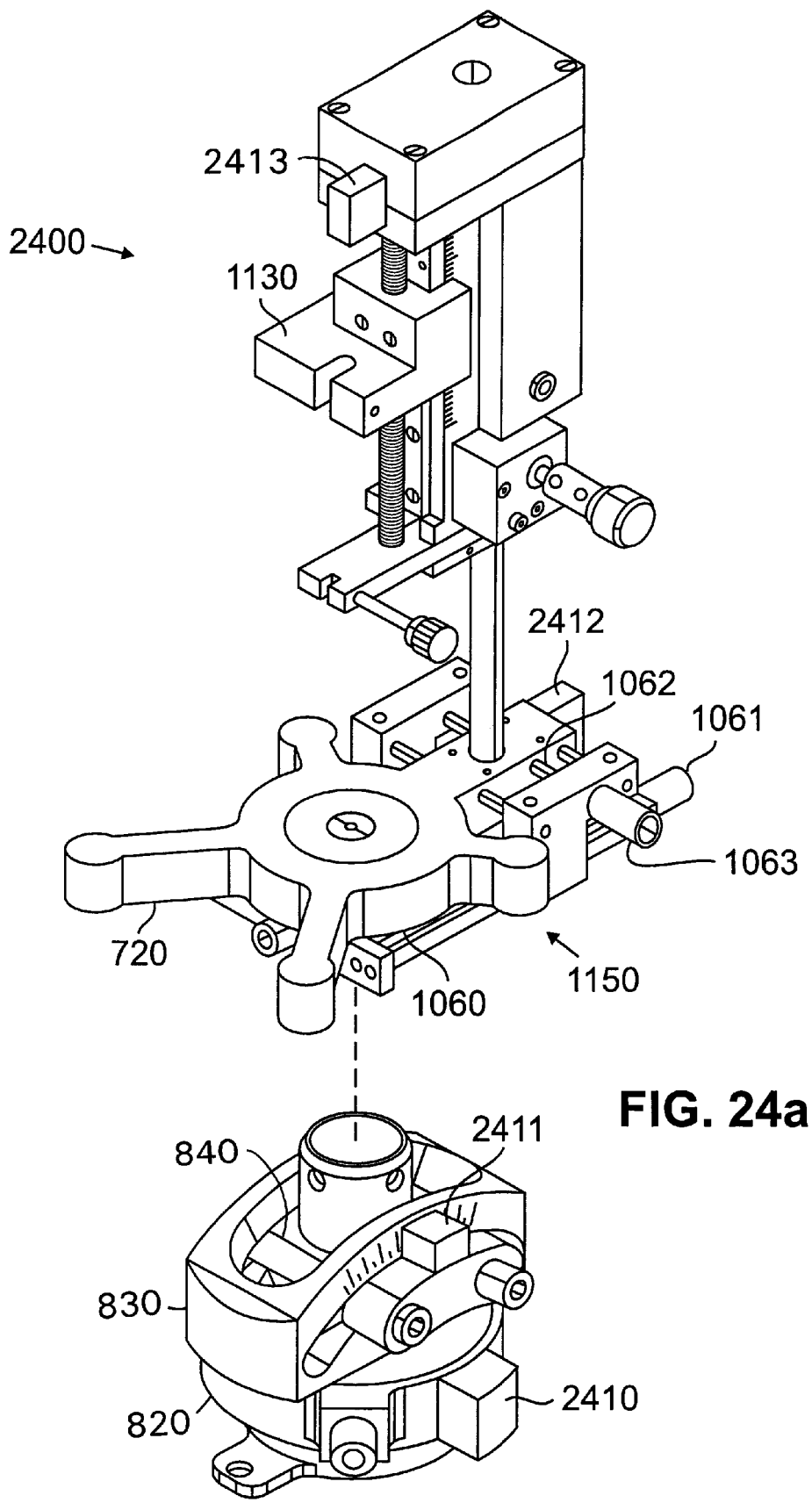
FIGS. 24a–b illustrate an instrumented guidance fixtures.

Referring to FIG. 24a, an instrumented guidance fixture 2400 includes five electrical sensors, two that encode the angles of rotation of rotating collar 830 and pivoting collar 840 (sensors 2410), two for the x and y displacements of x-y table 1150 (sensors 2412), and one for the displacement of instrument drive platform 1130 (sensor 2413).

Figure 24B:
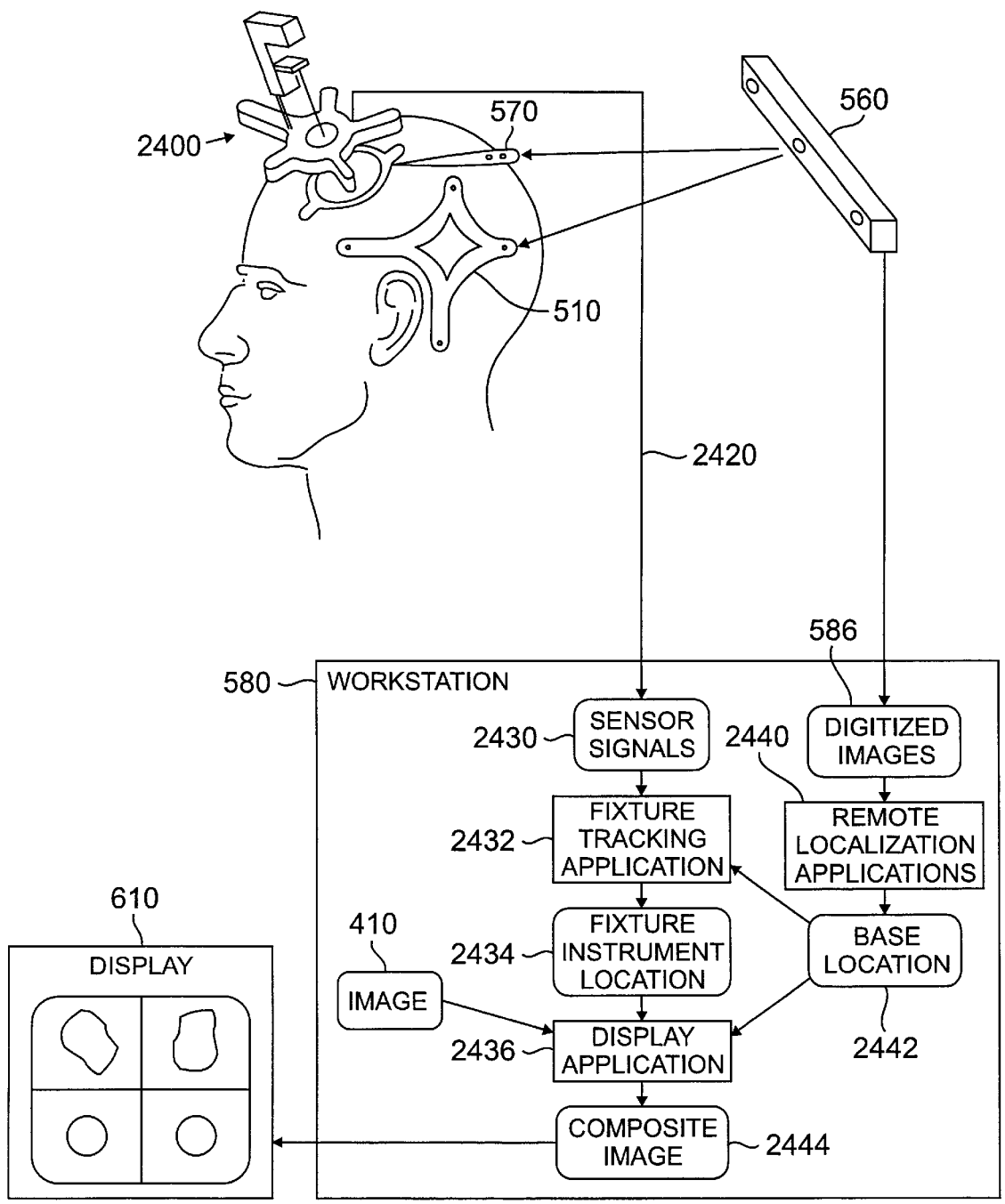

Referring to FIG. 24b, a workstation 580 accepts and stores sensor signals 2430 from sensors 2410–2413 (not shown in FIG. 24b) on instrumented guidance fixture 2400. A fixture tracking application 2432 executing on workstation 580 takes sensor signals 2430 and computes fixture/instrument location 2434, which includes the location and orientation of the guidance fixture 2400 and of the surgical instrument (if an instrument is inserted in the drive of the fixture). These orientations and locations are computed in the frame of reference of the base of guidance fixture 2400.

A display application 2436 combines fixture/instrument location 2434 with a previously computed base location 2442, which includes the location and orientation of the base of guidance fixture 2400 in the frame of reference of the scanned image 410, to compute the orientation and location of the guidance fixture and the instrument in the frame of reference of the image. Display application 2436 then combines this computed location and orientation with image 410 to form composite image 2444, which shows representations of the fixture and instrument in conjunction with one or more views of the scanned image. Composite image 2444 is shown on display 610, which provides visual feedback to the surgeon who manipulates the guidance fixture and the instrument.

Note that the fixture tracking application 2432 executed on workstation 580 relies on base location 2442, which includes knowledge of the location and orientation of the base of guidance fixture 2400 in the frame of reference of the head. Note also, that once the base of guidance fixture 2400 is attached to the head, base location 2442 remains fixed as long as the base remains firmly attached. Therefore, workstation 580 does not require ongoing updating of base location 2442 once it is initially established.

Referring still to FIG. 24b, one method of establishing base location 2442 is illustrated. In this illustration, using an approach similar to the registration approaches described previously, a tracking MIRRF 510 is attached in a known location relative to a scanning MIRRF that was attached during scanning. Using a probe 570 that is tracked using camera array 560, the body and image are first registered. In particular, the tip of probe 570 is first touched to known locations on MIRRF 510 such as divots at the locations corresponding to locations of scanning markers. A remote localization application 2440 compares the locations of the tip of the probe with the coordinates of the scanning markers in the image. This comparison is used establish a conformal mapping between the body and image reference frames. Then the tip of the probe is touched to a set of predetermined points on the base of guidance fixture 2400. Remote localization application 2440 uses the locations of the points on the base and the conformal map to establish base location 2442.

Using this procedure, once the base has been fixed to the head, and base location 2442 has been determined, there is no need to further track MIRRF 510 with the camera array. The patient can move around and, as long as workstation 580 receives the signals from sensors 2410, display 610 can provide feedback to the surgeon. Sensors 2410 can be coupled to workstation 580 in a number of ways, including using wires 2420 carrying electrical sensor signals. Alternatively, signals passing through optical fibers, or radio or optical signals transmitted through the air from the patient to a receiver attached to the workstation, can be used. In any of these cases, the patient is free to move around, as long as the sensor signals are passed to the workstation.

Figure 25A:
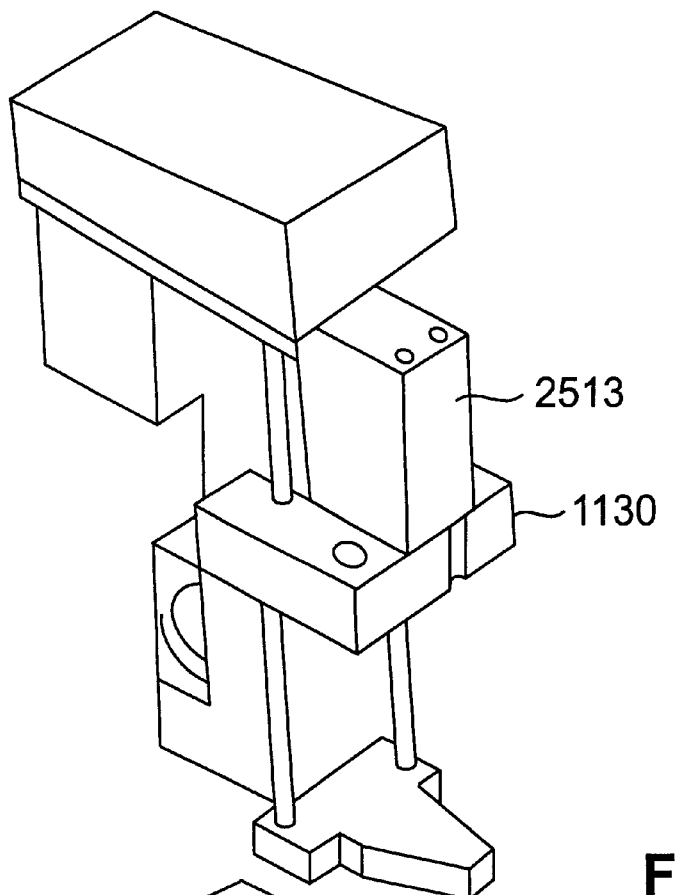
FIGS. 25a–b illustrate an actuated guidance fixture.
Figure 25A:
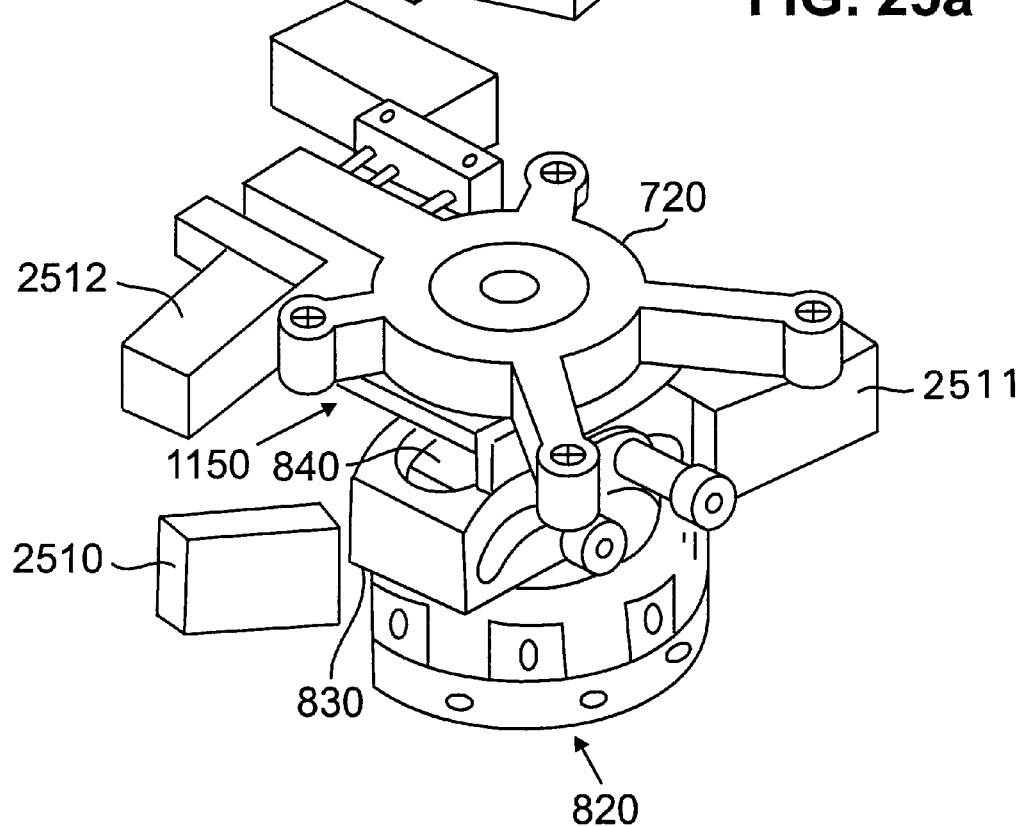

Separate from instrumentation of a guidance fixture, a guidance fixture can be actuated as an alternative to requiring that the guidance fixture be manually adjusted. Referring to FIG. 25a, an actuated guidance fixture 2500 includes a stepper motor 2513 that is couple to drive platform 1130. Rotation of stepper motor 2513 raises or lowers the drive platform, thereby displacing an attached instrument. The linear displacement of the drive platform is directly related to the angular rotation of the stepper motor. Actuated guidance fixture also includes motors 2510 and 2511, that rotate and pivot the guidance fixture, and two motors 2512 which adjust x-y table 1150.

Figure 25B:
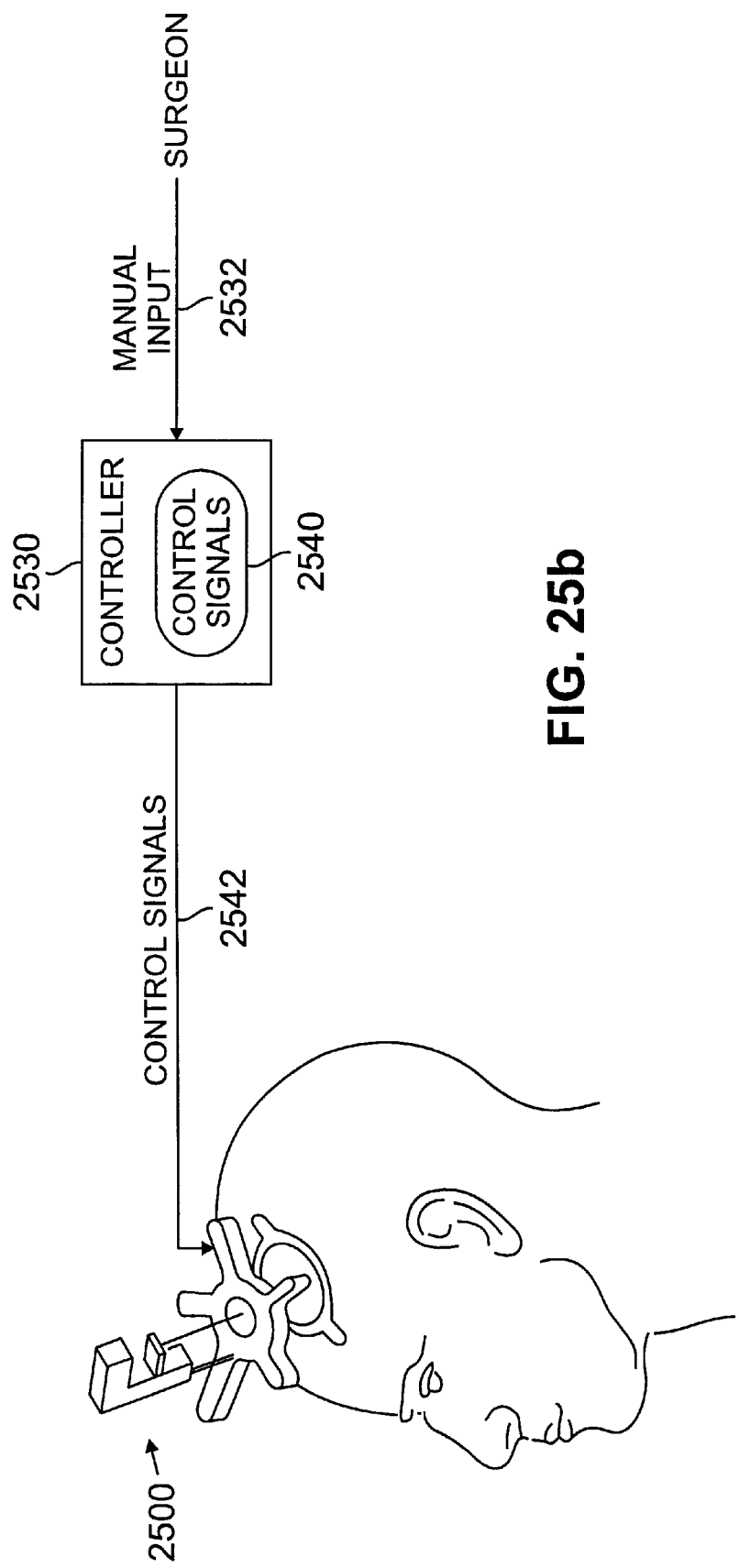

Referring to FIG. 25b, in one version of remote actuation of the guidance fixture, the surgeon provides manual input 2532 to a controller 2530 by manipulating manual controls.

Controller 2530 converts these manual inputs into control signals 2540 for driving motors 2510–2513. The surgeon relies on visual feedback, as in the previously described approaches, as he manipulates the manual controls.

Alternative versions of actuated guidance fixture 2500 can use different types of motors. For instance, hydraulic motors can be used and the guidance fixture and the controller can be coupled to the guidance fixture by hydraulic lines. This hydraulic approach provides electrical isolation between the patient and the workstation. Also, the entire guidance fixture and hydraulic motors can be fabricated from materials that do not interfere with scanning. This allows use of such an actuated fixture during scanning, which is useful in certain operative procedures.

Control signals provided to actuators on the guidance fixture can also be used to determine the configuration of the fixture. For instance, in controlling a stepper motor, the number of discrete "steps" commanded by a controller can be counted to determine the angle of rotation of the motor. This computed angle can be used in addition to, or even instead of, signals from sensors on the fixture.

Figure 26:
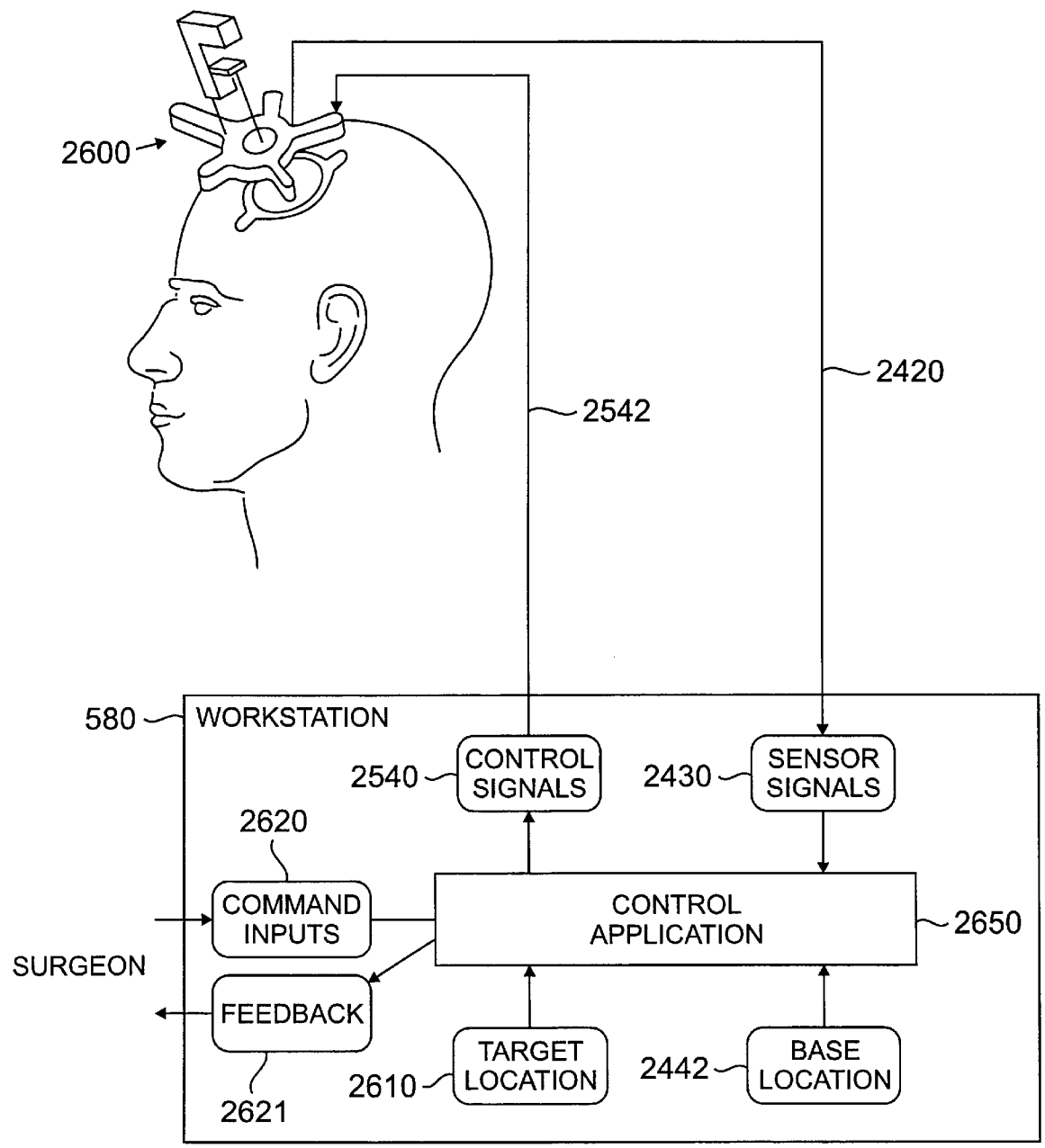
FIG. 26 illustrates a remotely controlled guidance fixture.

Referring to FIG. 26, a guidance fixture 2600 is both instrumented with sensors 2410–2413 (not shown) and actuated with motors 2510–2513 (not shown). Sensor signals 2430 are provided to a workstation 580 from sensors 2410–2413. The workstation computes motor control signals 2540 which are used to drive motors 2510–2513. In this arrangement, a control application 2650 executing on workstation 580 uses sensor signals 2430 as feedback information and controls the guidance fixture by generating motor control signals 2540. Control application 2650 also accepts base location 2442 which allows it to compute the location and orientation of the fixture in the frame of reference of the image or the body.

Control application 2650 accepts commands 2620 from the surgeon. These commands can range in complexity. An example of a simple command might be to displace a surgical instrument to a particular depth. A more complex command might be to align the guidance fixture with a planned target location. In the latter case, control application 2650 uses a stored target location 2610 and controls motors 2510–2513 to align the fixture. Even more complex commands can be used to invoke entire preprogrammed procedures. An example of such a preprogrammed procedure is to map a region of the brain by repeatedly positioning the x-y table and inserting and then withdrawing a recording electrode.

In addition to angular and position sensors, force sensors can be incorporated into an instrumented guidance fixture. Referring still to FIG. 26, control application 2650 can provide feedback signals 2621, including force feedback signals, to the surgeon.

Teleoperation

An actuated guidance fixture, such as actuated guidance fixture 2500, or actuated and instrumented guidance fixture 2600, described above, are applicable to telerobotic surgery in which the surgeon is distant from the patient. A surgical nurse, physician's associate, or some other assistant to the surgeon is in the some location as the patient. This assistant performs some functions, such as attaching the guidance fixture to the patient, but does not perform the actual surgery.

Figure 27:
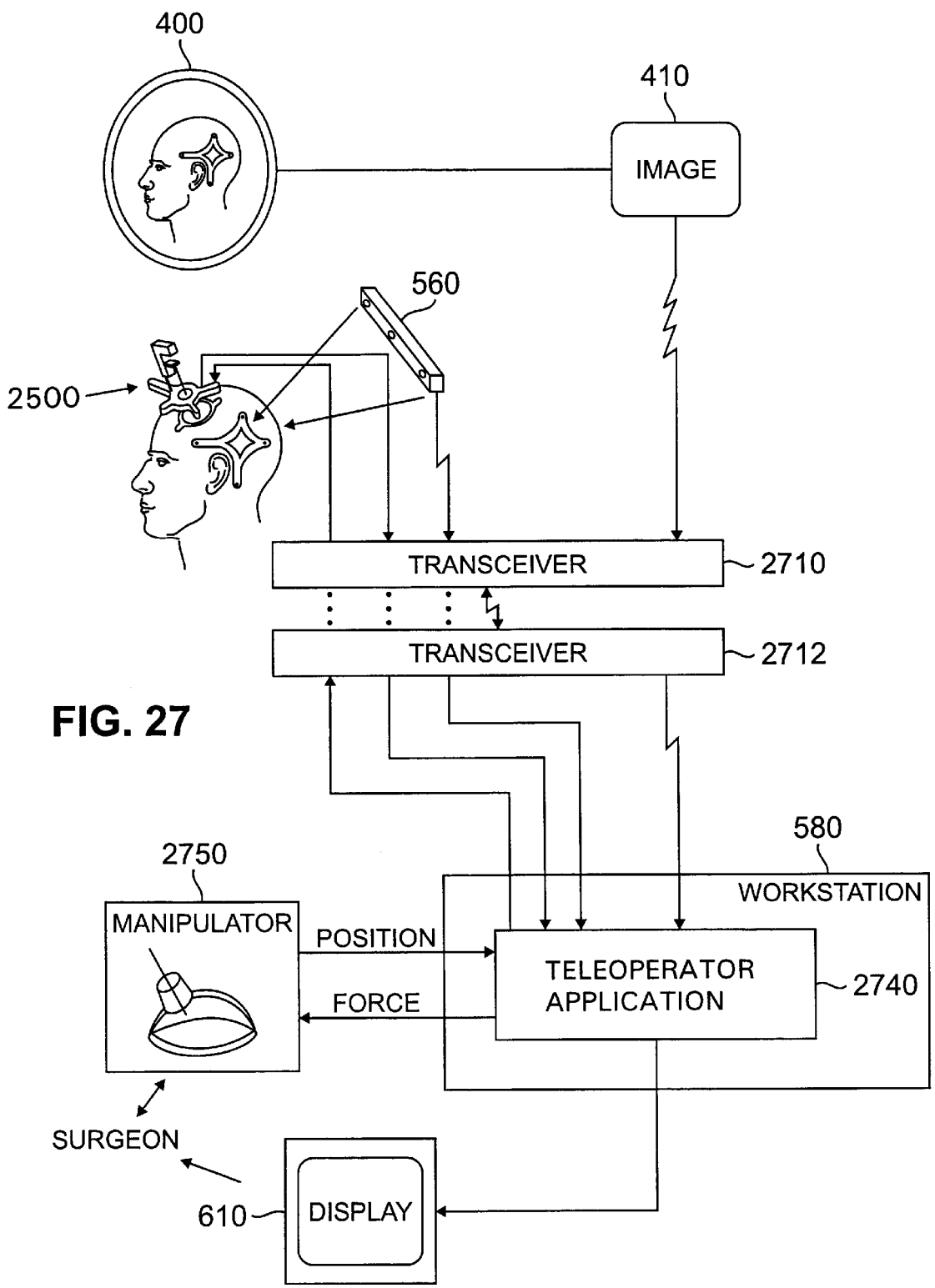
FIG. 27 illustrates a teleoperator configuration.

Referring to FIG. 27, a three-dimensional image 410 is produced by scanning a patient. Before scanning, the assistant has attached scanning markers, such as the scanning MIRRF described previously, to the patient. The image is sent to workstation 580 through a pair of transceivers 2710, 2712, one located near the patient, and one near the surgeon. The transceivers can be coupled by various types of channels, including a radio channel, or a data network connection. The surgeon locates the scanning markers in the image, and plans the surgical trajectory.

At the beginning of the surgical phase, the assistant locates the entry point and attaches an instrumented and actuated guidance fixture 2600 to the patient. After the fixture is attached, signals from the sensors are transmitted to workstation 580 through transceivers 2710, 2712, and control signals are transmitted back from workstation 580 through the transceivers to the fixture. In addition, images from camera array 560 are transmitted to the workstation. A registration step is carried out, in this case using a probe which is tracked by camera array 560.

Once guidance fixture 2600 is attached and registered, the surgeon controls the fixture remotely. Based on the sensor signals from the guidance fixture, workstation 580 computes images which are presented on display 610 as visual feedback to the surgeon. The surgeon can interact with the workstation in a number of ways. In FIG. 27, a manipulator 2750 is coupled to workstation 580. The manipulator includes a "phantom" jig and a manipulator fixture that is similar to the guidance fixture that is attached to the patient's head. The surgeon adjusts the manipulator fixture which provides control signals to a teleoperator application 2740 executing on workstation 580. Teleoperator application 2740 converts these control signal to motor control signals for guidance fixture 2600 and transmits the motor control signals to the guidance fixture. If the sensors on the guidance fixture include force sensors, teleoperator application 2740 receives force signals from guidance fixture 2600 which are used to control manipulator 2750 to provide for feedback to the surgeon.

During the surgery, the assistant is responsible to tasks such as attaching the guidance fixture, exchanging instruments in the guidance fixture, and surgical tasks such as opening the skull and closing the skin.

Various alternative manipulators 2750 can be used to provide a physical interface for the surgeon. For instance a joystick or a three dimensional pointer (e.g., an instrumented glove) can be used in conjunction with a head-mounted display in a virtual reality based arrangement.

Alternative Registration

In the approaches described above, in general, registration is performed using a remote sensing approach. The registration procedure is used to determine a conformal map between a coordinate system that is fixed relative to the body and the coordinate system of the scanned image. Alternative registration procedures do not rely on remote sensing. These registration procedures also include steps for determining the location and orientation of an attached base of a guidance fixture. If an instrumented guidance fixture is used, remote sensing is not required after the registration procedure is completed.

Figure 28:
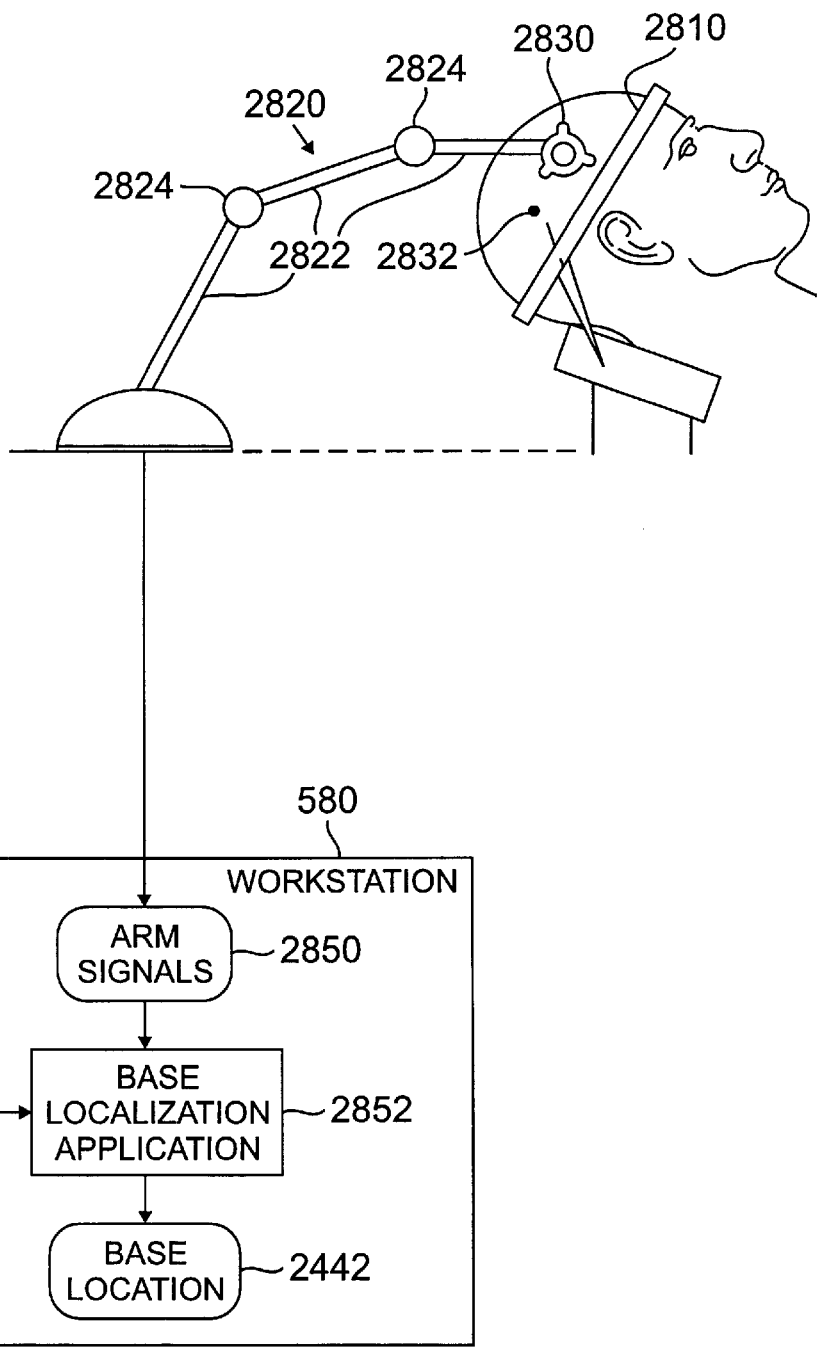
FIG. 28 illustrates locating a mounting base using a mechanical arm.

In one alternative approach illustrated in FIG. 28, initial registration and location of the mounting base is performed by securing the body in a fixed location relative to the base of an articulated arm 2820. For example, a head can be secured using a conventional head frame 2810. The angles in the joints 2822 of articulated arm 2830 provide signals to workstation 580 which are used to determine the location of the end of the arm relative to the base.

The procedure for determining the location and orientation of the base in the image coordinate system is as follows. Articulated arm 2820 is coupled to workstation 580 and provides arm signals 2850, which encode the joint angles of the arm, to the workstation. A base localization application 2852, which executes on workstation 580, determines the coordinates of the end point of the arm in the reference frame of the base of the arm. In a first phase of the procedure, the surgeon touches the end point of the arm to each of a set of fiducial points 2832. Correspondingly, fiducial point coordinates 421 are stored on workstation 580. Using fiducial point coordinates 421 and the coordinates of the fiducial points in the reference frame of the arm, base localization application 2852 computes a conformal map between the image coordinate system and the arm coordinate system.

The second phase of the procedure, the surgical phase, involves three steps. First, the surgeon locates an entry point by pointing with the end of the arm and viewing the display to select an entry point. Next, the surgeon drills the burr hole at the entry point and attaches the mounting base. Finally, the surgeon touches the end of the arm to a set of predetermined points on a guidance fixture mounting base that has already been attached to the head. Using the locations of these points relative to the base of the arm and the conformal map computed in the first step, base localization application 2852 computes base location 2442.

In another alternative to registering the mounting base, a miniaturized mechanical arm is attached directly to the body, thereby not requiring the patient to be restrained during the registration and base localization procedure. The procedure is carried out as follows.

Figure 29A:
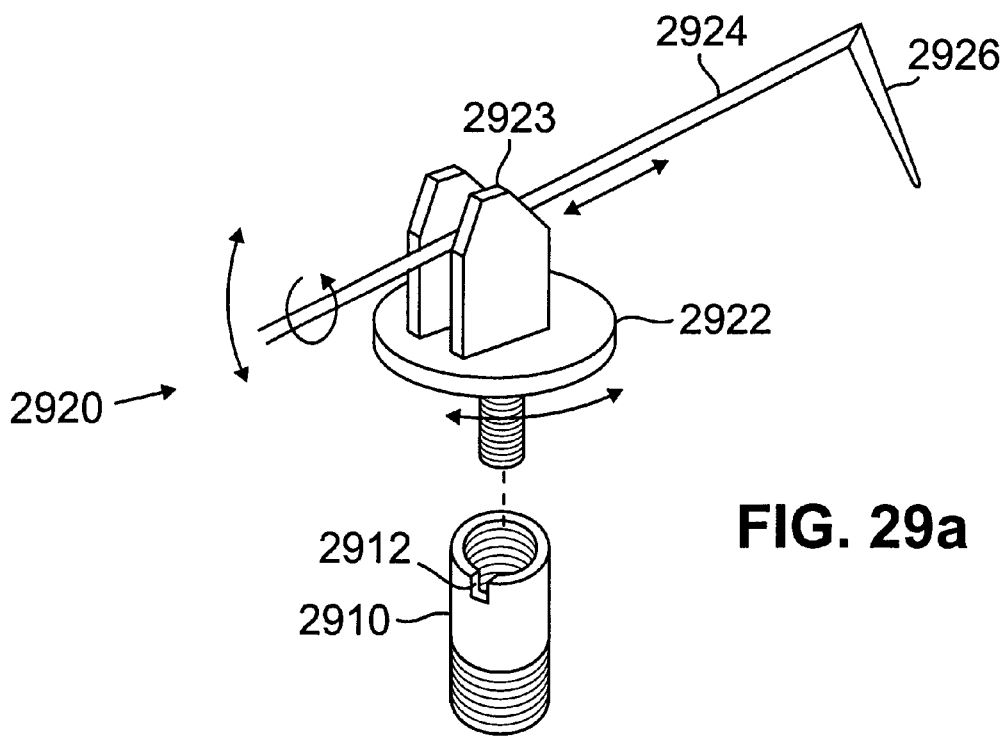
FIGS. 29a–d illustrate a head-mounted mechanical arm.
Figure 29B:
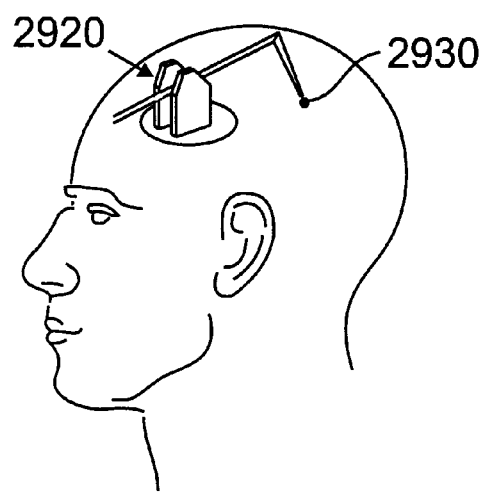

Referring to FIGS. 29a–b, a bone anchor 2910 is fixed in the skull prior to scanning. Using scanning markers attached to bone anchor 2910, the locations and orientations of the bone anchors in the coordinate system of the image are determined after the scan is obtained. The attached scanning markers are such that the orientation as well as location of each bone anchor can be determined. For instance, a small array of scanning markers can be attached to each bone anchor, and the rotation of the array can be constrained by the position of an index point 2912 on the bone anchor.

A miniature arm 2920 is attached to bone anchor 2910. In particular, an arm base 2922 is attached to bone anchor 2910. Base 2922 mates with index point 2912 thereby constraining its rotation about the central axis of the bone anchor. Since the location and orientation of the bone anchor was previously determined form the scanned image, a conformal map between the reference frame of miniature arm 2920 and the image reference frame is computed without requiring any registration step. The surgeon can touch a set of fiducial points to verify the accuracy of the conformal map.

Referring to FIG. 29a, miniature arm 2920 includes an instrumental joint 2923 through which a shaft 2924 passes. Joint 2923 allows four degrees of freedom. These degrees of freedom are (a) rotation around a control axis of base 2922 (i.e., around the central axis of bone anchor 2910), (b) elevation relative to the base, (c) rotation of the shaft along its axis, and (d) extension of the shaft. Joint 2923 includes sensors which generates signals encoding these four motions. These signals are provided to workstation 580 (not shown in FIGS. 29a-b). A pointer 2926 is rigidly attached to shaft 2924. For any position of the tip of pointer 2926, workstation 580 computes the coordinates of the tip relative to arm base 2922. Using the conformal map, the workstation then computes the coordinates of the tip of the arm in the reference frame of the image.

Referring to FIG. 29b, miniature arm 2920 is used to locate entry point 2930 and subsequently registering a mounting base attached over the entry point.

Figure 29C:
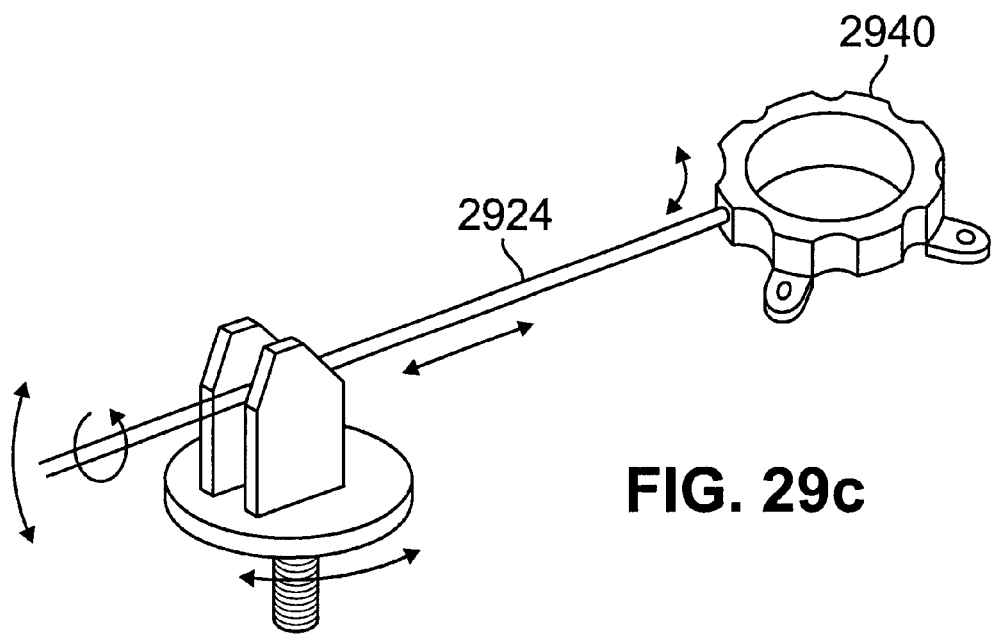
Figure 29D:
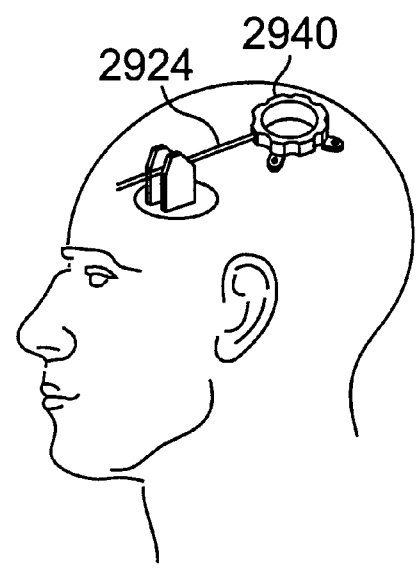

Alternatively, referring to FIGS. 29c–d mounting base 2940 can be directly attached to shaft 2924. In this way, an entry point is selected by moving the mounting base, and attaching the base to the skull while it is still attached to shaft 2924.

After the instrumented guidance fixture is attached to the mounting base, the arm is no longer required and can be removed from the bone anchor.

Spinal and General Surgery

Another aspect of the invention relates to spinal and general surgery. These approaches include several steps that are in common with the approaches to brain surgery described above.

In spinal surgery, the approach is useful for complex spinal procedures, such as implantation of vertebral pedicle fixation screws for fusion. Clinical conditions in which this approach may be useful include degenerative disc and bone disease, tumor, trauma, congenital or developmental abnormalities, and infection.

Figure 30:
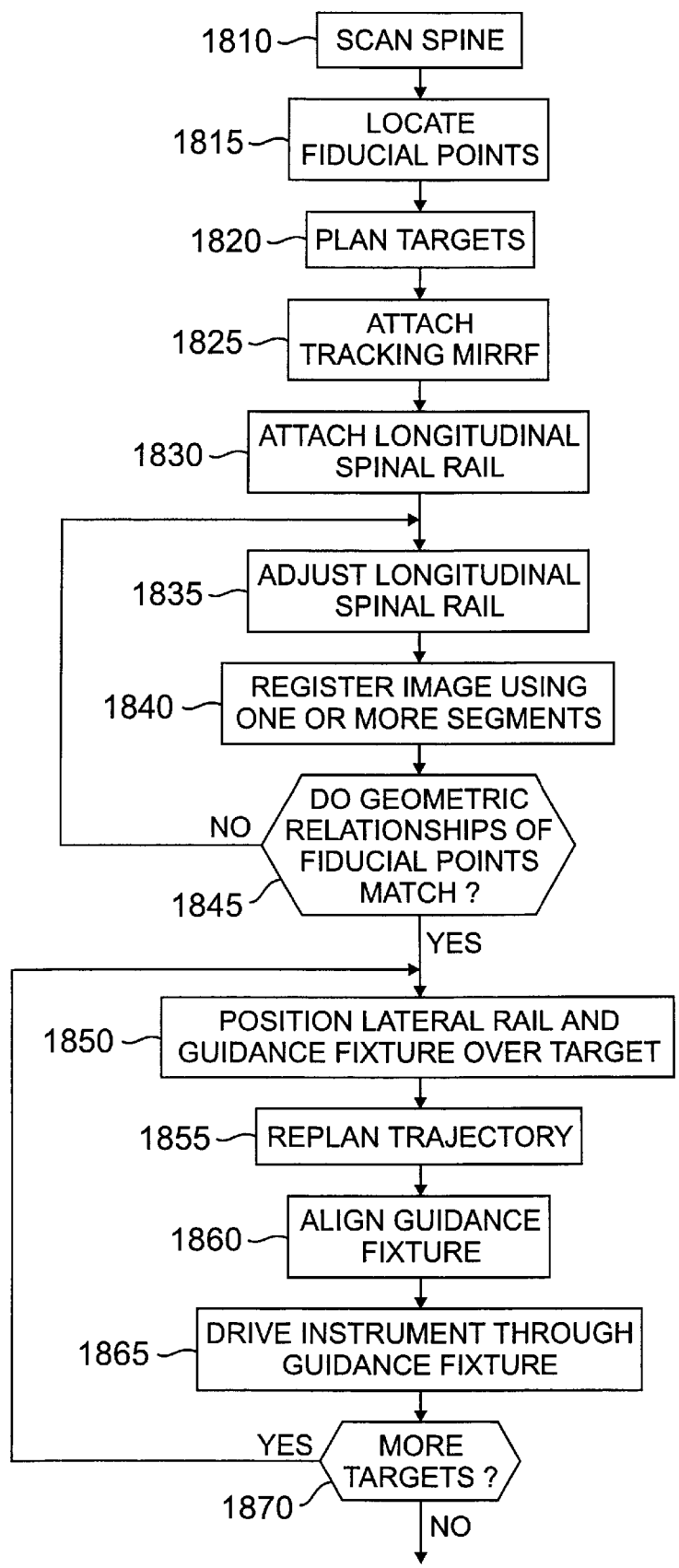
FIG. 30 is a flowchart of a spinal surgery procedure.
Figure 31A:
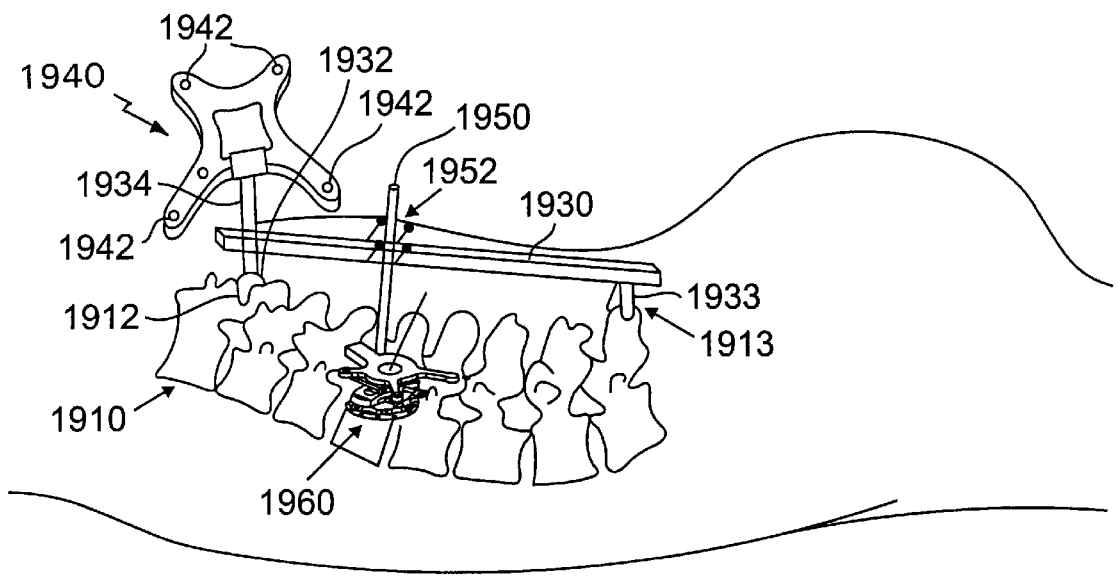
FIGS. 31a–b illustrate a guidance fixture attached to spinal rails for spinal surgery.
Figure 31B:
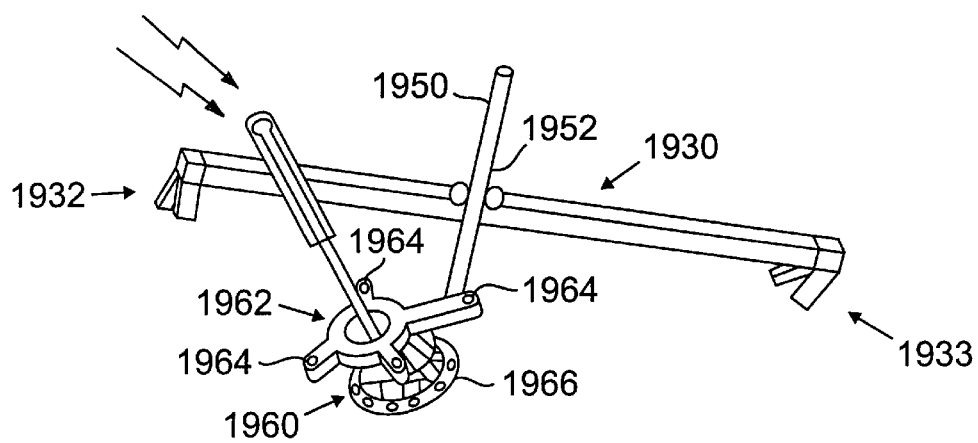

Referring to the flowchart in FIG. 30, in spinal surgery, the procedure follows a similar sequence of steps as in the brain surgery procedure shown in FIG. 1. Referring to FIGS. 31a–b, the spine 1910 is scanned to produce a three-dimensional spinal image (step 1810). Rather than attaching scanning markers to the body prior to scanning, fiducial points are anatomical points of spinal structure that can be located both on spine 1910 during surgery and in the spinal image. Fiducial coordinates of these anatomical points are determined in the same manner as fiducial coordinates of images of scanning markers are found in the previously described brain surgery procedures, for example by manually positioning a cursor on a display of the spinal image (step 1815). One or more target points are also located in the three-dimensional spinal image (step 1820).

During the surgical phase of the procedure, the patient is positioned on an operating table and spine 1910 exposed. The patient's position is adjusted so that the curvature of the patient's spine 1910 matches the curvature in the spinal image in as close a fashion as possible. For instance, the surgeon matches an actual interspinous distance equal to the corresponding interspinous distance in the scanned image.

A tracking MIRRF 1940 is attached to a spinous process 1912 by a spinous clamp 1932 and a clamping post 1934 (step 1825). Spinous process 1912 is, in general, the most rostral of the spinous processes to be studied during a posterior spinal surgical approach. MIRRF 1940 has a similar shape to tracking MIRRF 510 (FIG. 5), although MIRRF 1940 can have a variety of shapes. MIRRF 1940 includes tracking LEDs 1942.

A longitudinal spinal rail 1930 is also attached to exposed spine 1910 (step 1830). One end of spinal rail 1930 is attached to spinous process 1912 by spinous clamp 1932. A second spinous clamp 1933 is used to secure the other end of spinal rail 1930 to another spinous process 1913. Longitudinal spinal rail 1930 has distance markers that are used to measure the separation of spinous clamps 1932 and 1933 to allow the surgeon to obtain an appropriate correspondence to the patient's position and spine curvature at the time of scanning (step 1835). Various sizes of longitudinal spinal rails can be used depending on how many segments of spine are to be operated upon.

A registration step is then carried out (step 1840). A probe with probe LEDs attached to it is tracked using a camera array. In a procedure similar to that described above for brain surgery, the coordinates of the fiducial points in the reference frame of MIRRF 1940 are computed after positioning the probe at the fiducial points. These are matched to the fiducial coordinates found in the spinal image. Registration can be performed using fiducial points on only one segment of spine 1910. Because the curvature of the spine during surgery is adjusted using longitudinal spinal rail 1930 to match the curvature in the spinal image, the remaining segments of spine 1910 between spinous processes 1912 and 1913 are also accurately registered. Fiducial points on multiple segments of spine 1910 can also be used for registration. If the geometric relationship between the fiducial coordinates in the spinal image does not match the geometric relationship of the coordinates of the fiducial points in the reference frame of MIRRF 1940 (step 1845), one possible source of error is inadequate matching of the curvature of the spine to the curvature at the time of scanning. In the case of inadequate matching of the curvature, the surgeon can readjust longitudinal spinal rail 1930 (step 1835) and attempt the registration step again until an adequate conformal mapping can be computed.

A lateral spinal rail 1950 is then attached to longitudinal spinal rail 1930 using a mobile rotatory joint 1952. Attached to lateral spinal rail 1950 is a guidance fixture 1960. Guidance fixture 1960 includes a planar base 1962 and tracking LEDs 1964 of similar structure to guidance fixture 710 (FIG. 9). Guidance fixture 1962 does not, in general, include a guidance tube. A mounting base 1966 of guidance fixture 1960 clamps to lateral spinal rail 1950.

Exemplary spinal surgical procedures involve insertion of a pedicle screw and insertion of an intervertebral fixation cage into spine 1910 for spinal stabilization and fusion. These surgical procedures proceed as follows.

Guidance fixture 1960 is positioned over the targeted position by sliding lateral spinal rail 1950 along longitudinal spinal rail 1940 and securely tightening mobile rotatory joint 1952, and then securely tightening guidance fixture 1960 in position on lateral spinal rail 1950 (step 1850). An example of a targeted position is the left pedicle of the L1 vertebral body.

A trajectory from guidance fixture 1960 to the targeted position is then replanned (step 1855). The replanned trajectory can be checked to verify that it avoids critical neural structures. Guidance fixture 1960 is then aligned using the two-step rotation and pivoting procedure described above, using visual feedback in a navigational view (step 1860).

If the surgical procedure involves pedicle screw fixation, a drill is introduced through guidance fixture 1960 and a hole is drilled through the pedicle into the vertebral body, without violating any critical neural structure. The pedicle screw is then introduced into the pedicle through the guidance fixture 1960 (step 1865). As with the instrument drive used for brain surgery, the drill can include a tracking LED attached to it for tracking insertion of the drill.

If the procedure involves another target on the spine (step 1870), mobile rotatory joint 1952 and guidance fixture 1960 are then loosened, and lateral spinal rail 1950 and guidance fixture 1960 are slipped over to the next appropriate target and the above procedure is repeated. In this fashion, rapid insertion of pedicle screws is accomplished.

If the surgical procedure involves insertion of intervertebral fixation cages guidance fixture 1960 is targeted towards a disc space. The disc is removed through guidance fixture 1960 using a standard disc removal system. The fixation cage is then inserted using guidance fixture 1960 into the intervertebral space.

In the surgical procedure involves percutaneous spinal fixation, incisions are made to expose spinous processes 1912, 1913 and longitudinal spinal rail 1930 and MIRRF 1940 are attached as described above. After registration using one or both of the exposed spinous processes, guidance fixture 1960 is attached and aligned on a trajectory through the pedicle or the intervertebral disc space. A small incision is made in the skin underneath guidance fixture 1960. An insertion tube is then be placed through guidance fixture 1960 so as to rapidly dissect through muscle and direct along the trajectory path and directed towards the pedicle or the intervertebral disc space. Using the techniques described above, the pedicle screws or intervertebral fixation cages can then be applied.

Related procedures can also be used for spinal cord surgery. In spinal cord surgery, an electrode can be placed within the spinal cord to make electrical measurements. Then, other surgical instruments can be introduced into the spinal cord based on the scanned image and the electrical measurements.

An alternative method of registration in spinal surgery uses instrumented miniature arm 2920 (FIG. 29a) is attached to the longitudinal spinal rail, rather than to a bone anchor 2910 as in the case of brain surgery. In a registration step, the surgeon positions the tip of arm 2924 at multiple anatomical point. Using the configuration of the arm when touching the points, the localization application executing on the workstation determines the location and orientation of the arm relative to the spine. The miniature arm is then used to orient the base of the guidance fixture. Since the base of the arm is at the known location and orientation relative to the spine, and the guidance fixture is at a known location and orientation relative to the base of the arm, the localization application can compute the location and orientation of the guidance fixture relative to the spine. This location and orientation is then displayed to the surgeon.

General Surgery

Figure 32A:
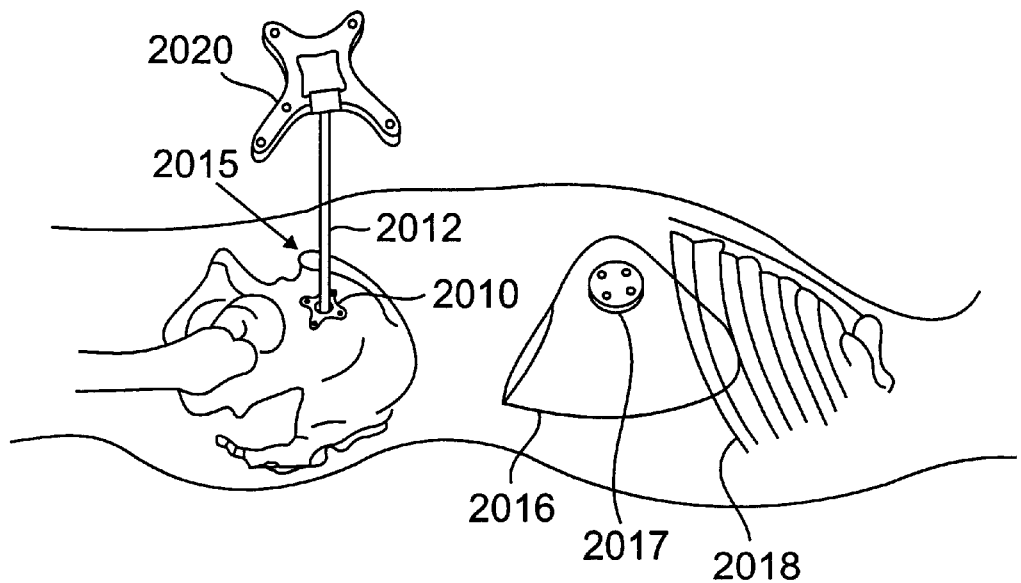
FIGS. 32a–b illustrate a guidance fixture attached to the pelvis for general surgery.
Figure 32B:
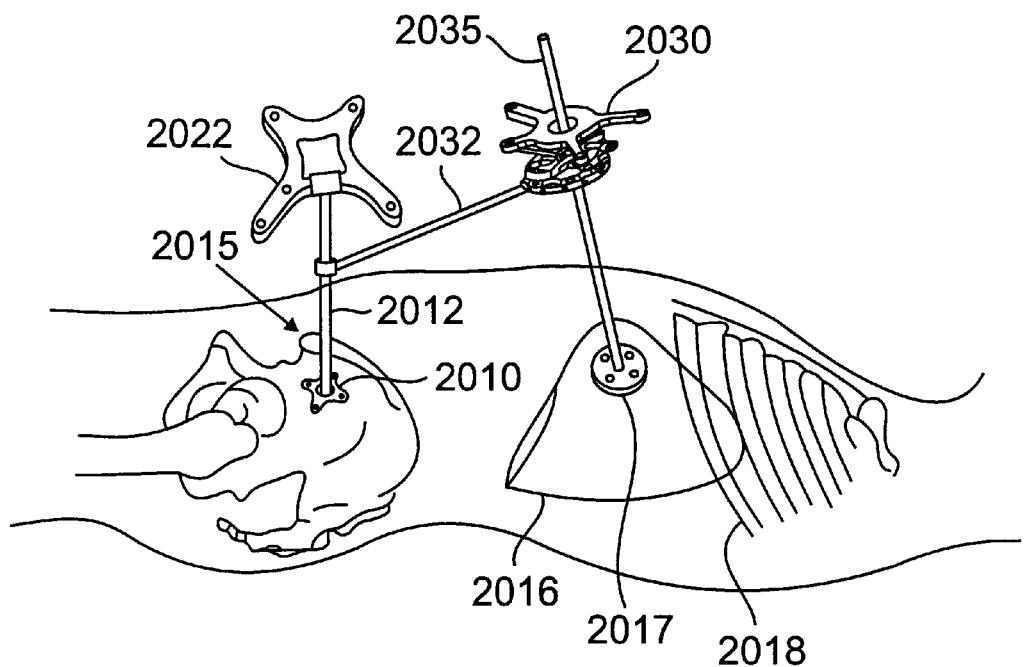

Another aspect of the invention relates to general surgery, such as abdominal surgery. Referring to FIGS. 32a–b, the approach is applicable, for example, for biopsy and draining of a liver cyst 2017. Referring to FIG. 32a, prior to scanning, a base plate 2010 is attached to the pelvis 2015, or another fixed bony structure, utilizing a percutaneous technique using several screws. A scanning MIRRF 2020 is attached to a column 2012 which is attached to base plate 2010. A scan of the patient is taken. A target is located in the scanned image within the body, in this example within the liver 2016. Column 2012 and scanning MIRRF 2020 are removed, and base plate 2010 is left attached to the patient.

Referring to FIG. 32b, at the time of surgery, column 2012 is reattached to base plate 2010 and a tracking MIRRF 2022 of the same geometry as scanning MIRRF 2020 is attached to column 2012. Registration of the tracking MIRRF with the image is performed using a surgical probe as in the brain surgery registration procedure described above.

In an approach similar to that used for spinal surgery, a guidance fixture 2030 is attached to column 2012 using a rod 2032 and a clamp. Using the trajectory replanning and two-step alignment procedure described above, guidance fixture 2030 is aligned with the planned target.

A small incision is made in the skin along the instrument trajectory. A guidance tube 2035 is then inserted through guidance fixture 2030 towards the target. A variety of general surgical instruments, such as an optical fiber for endoscopic visualization, an excision device, a vascular coagulator, a biopsy tube, or a drainage tube, can be passed through the guidance tube. The depth of penetration of the instrument is tracked using a workstation and displayed to the surgeon.

As an alternative to attaching column 2012 to a base plate attached to the pelvis, column 2012 can be attached to an inferior rib 2018 near the liver on the right upper quadrant of the abdomen, both anteriorly and posteriorly.

If a second surgical instruments is necessary, a secondary guidance fixture can attached to column 2012 and aligned by the same technique, and the second instrument passed through the secondary guidance fixture and through a second incision. Multiple instruments can be placed in this manner using multiple guidance fixtures.

Head-Mounted Camera Array

Figure 33:
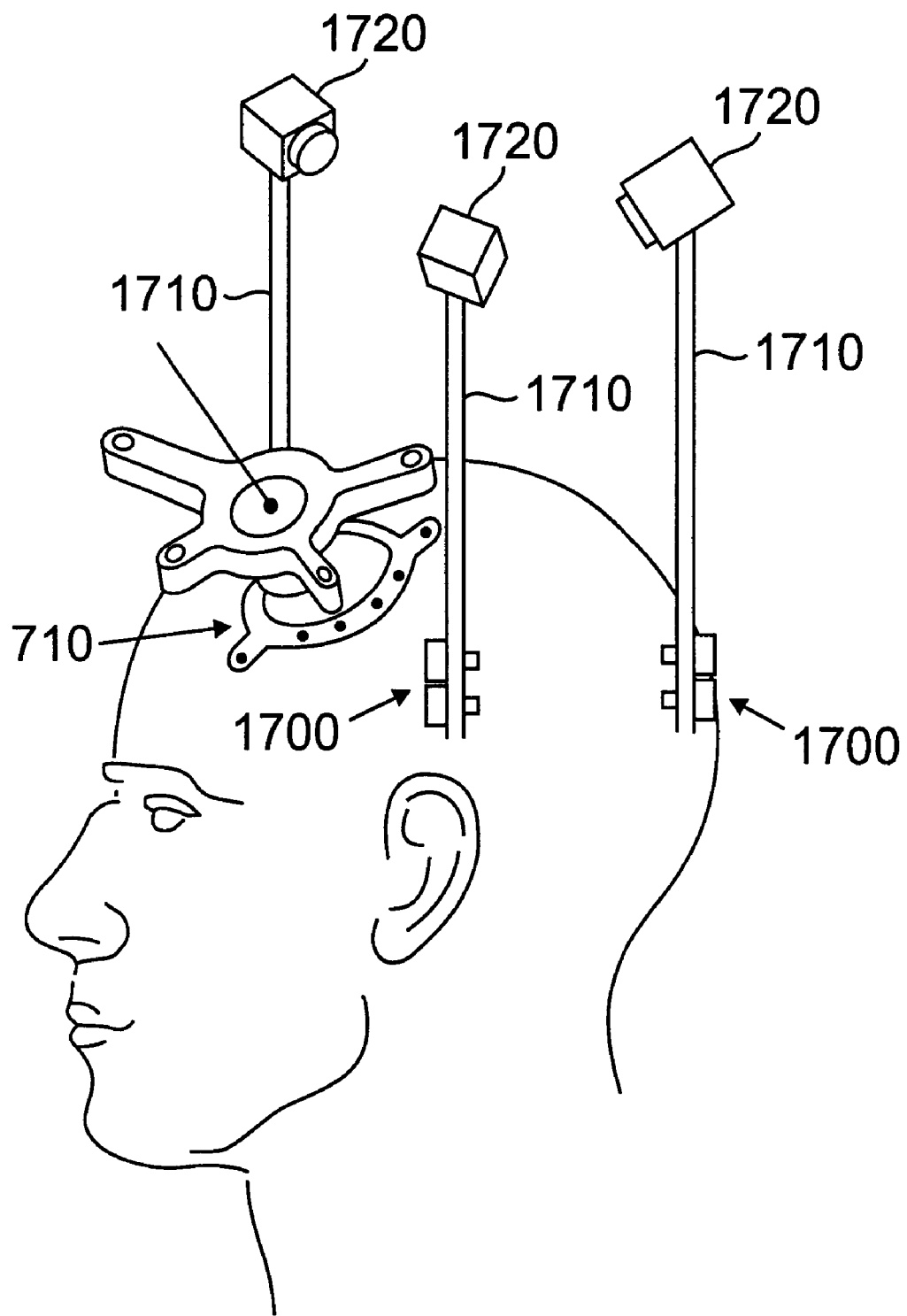
FIG. 33 is a head-mounted camera array.

In yet another alternative approach directed to stereotactic brain surgery, a lightweight camera array is attached directly to anchor screws mounted in the skull, as shown in FIG. 33. The camera array is used to track the location and orientation of a guidance fixture, probes, and instruments relative to the head. Since the cameras move with the patient, the patient can be free to move around without requiring separate tracking of the patient in order to compute the relative displacement of instruments relative to the patient.

Using this approach, two or more bone anchors 1700 are attached to the skull. Scanning markers are attached to anchors 1700 and the patient is scanned producing a three-dimensional image. Using techniques described above, the location and orientation of each bone anchor is determined from the scanned image.

At the time of surgery, carbon-fiber, acrylic or similar removable posts 1710 are attached to each of the bone anchors 1700. An array of cameras 1720, using CCD cameras with short focal-length lens, are fixed to the posts, directed roughly towards the skull.

Cameras 1720 serve the purpose of camera array 560 (FIG. 5) in the approaches in which the patient is free to move relative to the camera array. In this approach, although free to move around, the patient is essentially fixed relative to the cameras. There is therefore no need to track both the body and the guidance fixture since the body doesn't move relative to the cameras. Moreover, the locations and orientations of anchors 1700 in the image reference frame are determined by locating the scanning markers that are attached to these anchors prior to scanning. Since the geometry of posts 1710 is also known, the locations of the camera in the reference frame of the image are known. Essentially, the conformal map between the image reference frame and the camera reference frame can be pre-computed given the locations and orientations of the bone anchors. The location of an LED in the camera reference frame is determined from the digitalized images produced by cameras 1720 and then transformed to the image reference frame. In this way the location and orientation of guidance fixture 710 is tracked without requiring the surgeon to carry out explicit registration steps.

As an alternative to mounting the cameras on posts 1710, other types of mounting fixtures can be attached to anchors 1700. For instance, a single fixture can be mounted to multiple anchors. Also, a customized mounting fixture can be fabricated to position the cameras in a known position relative to the anchors.

Alternative Embodiments

Alternative related embodiments can make use of known geometric relationships of points on various devices. For instance, the relationship between the tip of a probe and the location of tracking LEDs can be calibrated and used by a localization application to compute the location of tip using the computed location the LEDs. Similarly, the relationship between the location of fiducial points on a MIRRF and tracking LEDs can be calibrated, thereby allowing a localization application to compute the coordinates of fiducial points from the coordinates of the tracking LEDs without using the registration procedure described above.

In the above embodiments, tracking LEDs are tracked using a camera. Other alternative embodiments can use other three-dimensional sensing and tracking approaches. Rather than LEDs, other tracking markers that are active emitters of electromagnetic or mechanical energy such as electronic sparks, heat, magnetic energy, or sound can be used. Appropriate three-dimensional tracking approaches, for example, using imaging or triangulation techniques determine the three-dimensional coordinates of the emitters. Alternatively, tracking markers that are passive reflectors or transducers of externally applied localizing energy, such as infrared light, sound, magnetism, can be used.

The devices described above can be made of a variety of materials. One alternative is to use a material, such as carbon fiber, which does not interfere with MRI scanning. This allows use of the devices during intraoperative MRI scanning. Also, use of hydraulic drive mechanisms rather than electrical motors avoids interference with MRI scanning.

In the surgical procedures described above, the patient is not necessary immobilized. It may be desirable, however, to immobilize the patient, for example by clamping the guidance fixture to an operating table, at some times during the surgery.

It is to be understood that the foregoing description is intended to illustrate and not limit the scope of the invention, which is defined by the scope of the appended claims. Other aspects, advantages, and modifications are within the scope of the following claims.

What is claimed is:

1. A method for positioning a surgical instrument during stereotactic surgery on a body, the body having been previously scanned to produce a three-dimensional image of the body which includes a target, the method comprising:

attaching a mounting device to a bone structure of the body;

registering the mounting device including
tracking a location of the mounting device, and
locating a plurality of fiducial points on the body in relation to the mounting device;

providing an adjustable guidance fixture that includes a base and an instrument guide adjustably coupled to the base for guiding the surgical instrument along a constrained trajectory relative to the instrument guide, said guidance fixture enabling a plurality of constrained adjustments of the instrument guide relative to the base;

tracking a location and orientation of the instrument guide and computing a position of the constrained trajectory in the three-dimensional image;

fixing the base of the guidance fixture to the mounting device;

adjusting the guidance fixture relative to the mounting device including adjusting the guidance fixture using a first of the constrained adjustments and then adjusting the guidance fixture using a second of the constrained adjustments, so that the constrained trajectory of the instrument guide passes through the target;

driving the surgical instrument along the constrained trajectory toward the target; and removing the mounting device from the bone structure.

2. The method of claim 1 wherein attaching a mounting device to a bone structure includes attaching a rail to a spine.

3. The method of claim 1 wherein the mounting device includes a mounting plate and a rod attached to the mounting plate, and wherein attaching the mounting device to a bone structure includes attaching the mounting plate to the bone structure.

4. The method of claim 1 wherein in adjusting the guidance fixture, the first of the constrained adjustments includes a rotation of the instrument guide about a central axis of the base, and the second of the constrained adjustments includes a pivoting of the instrument guide to adjust an angle of the instrument guide and the central axis.

5. The method of claim 1 wherein attaching the mounting device to a bone structure of the body includes attaching a plurality of tracking markers to the mounting device, and wherein the method further comprises tracking a location of the mounting device using the tracking markers.

6. The method of claim 5 wherein locating the plurality of fiducial points on the body in relation to the mounting device includes locating said fiducial points relative to the tracking markers that are attached to the mounting device.

7. The method of claim 5 wherein the guidance fixture includes tracking markers fixed relative to the instrument guide, and wherein tracking the location and orientation of the instrument guide includes locating said tracking markers relative to the tracking markers that are attached to the mounting device.

8. A method for positioning a surgical instrument during stereotadtic surgery on a body, the body having been previously scanned to produce a three-dimensional image of the body which includes a target, the method comprising:
   attaching a mounting device to a bone structure of the body, including attaching a rail to a spine;
   locating a plurality of fiducial points on the body in relation to the mounting device;
   providing an adjustable guidance fixture that includes an instrument guide for guiding the surgical instrument along a constrained trajectory relative to the instrument guide;
   tracking a location and orientation of the instrument guide and computing a position of the constrained trajectory in the three-dimensional image;
   adjusting the guidance fixture relative to the mounting device so that the constrained trajectory of the instrument guide passes through the target;
   driving the surgical instrument along the constrained trajectory toward the target; and
   removing the mounting device from the bone structure;
   wherein attaching the rail to the spine includes clamping the rail to two spinous processes and adjusting the separation of the two spinous processes to match the separation of the two processes in three-dimensional scanned image, thereby matching a curvature of the spine with a corresponding curvature of the spine in the image.

9. A method for positioning a surgical instrument during stereotactic surgery on a body, the body having been previously scanned to produce a three-dimensional image of the body which includes a target, the method comprising:
   attaching a mounting device to a bone structure of the body, including attaching a rail to a spine;
   locating a plurality of fiducial points on the body in relation to the mounting device, including
      tracking a location and orientation of the rail using a remote sensing device,
      tracking a location of a point on a probe using the remote sensing device,
      positioning a point on the probe at the fiducial points, the fiducial points being anatomical points of one vertebral segment, thereby facilitating polysegmental tracking via unisegmental mapping registration, and
      comparing the tracked location and orientation of the rail and the tracked location of the point on the probe to determine the location of the fiducial points in relation to the rail;
   providing an adjustable guidance fixture that includes an instrument guide for guiding the surgical instrument along a constrained trajectory relative to the instrument guide;
   tracking a location and orientation of the instrument guide and computing a position of the constrained trajectory in the three-dimensional image;
   adjusting the guidance fixture relative to the mounting device so that the constrained trajectory of the instrument guide passes through the target;
   driving the surgical instrument along the constrained trajectory toward the target; and
   removing the mounting device from the bone structure.

10. A method for positioning a surgical instrument during stereotactic spinal surgery, the spine having been previously scanned to produce a three-dimensional image of the spine which includes a target on the spine, the method comprising:
   attaching a longitudinal rail to the spine, including clamping the longitudinal rail to two spinous processes and adjusting the separation of the two spinous processes to match a separation of the two processes in the three-dimensional image, thereby maintaining a fixed geometric relationship between the longitudal rail and a portion of the spine between the two spinous processes and matching a curvature of that portion spine with a corresponding curvature of that portion of the spine in the three-dimensional image;
   locating a plurality of anatomical fiducial points on the spine in relation to the longitudinal rail, including tracking a location of the longitudinal rail with using a remote sensing device, tracking a location of a probe positioned at each of the fiducial points using the remote sensing device, and comparing the location of the probe and the location of the longitudinal rail at each of the fiducial points;
   providing an adjustable guidance fixture that includes an instrument guide for guiding the surgical instrument along a constrained trajectory relative to the instrument guide;
   tracking a location and orientation of the instrument guide and computing a position of the constrained trajectory in the three-dimensional image;
   displaying a planar section of the three-dimensional image of the body in conjunction with a representation of the constrained trajectory, the planar section containing the target on the spine;
   adjusting the guidance fixture using a first constrained motion until the constrained trajectory of the instrument guide lies in a plane corresponding to the displayed planar section;
   adjusting the guidance fixture using a second constrained motion, such that the orientation continues to lie in the plane corresponding to the displayed planar section, until the constrained trajectory passes through the target point;
   driving the surgical instrument along the constrained trajectory toward the target, including tracking a location of the surgical instrument and displaying the location of the surgical instrument in conjunction with the scanned image.

\* \* \* \* \*

UNITED STATES PATENT AND TRADEMARK OFFICE
CERTIFICATE OF CORRECTION

PATENT NO. : 6,546,277 B1
DATED : April 8, 2003
INVENTOR(S) : Joel I. Franck, Frederick C. Haer and Ronald J. Franklin It is certified that error appears in the above-identified patent and that said Letters Patent is hereby corrected as shown below:

<u>Column 31,</u>
Line 21, "stereotadtic" should be -- stereotactic --.

Signed and Sealed this

Twenty-fifth Day of May, 2004

JON W. DUDAS
*Acting Director of the United States Patent and Trademark Office*